US008030517B2

(12) United States Patent  
Fleming et al.

(10) Patent No.: US 8,030,517 B2
(45) Date of Patent: *Oct. 4, 2011

(54) CCR9 INHIBITORS AND METHODS OF USE THEREOF

(75) Inventors: Paul E. Fleming, Wellesley, MA (US); Geraldine C. B. Harriman, Charlestown, RI (US); Zhan Shi, Concord, MA (US); B. Shaowu Chen, Sudbury, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/630,040

(22) Filed: Dec. 3, 2009

(65) Prior Publication Data

US 2010/0280074 A1 Nov. 4, 2010

Related U.S. Application Data

(63) Continuation of application No. 12/288,075, filed on Oct. 16, 2008, which is a continuation of application No. 11/601,025, filed on Nov. 17, 2006, now abandoned, which is a continuation of application No. 10/443,155, filed on May 21, 2003, now Pat. No. 7,238,717.

(60) Provisional application No. 60/383,573, filed on May 24, 2002.

(51) Int. Cl.
  *C07C 311/15* (2006.01)
  *C07D 213/02* (2006.01)
  *A61K 31/18* (2006.01)
  *A61K 31/44* (2006.01)
  *A61K 31/50* (2006.01)
  *A61P 1/00* (2006.01)
  *A61P 29/00* (2006.01)

(52) U.S. Cl. ............ 564/84; 564/92; 546/256; 514/602; 514/350

(58) Field of Classification Search .................... 564/84, 564/92; 514/602, 350; 546/256
See application file for complete search history.

(56) References Cited

U.S. PATENT DOCUMENTS

| | | |
|---|---|---|
| 2,997,368 A | 8/1961 | Barent et al. |
| 3,121,103 A | 2/1964 | Keller et al. |
| 3,344,183 A | 9/1967 | Reeder et al. |
| 3,442,946 A | 5/1969 | Keller et al. |
| 3,534,062 A | 10/1970 | Wright et al. |
| 3,551,427 A | 12/1970 | Ott et al. |
| 3,842,082 A | 10/1974 | Hunziker et al. |
| 4,166,452 A | 9/1979 | Generales, Jr. |
| 4,256,108 A | 3/1981 | Theeuwes |
| 4,265,874 A | 5/1981 | Bonsen et al. |
| 4,372,975 A | 2/1983 | Mouzin et al. |
| 4,954,518 A | 9/1990 | Takano et al. |
| 4,992,091 A | 2/1991 | Vinogradoff et al. |
| 4,997,940 A | 3/1991 | Vinogradoff et al. |
| 5,021,591 A | 6/1991 | Vinogradoff et al. |
| 5,071,468 A | 12/1991 | Astles et al. |
| 5,093,364 A | 3/1992 | Richards et al. |
| 5,155,121 A | 10/1992 | Niewohner et al. |
| 5,163,995 A | 11/1992 | Van Heertum et al. |
| 5,185,348 A | 2/1993 | Niewohner et al. |
| 5,217,521 A | 6/1993 | Durr |
| 5,217,976 A | 6/1993 | Ratcliffe et al. |
| 5,236,937 A | 8/1993 | Bradbury et al. |
| 5,294,620 A | 3/1994 | Ratcliffe et al. |
| 5,338,755 A | 8/1994 | Wagon et al. |
| 5,481,005 A | 1/1996 | Wagon et al. |
| 5,541,186 A | 7/1996 | Breu et al. |
| 5,571,775 A | 11/1996 | Van Heertum et al. |
| 5,589,478 A | 12/1996 | Yamada et al. |
| 5,780,488 A | 7/1998 | Bergman et al. |
| 5,973,148 A | 10/1999 | Ringer et al. |
| 6,136,971 A | 10/2000 | Harrington et al. |
| 6,200,995 B1 | 3/2001 | De la Brouse-Elwood et al. |
| 6,297,195 B1 | 10/2001 | Gesing et al. |
| 6,297,239 B1 | 10/2001 | deSolms et al. |
| 6,316,450 B1 | 11/2001 | Bromidge et al. |
| 6,403,607 B1 | 6/2002 | Hidaka et al. |
| 6,432,624 B1 | 8/2002 | Kikuchi et al. |
| 6,653,332 B2 | 11/2003 | Jaen et al. |
| 6,770,648 B2 | 8/2004 | McGee et al. |
| 6,939,885 B2 | 9/2005 | Ungashe et al. |
| 7,238,717 B2 * | 7/2007 | Fleming et al. ............... 514/350 |
| 7,282,502 B2 | 10/2007 | Fleming et al. |
| 7,582,661 B2 | 9/2009 | Ugashe et al. |
| 2002/0009116 A1 | 1/2002 | Kobayashi et al. |
| 2002/0012680 A1 | 1/2002 | Patel et al. |
| 2002/0013314 A1 | 1/2002 | Zhu et al. |
| 2002/0037905 A1 | 3/2002 | Dahl et al. |
| 2002/0037928 A1 | 3/2002 | Jaen et al. |
| 2002/0052363 A1 | 5/2002 | Dinsmore et al. |
| 2002/0065303 A1 | 5/2002 | Zhu et al. |
| 2002/0072530 A1 | 6/2002 | Zhu et al. |

(Continued)

FOREIGN PATENT DOCUMENTS

CH 561703 3/1975

(Continued)

OTHER PUBLICATIONS

Street, Jonathan D. et al., "Cyclising Nucleophilic Addition to Azinium Systems, Part 2. Reactions of 3-acylpyridinium hydrazones," *Journal of Chemical Research, Synopses*, vol. 5 (1987), pp. 154-155 (abstract only).

(Continued)

*Primary Examiner* — Venkataraman Balasubramanian

(57) ABSTRACT

The invention relates to compounds represented by Structural Formula I, which can bind to CCR9 receptors and block the binding of a ligand (e.g., TECK) to the receptors. The invention also relates to a method of inhibiting a function of CCR9, and to the use compounds represented by Structural Formula I in research, therapeutic, prophylactic and diagnostic methods.

14 Claims, No Drawings

U.S. PATENT DOCUMENTS

| | | |
|---|---|---|
| 2002/0103202 A1 | 8/2002 | Pinto et al. |
| 2003/0060460 A1 | 3/2003 | Ohuchida et al. |
| 2003/0139390 A1 | 7/2003 | McGee et al. |
| 2004/0167113 A1 | 8/2004 | Ugashe et al. |
| 2004/0171654 A1 | 9/2004 | Ugashe et al. |
| 2005/0137193 A1 | 6/2005 | Ungashe et al. |

FOREIGN PATENT DOCUMENTS

| | | |
|---|---|---|
| CH | 585222 | 1/1977 |
| DE | 2022187 C3 | 11/1970 |
| DE | 2257443 | 5/1973 |
| DE | 3544409 A1 | 10/1986 |
| DE | 3825041 A1 | 2/1990 |
| EP | 0015214 B1 | 9/1980 |
| EP | 0526348 B1 | 2/1993 |
| EP | 0556673 B1 | 8/1993 |
| EP | 0613894 B1 | 9/1994 |
| GB | 884847 | 12/1961 |
| GB | 1332697 | 10/1973 |
| JP | 6-113060 | 4/1994 |
| JP | 145145 | 5/1994 |
| JP | 89412 | 4/2001 |
| JP | 4364168 B2 | 8/2009 |
| WO | WO 93/03013 | 2/1993 |
| WO | WO 94/20142 | 9/1994 |
| WO | WO 95/33462 | 12/1995 |
| WO | WO 96/08483 | 3/1996 |
| WO | WO 97/28129 | 8/1997 |
| WO | WO 98/11218 | 3/1998 |
| WO | WO 98/28270 | 7/1998 |
| WO | WO 98/50029 | 11/1998 |
| WO | WO 99/17777 | 4/1999 |
| WO | WO 99/32433 | 7/1999 |
| WO | WO 99/38845 | 8/1999 |
| WO | WO 99/42465 | 8/1999 |
| WO | WO 99/55324 | 11/1999 |
| WO | WO 99/55663 | 11/1999 |
| WO | WO 00/05214 | 2/2000 |
| WO | WO 00/62778 | 10/2000 |
| WO | WO 01/00579 A1 | 1/2001 |
| WO | WO 01/09097 A1 | 2/2001 |
| WO | WO 01/17971 A1 | 3/2001 |
| WO | WO 01/19788 A2 | 3/2001 |
| WO | WO 01/19798 A2 | 3/2001 |
| WO | WO 01/32646 A2 | 5/2001 |
| WO | WO 01/56607 A1 | 8/2001 |
| WO | WO 01/56989 A2 | 8/2001 |
| WO | WO 01/57003 A1 | 8/2001 |
| WO | WO 01/57020 A1 | 8/2001 |
| WO | WO 01/60319 A2 | 8/2001 |
| WO | WO 01/60369 A1 | 8/2001 |
| WO | WO 02/00633 A1 | 1/2002 |
| WO | WO 02/18326 A1 | 3/2002 |
| WO | WO 02/30358 A2 | 4/2002 |
| WO | WO 02/054867 A1 | 7/2002 |
| WO | WO 02/055501 A2 | 7/2002 |
| WO | WO 02/059080 A2 | 8/2002 |
| WO | WO 03/099773 A1 | 12/2003 |
| WO | WO 2004/046092 A2 | 6/2004 |
| WO | WO 2004/058164 A2 | 7/2004 |
| WO | WO 2004/085384 A2 | 10/2004 |
| WO | WO 2004/099127 A1 | 11/2004 |
| WO | WO 2005/004810 A2 | 1/2005 |
| WO | WO 2005/112925 A1 | 12/2005 |
| WO | WO 2006/076644 A2 | 7/2006 |
| WO | WO 2007/014054 A2 | 2/2007 |

OTHER PUBLICATIONS

Street, Jonathan D. et al., "Cyclising Nucleophilic Addition to Azinium Systems. Part 2. Reactions of 3-Acylpyridinium Hydrazones," *Journal of Chemical Research* (S) (1987), pp. 154-155.

Danhardt, Gerd et al., "COX-1/COX-2 Inhibitors Based on the Methanone Moiety," *European Journal of Medicinal Chemistry*, vol. 37, (Feb. 2002), pp. 147-161.

Supplementary European Search Report issued Feb. 1, 2006 in European Application No. EP 03755422.7, which corresponds to U.S. Appl. Nos. 10/443,155 and 12/288,075.

International Search Report issued on Oct. 20, 2003 in PCT Application No. PCT/US03/16090, which corresponds to U.S. Appl. Nos. 11/391,633 and 12/288,075.

Haste, Sigrid et al., "Chemokine Receptor Inhibition by AMD3100 is Strictly Confined to CXCR4," *FEBS Letters*, vol. 527, (Sep. 11, 2002), pp. 255-262.

Street, Jonathan D. et al., "Cyclising Nucleophilic Addition to Azinium Systems," *Journal of Chemical Research Synopses*, No. 5, (1987) pp. 154-155. CA 108:37599 (1988).

West, Anthony R., "Solid State Chemistry and Its Applications," John Wiley & Sons, New York, (1988), pp. 358 & 365.

Vippagunta, S.R. et al., "Crystalline Solids," *Advanced Drug Delivery Reviews*, vol. 48, No. 1, (May 2001), pp. 3-26.

Kelsall, Brian L. et al., "Involvement of Intestinal Dendritic Cells in Oral Tolerance, Immunity to Pathogens, and Inflammatory Bowel Disease," *Immunological Reviews*, vol. 206, Issue 1, (Aug. 2005), pp. 132-148.

Yu, Cheng-Rong et al. "CCR9A and CCR9B: Two Receptors for the Chemokine CCL25/TECK/Ckβ-15 That Differ in Their Sensitivities to Ligand," *Journal of Immunology*, vol. 164, (2000), pp. 1293-1305.

Hatoum, O.A. et al., "The Intestinal Microvasculature As a Therapeutic Target in Inflammatory Bowel Disease," *Annals of the New York Academy of Sciences.*, vol. 1072 ,(2006), pp. 78-97.

Silvestri et al. "Anti-HIV-1 NNRT Agents: Acylamino Pyrryl Aryl Sulfones (APASs) as Truncated Analogues of Tricyclic PBTDs," *Medicinal Chemistry Research*, vol. 11, No. 4, (2002), pp. 195-218. CA 138: 187588 (2002).

International Search Report issued in PCT Application No. PCT/US03/16090, which corresponds to U.S. Appl. No. 11/391,633, Oct. 20, 2003.

Silvestri et al. Medicinal Chemistry Research, 11(4): 195-218, 2002. CA 138:187588, 2002.

Hatoum et al., Ann. N.Y. Acad. Sci. 1072: 78-97, 2006.

West, Anthony R., Solid State Chemistry and its Applications, Wiley, New York, 1988, pp. 358 & 365.

Vippagunta et al., Advanced Drug Delivery Reviews 48: 3-26, 2001.

Kelsall et al. Immunol. Rev. 20691): 132-148, 2005.

Yu et al. J. Immunol. 164(3): 1293-1305, 2000.

Hatse et al. FEBS Letters 527255-262, 2002.

Street et al. Journal of Chemical Research, Synopses, 5: 154-155, 1987. CA 108:37599,1988.

Campbell, Daniel J. et al., "Rapid Acquisition of Tissue-specific Homing Phenotypes by CD4+ T Cells Activated in Cutaneous or Mucosal Lymphoid Tissues," *Journal of Experimental Medicine*, vol. 195, (Jan. 7, 2002), pp. 135-141.

Dahinden, Clemens, A. et al., "Monocyte Chemotactic Protein 3 Is a Most Effective Basophil- and Eosinophil-activating Chemokine," *Journal of Experimental Medicine*, vol. 179, (Feb. 1994), pp. 751-756.

Dannhardt, Gerd et al., "COX-1/COX-2 Inhibitors Based on the Methanone Moiety," *European Journal of Medicinal Chemistry*, vol. 37, (2002), pp. 147-161.

Davidson, Natalie J. et al., "T Helper Cell 1-type CD4+ T Cells, but Not B Cells, Mediate Colitis in Interleukin 10-deficient Mice," *Journal of Experimental Medicine*, vol. 184, (Jul. 1996), pp. 241-251.

Kavanaugh, Arthur F. et al., "Role of CD11/CD18 in Adhesion and Transendothelial Migration of T Cells," *Journal of Immunology*, vol. 146, (Jun. 15, 1991), pp. 4149-4156.

Kontoyiannis, Dimitris et al., "Impaired On/Off Regulation of TNF Biosynthesis in Mice Lacking TNF AU-Rich Elements: Implications for Joint and Gut-Associated Immunopathologies," *Immunity*, vol. 10, (Mar. 1999), pp. 387-398.

Kosiewicz, Michele M. et al., "Th1-Type Responses Mediate Spontaneous Ileitis in a Novel Murine Model of Crohn's Disease," *Journal of Clinical Investigation*, vol. 107, No. 6, (Mar. 2001), pp. 695-702.

Kunkel, Eric J. et al., "Lymphocyte CC Chemokine Receptor 9 and Epithelial Thymus-expressed Chemokine (TECK) Expression Distinguish the Small Intestinal Immune Compartment: Epithelial Expression of Tissue-specific Chemokines as an Organizing Principle in Regional Immunity," *Journal of Experimental Medicine*, vol. 192, No. 5, (Sep. 4, 2000), pp. 761-767.

Lothrop, Warren C. et al., "Fluorenone-2,3-dicarboxylic Acid and its Anhydride," *Journal of the American Chemical Society*, CODEN:JACSAT, vol. 63, (Oct. 1941), pp. 2564-2567.

Murphy, Philip M., "The Molecular Biology of Leukocyte Chemoattractant Receptors," *Annual Review of Immunology*, vol. 12, (1994), pp. 593-633.

Neote, Kuldeep et al. "Molecular Cloning, Functional Expression, and Signaling Characteristics of a C-C Chemokine Receptor," *Cell*, vol. 72, (Feb. 12, 1993), pp. 415-425.

Panwala, Chetan M. et al., "A Novel Model of Inflammatory Bowel Disease: Mice Deficient for the Multiple Drug Resistance Gene, mdrla, Spontaneously Develop Colitis," *Journal of Immunology*., vol. 161 ,(1998), pp. 5733-5744.

Papadakis, Konstantinos A. et al. "The Role of thymus-Expressed Chemokine and Its Receptor CCR9 on Lymphocytes in the Regional Specialization of the Mucosal Immune System," *Journal of Immunology*, vol. 165, (2000), pp. 5069-5076.

Powrie, Fiona et al., "Phenotypically Distinct Subsets of CD4+ T Cells Induce or Protect from Chronic Intestinal Inflammation in C. B-17 *scid* mice," *International Immunology*, vol. 5, No. 11, (1993), pp. 1461-1471.

Qiuping, Zhang et al. "Selectively Increased Expression and Functions of Chemokine Receptor CCR9 on CD4+ T Cells from Patients with T-Cell Lineage Acute Lymphocytic Leukemia," *Cancer Research*, vol. 63, (Oct. 1, 2003), pp. 6469-6477.

Schaarschmidt, Alfred et al. "Darstellung von 1.4-Dimethyl-fluorenon and Versuch, dasselbe in ein Phenanthron-Derivat uberzufuhren," *ChemBer.*, CODEN:CHBEAM, vol. 53, (1920), pp. 1388-1399.

Schall, Thomas J., "Biology of the Rantes/Sis Cytokine Family", *Cytokine*, vol. 3, No. 3, (May 1991) , pp. 165-183.

Schall, Thomas J. et al., "Hemokines, Leukocyte Trafficking, and Inflammation," *Current Opinion in Immunology*, vol. 6, (1994), pp. 865-873.

Silvestri, Romano et al. "Anti-HIV-1 NNRT Agents: Acylamino Pyrryl Aryl Sulfones (APASs) as Truncated Analogues of Tricyclic PBTDs," *Medicinal Chemistry Research*, vol. 11, No. 4, (2002), pp. 195-218.

Street, Jonathan D. et al. "Cyclising Nucleophilic Addition to Azinium Systems. Part 2. Reactions of 3-Acylpyridinium Hydrazones,"*Journal of Chemical Research Synopses*, vol. 5, (1987), pp. 154-155.

Targan, Stephan R. et al., "A Short-Term Study of Chimeric Monoclonal Antibody cA2 to Tumor Necrosis Factor α for Crohn's Disease," *New England Journal of Medicine*, vol. 337, No. 15, (Oct. 9, 1997), pp. 1029-1035.

Uehara, Shoji et al. "A Role for CCR9 in T Lymphocyte Development and Migration," *Journal of Immunology*, vol. 168, (2002), pp. 2811-2819.

Ullmann F. et al. "Zur Darstellung von o-Aminobenzophenonderivaten", *ChemBer.*, CODEN:CHBEAM, vol. 35, (1902), pp. 4273-4280.

Van Riper, Gail et al. "Characterization and Species Distribution of High Affinity GTP-coupled Receptors for Human Rantes and Monocyte Chemoattractant Protein 1," *Journal of Experimental Medicine*, vol. 177, (Mar. 1993), pp. 851-856.

Wurbel, Marc-Andre et al. "Mice Lacking the CCR9 CC-chemokine Receptor Show a Mild Impairment of Early T- and B-cell Development and a Reduction in T-Cell Receptor γδ+ Gut Intraepithelial Lymphocytes," *Blood*, vol. 98, No. 9, (Nov. 1, 2001), pp. 2626-2632.

Youn, B.-S. et al., "Role of the CC Chemokine Receptor 9/TECK Interaction in Apoptosis," *Apoptosis*, vol. 7, (2002), pp. 271-276.

Zaballos, Angel et al. "Cutting Edge: Identification of the Orphan Chemokine Receptor GPR-9-6 as CCR9, the Receptor for the Chemokine TECK,"*Journal of Immunology*, vol. 162, (1999), pp. 5671-5675.

Kajfez, Franjo et al. "Synthetic Studies on 1,4-Benzodiazepines. Preparation of Various N(1)-Substituted-7-chloro-1,3-H-5-phenyl-1,4-benzodiazepines and their 2-deoxo Derivatives," *Acta Pharmaceutica Jugoslavica*, vol. 26, (1976), pp. 199-207.

Hunziker, Fritz et al. "Neuroleptic Piperazinyl Derivatives of 10$H$-thieno[3,2-c] [1] Benzazepines and 4$H$-thieno [2,3-c] [1] Benzazepines," *European Journal of Medicinal Chemistry*, vol. 16, No. 5, (1981), pp. 391-398.

Haider, Norbert et al. "Pyridazines XXVII[1]. Acylation Reactions and Procedures for Regio-Selective Alkylation of (5-Amino-4-Pyridaziny1)-Arylketones,"*Heterocycles*, vol. 23, No. 10, (1985), pp. 2651-2661.

Street, Jonathan D. et al. "Cyclising Nucleophilic Addition to Azinium Systems. Part 2. Reactions of 3-Acylpyridinium Hydrazones,"*Journal of Chemical Research*, vol. 5, (1987), pp. 1247-1285.

Arcus, C.L. et al. "Reactions of Organic Azides. Part IX[1]. Ring-expansions leading to 2-Phyl-(?iso)quinolono-and-(?iso)quinolino-(4',3'-4,5)thiazole and (?iso)Quinolono(3',4'-2,3)thiophen. Attempted Rearrangements of Fluorenone Hydrazone,"*Journal of the Chemical Society, Abstracts*, (Jan. 1, 1960), pp. 2098-2102.

Coombs, R.V. et al. "Synthesis and Antiinflammatory Activity of 1-Alky1-4-aryl-2(1$H$)-quinazolinones and Quinazolinethiones,"*Journal of Medicinal Chemistry*, vol. 16, No. 11, (1973), pp. 1237-1245.

Gorlitzer, Klaus, "Anellierte Chinolone II[2], N- und O-Alkylierungsprodukte," *Archiv der Pharmazie*, Weinheim, Germany, Vo. 312, (1979), pp. 254-261.

"Benzamide, N-cyclohexyl-2-[[(2,4-difluorophenyl)sulfonyl]amino]-N-2-pyridinyl- (CA Index Name)," CAS Registry No. 748147-95-7, entered Sep. 20, 2004.

* cited by examiner

CCR9 INHIBITORS AND METHODS OF USE THEREOF

CROSS-REFERENCE TO RELATED APPLICATION

This application is a continuation of U.S. application Ser. No. 12/288,075, filed Oct. 16, 2008 (pending), which is a continuation of U.S. application Ser. No. 11/601,025, filed Nov. 17, 2006 (abandoned), which is a continuation of U.S. application Ser. No. 10/443,155, filed May 21, 2003, now U.S. Pat. No. 7,238,717, which claims the benefit of U.S. Provisional Application No. 60/383,573, filed May 24, 2002, the contents of which are incorporated herein by this reference.

BACKGROUND OF THE INVENTION

Chemokines are a large and growing family of nearly forty 6-14 kD (non-glycosylated) heparin binding proteins that mediate a wide range of biological functions (Taub, D. D. and Openheim, J. J., *Ther. Immunol.*, 1:229-246 (1994)). The chemokines can be divided into families based on the position of four cysteine residues that form two disulfide bonds (Kelner, G. S., et al., *Science*, 266:12395-1399 (1994); Bazan, J. F., et al., *Nature*, 385:640-644 (1997); Pin, Y., et al., *Nature*, 385:611-617 (1997)). Chemokine receptors can also be divided into families based on the type of chemokine they bind, although, no clear structural differences have been identified that distinguish the receptor sub-families (Mackay, C. R., *J. Exp. Med.*, 184:799-802 (1996)).

Chemokines play a vital role in leukocyte adhesion and extravasation. For example, in various in vitro assays, chemokines can induce the chemotaxis or transendothelial migration of leukocytes (Taub, D. D. and Openheim, J. J., *Ther. Immunol.*, 1:229-246 (1994)), while in vivo injection (Taub, D. D., et al., *J. Clin. Invest.*, 97:1931-1941 (1996)) or over-expression of chemokines (Fuentes, M. E., et al., *J. Immunol.*, 155:5769-5776 (1995)) can result in leukocyte accumulation at the site of chemokine injection or expression. Antagonists of chemokines can prevent leukocyte trafficking (Bargatze, R. F. and Butcher, E. C., *J. Exp. Med.*, 178:367-372 (1993)) and may have beneficial effects on acute and chronic inflammation (Sekido, N., et al., *Nature*, 365:654-657 (1993); Karpus, W. J., et al., *J. Immunol.*, 155:5003-5010 (1995)). Chemokines have also been reported to modulate angiogenesis (Gupta, S. K., et al., *Proc. Natl. Acad. Sci. USA*, 92:7799-7803 (1995)), hematopoiesis (Taub, D. D. and Openheim, J. J., *Ther. Immunol.*, 1:229-246 (1994)) as well as T lymphocyte activation (Zhou, Z., et al., *J. Immunol.* 151:4333-4341 (1993); Taub, D. D., et al., *J. Immunol.*, 156:2095-2103 (1996)). In addition, several chemokine receptors act as co-receptors, along with CD4, for entry of M tropic and T tropic HIV-1 (Choe, H., et al., *Cell*, 85:1135-1148 (1996); Feng, Y., et al., *Science*, 272:872-877 (1996)).

Several subsets of CD4 lymphocytes can be defined based on their expression of various adhesion molecules that are known to effect trafficking to different physiologic sites (Mackay, C. R., *Curr. Opin. Immunol.*, 5:423-427 (1993)). For example, $CLA^{+ve}$ memory CD4 lymphocytes traffic to the skin (Berg, E. L., et al., *Nature*, 174(6):1461-1466 (1991)), while $CLA^{-ve}$ $\alpha4\beta7^{+ve}$ memory CD4 lymphocytes traffic to mucosal sites (Hamman, A., et al., *J. Immunol.*, 152:3282-3292 (1994)). Leukocyte adhesion to endothelium is thought to involve several overlapping steps including rolling, activation and arrest. Rolling leukocytes are exposed to factors expressed at the adhesion site resulting in activation of the leukocyte and up-regulation of integrin-mediated adhesion. As a consequence of such integrin-mediated interactions, leukocytes arrest on the endothelium (Bargatze, R. F. and Butcher, E. C., *J. Exp. Med.*, 178:367-372 (1993); Bargatze, R. F., et al., *Immunity*, 3:99-108 (1995)). Leukocyte activation and up-regulation of integrin molecules occurs via a pertussis toxin sensitive mechanism that is thought to involve chemokine receptors (Bargatze, R. F. and Butcher, E. C., *J. Exp. Med.*, 178:367-372 (1993); Campbell, J. J., et al., *Science*, 279:381-383 (1998)).

Memory $CD4^+$ lymphocytes can be grouped based upon the expression of certain chemokine receptors. For example, CXCR3, CCR2 and CCR5 (Qin, S., et al., *Eur. J. Immunol.*, 26:640-647 (1996); Qin, S., et al., *J. Clin. Invest.*, 101:746-754 (1998); Liao, F., et al., *J. Immunol.*, 162:186-194 (1999)) are all expressed on subsets of memory CD4 lymphocytes, and certain chemokines act selectively on naive T cells (Adema, G. J., et al., *Nature*, 387:713-717 (1997)). Furthermore, several chemokines which are ligands for such receptors have been shown to be expressed in inflammatory sites (Gonzalo, J. A., et al., *J. Clin. Invest.*, 98:2332-2345 (1996)) and in some cases in lymph nodes draining a challenged site (Tedla, N., et al., *J. Immunol.*, 161:5663-5672 (1998)). In vitro derived $T_H1/T_H2$ lymphocyte lines have also been shown to differentially express chemokine receptors. Specifically, $T_H1$ lymphocytes have been shown to selectively express CXCR3 and CCR5, while $T_H2$ lymphocytes selectively express CCR4, CCR8 and CCR3 (Bonecchi, R. G., et al., *J. Exp. Med.*, 187:129-134 (1998); Sallusto, F. D., et al., *J. Exp. Med.*, 187:875-883 (1998); Sallusto, F., *Science*, 277: 2005-2007 (1997); Andrew, D. P., et al., *J. Immunol.* 161: 5027-5038 (1998); Zingoni, A., et al., *J. Immunol.*, 161:547-555 (1998)). Interestingly, in some cases the chemokines for these respective chemokine receptors, such as MDC for CCR4 and IP-10 for CXCR3, are induced by cytokines associated with a $T_H1/T_H2$ environment (Andrew, D. P., et al., *J. Immunol.* 161:5027-5038 (1998); Luster, A. D., et al., *Nature*, 315:672-676 (1985)).

SUMMARY OF THE INVENTION

The present invention relates to compounds represented by Structural Formula I, and pharmaceutically acceptable salts, solvates, and hydrates of such compounds:

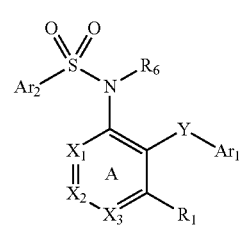

I.

In Structural Formula I, Y is C(O), O, S, S(O) or $S(O)_2$; $X_1$, $X_2$, and $X_3$ are each, independently, N or CR, provided that at least one of $X_1$, $X_2$, or $X_3$ is CR; R, for each occurrence, and $R_1$ are each, independently, H or a substituent. In preferred embodiments, the substituents at positions R and $R_1$ are each, independently, an aliphatic group, haloalkyl, aryl, arylalkyl, alkoxy, cycloalkoxy, haloalkoxy, aryloxy, arylalkoxy, alkylthio, halo, nitro, cyano, sulonamido, sulfone, sulfoxide, hydroxy, $NR_{11}CO_2R_{12}$, $C(O)N(R_{11})_2$, $C(O)R_{12}$, $CO_2R_{12}$, $OC(O)N(R_{11})_2$, $OC(O)R_{12}$, $N(R_{11})_2$, or $NR_{11}C(O)R_{12}$. $R_{11}$ and $R_{12}$ are defined further herein; $R_6$ is H, an aliphatic carbonyl group, or an aliphatic ester; and $Ar_1$ and $Ar_2$ are each, independently, a substituted or unsubstituted aryl group or a substituted or unsubstituted heteroaryl group. Preferably, $Ar_1$ is a substituted or unsubstituted phenyl, a substituted or unsubstituted pyridyl, a substituted or unsubstituted pyrimidinyl, or a substituted or unsubstituted pyrazinyl. Preferably, $Ar_2$ is a substituted or unsubstituted phenyl, or a substituted or unsubstituted pyridyl. More preferably, $Ar_1$ is a substituted phenyl and $Ar_2$ is substituted pyridyl. Ring A is substituted or unsubstituted.

In a preferred embodiment, compounds of the invention are represented by Structural Formula II:

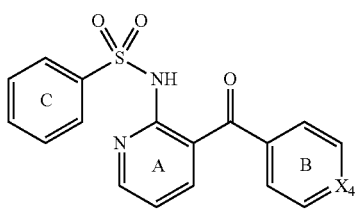

II.

In Structural Formula II, $X^4$ is N, $N^+$—$O^-$, or CR; and ring A, ring B, and ring C are each, independently, substituted or unsubstituted. R is H or a substituent. Examples of substituents for R are defined as in Structural Formula I.

In a more preferred embodiment, compounds of the invention are represented by Structural Formula III:

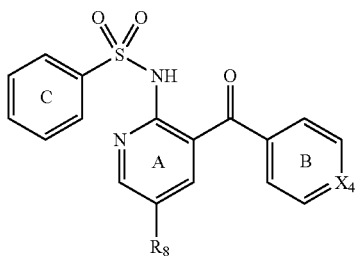

III.

In Structural Formula III, $X_4$ is N, $N^+$—$O^-$ or CR; ring A, ring B, and ring C are each, independently, substituted or unsubstituted, and R is H or a substituent. Examples of substituents for R are defined as in Structural Formula I; and $R_8$ is H or an electron withdrawing group. Preferably, $R_8$ is a halo, nitro, alkylcarbonyl or trihaloalkyl. More preferably, $R_8$ is Cl, Br or $NO_2$.

In another preferred embodiment, compounds of the invention are represented by Structural Formula IV.

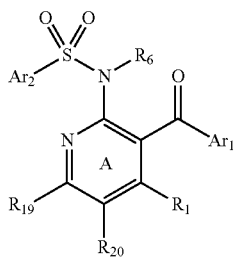

IV.

In Structural Formula IV, $Ar_1$, $Ar_2$, $R_1$ and $R_6$ are defined as in Structural Formula I; and $R_{19}$ and $R_{20}$ are each, independently, H or a substituent. Examples of substituents in the $R_{19}$ and $R_{20}$ positions include an aliphatic group, a haloalkyl group, an ester, an amide, alkylcarbonyl, a halogen, COOH, $NO_2$, alkoxy, haloalkoxy, CN, amino, and aminoalkyl.

In another preferred embodiment, compounds of the invention are represented by Structural Formula V.

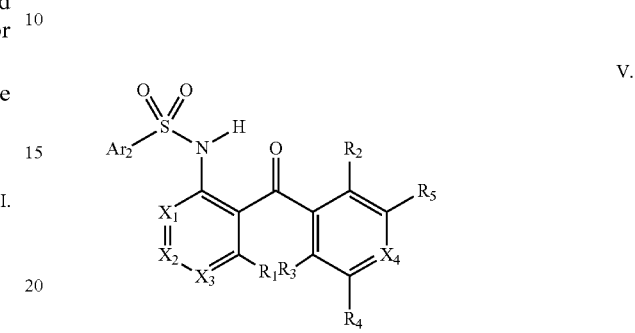

V.

In Structural Formula V, $X_4$ is CR, N or $N^+$—$O^-$; $X_1$, $X_2$, $X_3$, R, and $Ar_2$ are defined as in Structural Formula I; $R_1$, $R_2$, $R_3$, $R_4$, $R_5$, are, independently, H, an aliphatic group, a haloalkyl group, a halo, COOH, $NO_2$, or an alkoxy, a haloalkoxy.

In a more preferred embodiment, compounds of the invention are represented by Structural Formula VI.

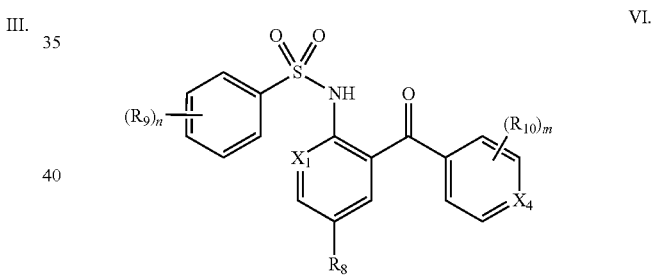

VI.

In Structural Formula $V_1$, $X_1$ is defined as in Structural Formula I; $X_4$ is defined as in Structural Formula V; $R_8$ is H or an electron withdrawing group; m and n are each, independently, 0 or an integer from 1 to 3; each $R_9$ is, independently, aliphatic group, haloalkyl, aryl, arylalkyl, alkoxy, cycloalkoxy, haloalkoxy, aryloxy, arylalkoxy, alkylthio, halo, nitro, cyano, hydroxy, $NR_{11}CO_2R_{12}$, $C(O)N(R_{11})_2$, $C(O)R_{12}$, $CO_2R_{12}$, $OC(O)N(R_{11})_2$, $OC(O)R_{12}$, $N(R_{11})_2$, or $NR_{11}C(O)R_{12}$; or two adjacent $R_9$ groups taken together with the atoms to which they are attached form a fused, saturated, unsaturated or partially unsaturated 5 to 7 membered ring having 0, 1, or 2 heteroatoms selected from N, O, and S; each $R_{10}$ is, independently, halo, aliphatic group, alkoxy, or haloalkyl; or two adjacent $R_{10}$ groups taken together with the atoms to which they are attached form a fused, saturated, unsaturated or partially unsaturated 5 to 7 membered ring having 0, 1 or 2 heteroatoms selected from N, O, and S; each $R_{11}$ is, independently, selected from H or an aliphatic group; and $R_{12}$ is an aliphatic group.

In another preferred embodiment, compounds of the invention are represented by Structural Formula VII.

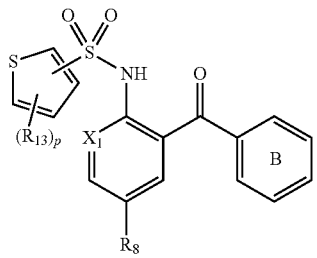

VII.

In Structural Formula VII, ring B is substituted or unsubstituted; $X_1$ is defined as in Structural Formula I; $R_8$ is defined as in Structural Formula VI; p is 0 or an integer from 1-3; and each $R_{13}$ is, independently, a halo or a substituted or unsubstituted heteroaryl.

In another preferred embodiment, compounds of the invention are represented by Structural Formula VIII.

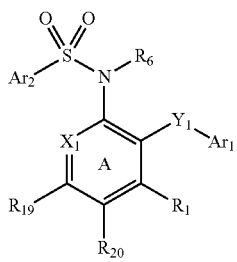

VIII.

In Structural Formula VIII, ring A, $Ar_1$, $Ar_2$, $X_1$, $R_1$, $R_6$ are defined as in Structural Formula I; $R_{19}$ and $R_{20}$ are defined as in Structural Formula IV; and $Y_1$ is S, O, S(O), or $S(O)_2$.

The present invention provides a method of inhibiting a CCR9 receptor by contacting the receptor with an effective amount of a compound of the present invention, and/or pharmaceutically acceptable salts, solvates and hydrates thereof.

In one embodiment, the invention provides a method of inhibiting CCR9-mediated homing of leukocytes in a subject by administering to the subject an effective amount of a compound of the present invention, and/or pharmaceutically acceptable salts, solvates and hydrates thereof. In a preferred embodiment, the method inhibits homing of leukocytes to mucosal tissue.

In another embodiment, the invention provides a method of treating a subject having a disease that is mediated by a CCR9 receptor, such as an inflammatory disease, for example Celiac's disease or an inflammatory bowel disease, by administering to the subject an effective amount of a compound of the present invention, and/or pharmaceutically acceptable salts, solvates and hydrates thereof.

The present invention provides a pharmaceutical composition having a pharmaceutically acceptable carrier and at least one compound of the present invention.

Chemokines and their associated receptors (e.g., TECK and CCR9, respectively) are proinflammatory mediators that promote recruitment and activation of multiple lineages of leukocytes and lymphocytes. Continuous release of chemokines at sites of inflammation mediates the ongoing migration of effector cells in chronic inflammation. CCR9 and its associated chemokine TECK, have been implicated in chronic inflammatory diseases, such as inflammatory bowel diseases. Small molecule inhibitors of the interaction between CCR9 and its ligands (e.g., TECK), such as the compounds of the invention, are useful for inhibiting harmful inflammatory processes triggered by receptor-ligand interactions and thus are useful for treating diseases mediated by CCR9, such as chronic inflammatory diseases.

DETAILED DESCRIPTION OF THE INVENTION

The term "aliphatic" as used herein means straight-chain, branched or cyclic $C_1$-$C_{12}$ hydrocarbons which are completely saturated or which contain one or more units of unsaturation but which are not aromatic. For example, suitable aliphatic groups include substituted or unsubstituted linear, branched or cyclic alkyl, alkenyl, alkynyl groups and hybrids thereof such as (cycloalkyl)alkyl, (cycloalkenyl)alkyl or (cycloalkyl)alkenyl. The terms "alkyl", "alkoxy", and "alkylthio", used alone or as part of a larger moiety includes both straight and branched chains containing one to twelve carbon atoms. The terms "alkenyl" and alkynyl" used alone or as part of a larger moiety shall include both straight and branched chains containing two to twelve carbon atoms. The term "cycloalkyl" used alone or as part of a larger moiety shall include cyclic $C_3$-$C_{12}$ hydrocarbons which are completely saturated or which contain one or more units of unsaturation, but which are not aromatic.

As used herein, aryl groups are carbocyclic aromatic ring systems (e.g. phenyl), fused polycyclic aromatic ring systems (e.g. naphthyl and anthracenyl) and aromatic ring systems fused to carbocyclic non-aromatic ring systems (e.g., 1,2,3,4-tetrahydronaphthyl) having six to about fourteen carbon atoms.

The terms "haloalkyl", "haloalkenyl" and "haloalkoxy" means alkyl, alkenyl or alkoxy, as the case may be, substituted with one or more halogen atoms. The term "halogen" means F, Cl, Br or I.

The term "aryl" used alone or as part of a larger moiety as in "aralkyl", "aralkoxy", or "aryloxyalkyl", refers to aromatic ring groups having five to fourteen members, such as phenyl, benzyl, phenethyl, 1-napthyl, 2-naphthyl, 1-anthracyl and 2-anthracyl. The term "aryl" also refers to rings that are optionally substituted. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenantriidinyl, or tetrahydronaphthyl, where the radical or point of attachment is on the aromatic ring.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or $NR_{18}$ (as in N-substituted pyrrolidinyl).

The term "heterocycle", as used herein includes non-aromatic ring systems having five to fourteen members, preferably five to ten, in which one or more ring carbons, preferably one to four, are each replaced by a heteroatom such as N, O, or S. Examples of heterocyclic rings include 3-1H-benzimidazol-2-one, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrorolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-pthalimidinyl, benzoxanyl, benzopyrrolidinyl, benzopiperidinyl, benzoxolanyl, benzothiolanyl, and benzothianyl. Also included within the scope of the term "heterocycle", as it is used herein, is a group in which a non-aromatic heteroatom-containing ring is fused to one or more aromatic or non-aromatic rings, such as in an indolinyl, chromanyl, phenantrhidinyl, or tetrahydroquinolinyl, where the radical or point of attachment is on the non-aromatic heteroatom-containing ring. The term "heterocycle", whether saturated or partially unsaturated, also refers to rings that are optionally substituted.

The term "heteroaryl", used alone or as part of a larger moiety as in "heteroaralkyl" or "heteroarylalkoxy", refers to heteroaromatic ring groups having five to fourteen members. Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 2-triazolyl, 5-triazolyl, 2-thienyl, 3-thienyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indolyl, isoindolyl, acridinyl, or benzoisazolyl. Also included within the scope of the term "heteroaryl", as it is used herein, is a group in which a heteroatomic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" also refers to rings that are optionally substituted. Preferred heteroaryl groups are thienyl, benzo(b)thienyl, pyrrolyl, indolyl, pyridyl, pyridazinyl, pyrimidinyl, pyrazinyl, furanyl, and benzo(b)furanyl. More preferred heteroaryl groups are pyridyl and thienyl.

An arylalkyl group, as used herein, is an aryl substituent that is linked to a compound by an alkyl group having from one to twelve carbon atoms.

An alkoxy group, as used herein, is a $C_1$-$C_{12}$ alkyl group that is connected to a compound via an oxygen atom. Examples of alkoxy groups include but are not limited to methoxy, ethoxy, propoxy, isopropoxy, and t-butoxy.

A cycloalkoxy group, as used herein, is a cyclic $C_3$-$C_{12}$ hydrocarbon which is attached to a compound via an oxygen. Cycloalkoxy groups include but are not limited to cyclopropoxy and cyclobutoxy.

A haloalkoxy, as used herein, is a haloalkyl group that is attached to a compound via an oxygen. A preferred haloalkoxy is trifluoromethoxy.

An aryloxy, as used herein, is an aryl group that is attached to a compound via an oxygen. A preferred aryloxy is phenoxy.

A arylalkoxy group, as used herein, is a arylalkyl group that is attached to a compound via an oxygen on the $C_1$-$C_{12}$ alkyl portion of the arylalkyl. A preferred arylalkoxy is phenylmethoxy.

An alkylthio group, as used herein, is a $C_1$-$C_{12}$ alkyl group that is connected to a compound via a sulfur atom.

A aliphatic carbonyl group, as used herein, is an aliphatic group that is connected to a compound via a carbonyl group. A preferred aliphatic carbonyl is acetyl.

A aliphatic ester group, as used herein, an aliphatic group that is connected to a compound via an ester linkage (i.e., —C(O)O-aliphatic group).

An electron withdrawing group is a group which causes a dipole moment in the direction of the group. Suitable electron withdrawing groups include but are not limited to halo (preferably chloro), haloalkyl (preferably trifluoromethyl), nitro, cyano, sulfonamido, sulfone, and sulfoxide.

An aryl (including aralkyl, aralkoxy, aryloxyalkyl and the like) or heteroaryl (including heteroaralkyl and heteroarylalkoxy and the like) may contain one or more substituents. Examples of suitable substituents include aliphatic groups, aryl groups, haloalkoxy groups, heteroaryl groups, halo, hydroxy, $OR_{14}$, $COR_{14}$, $COOR_{14}$, $NHCOR_{14}$, $OCOR_{14}$, benzyl, haloalkyl (e.g., trifluoromethyl and trichloromethyl), cyano, nitro, S(O), $S(O)_2$, $SO_3^-$, SH, $SR_{14}$, $NH_2$, $NHR_{14}$, $NR_{14}R_{15}$, $NR_6S(O)_2$—$R_7$, and COOH, wherein $R_{14}$ and $R_{15}$ are each, independently, an aliphatic group, a cycloalkyl, an aryl group, or an arylalky group. Other substituents for an aryl or heteroaryl group include —$R_{16}$, —$OR_{16}$, —$SR_{16}$, 1,2-methylene-dioxy, 1,2-ethylenedioxy, protected OH (such as acyloxy), phenyl (Ph), substituted Ph, —O(Ph), substituted —O(Ph), —$CH_2$(Ph), substituted —$CH_2CH_2$(Ph), substituted —$CH_2CH_2$(Ph), —$N(R_{16})_2$, —$NR_{16}CO_2R_{16}$, —$NR_{16}NR_{16}C(O)R_{16}$, —$NR_{16}R_{16}C(O)N(R_{16})_2$, —$NR_{16}NR_{16}CO_2R_{16}$, —$C(O)C(O)R_{16}$, —$C(O)CH_2C(O)R_{16}$, —$CO_2R_{16}$, —$C(O)R_{16}$, —$C(O)N(R_{16})_2$, —$OC(O)N(R_{16})_2$, —$S(O)_2R_{16}$, —$SO_2N(R_{16})_2$, —$S(O)R_{16}$, —$NR_{16}SO_2N(R_{16})_2$, —$NR_{16}SO_2R_{16}$, —$C(=S)N(R_{16})_2$, —$C(=NH)$—$N(R_{16})_2$, —$(CH_2)_yNHC(O)R_{16}$, —$(CH_2)_yNHC(O)CH(V$—$R_{16})(R_{16})$; wherein $R_{16}$ is hydrogen, a substituted or unsubstituted heteroaryl or heterocyclic ring, phenyl (Ph), substituted Ph, —O(Ph), substituted —O(Ph), —$CH_2$ (Ph), or substituted —$CH_2$ (Ph); y is 0-6; and V is a linker group. Preferred substituents on the aryl or heteroaryl group include halo, haloalkyl, sulfone, sulfoxide, nitro, cyano, alkyl group, alkoxy group, and alkylamino group. Examples of substituents on the aliphatic group or the phenyl ring include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl. Substituents for an aryl or a heteroaryl group include aryl groups (including a carbocyclic aryl group or a heteroaryl group), aliphatic groups, cycloalkyl groups, haloalkoxy groups, heteroaryl groups, hydroxy, $OR_{14}$, aldehyde, $COR_{14}$, $COOR_{14}$, $NHCOR_{14}$, $OCOR_{14}$, benzyl, haloalkyl (e.g., trifluoromethyl and trichloromethyl), halo, cyano, nitro, $SO_3^-$, SH, $SR_{14}$, $NH_2$, $NHR_{14}$, $NR_{14}R_{15}$, $NR_6S(O)_2$—$R_7$, or COOH, wherein $R_{14}$ and $R_{15}$ are each, independently, an aliphatic group, a cycloalkyl, an aryl group, or an arylalky group.

An aliphatic group or a heterocycle may contain one or more substituents. Examples of suitable substituents on the saturated carbon of an aliphatic group of a heterocycle include those listed above for an aryl or heteroaryl group and the following: =O, =S, =$NNHR_{17}$, =$NN(R_{17})_2$, =NNHC(O)$R_{17}$, =$NNHCO_2$(alkyl), =$NNHSO_2$(alkyl), or =$NR_{17}$, where each $R_{17}$ is independently selected from hydrogen, an unsubstituted aliphatic group or a substituted aliphatic group. Examples of substituents on the aliphatic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, thioalkyl, nitro, cyano, carboxy, alkoxycarbonyl, alkylcarbonyl, hydroxy, haloalkoxy, or haloalkyl.

Suitable substitutents on the nitrogen of a non-aromatic heterocycle or on an unsaturated nitrogen of a heteroaryl include —$R_{18}$, —$N(R_{18})_2$, —$C(O)R_{18}$, —$CO_2R_{18}$, —$C(O)C(O)R_{18}$, —$C(O)CH_2C(O)R_{18}$, —$SO_2R_{18}$, —$SO_2N(R_{18})_2$, —$C(=S)N(R_{18})_2$, —$C(=NH)$—$N(R_{18})_2$, and —$NR_{18}SO_2R_{18}$; wherein $R_{18}$ is hydrogen, an aliphatic group, a substituted aliphatic group, phenyl (Ph), substituted Ph, —O(Ph), substituted —O(Ph), —$CH_2$(Ph), or an unsubstituted heteroaryl or heterocyclic ring. Examples of substituents on the aliphatic group or the phenyl ring include amino, alkylamino, dialkylamino, aminocarbonyl, halogen, alkyl, alkylaminocarbonyl, dialkylaminocarbonyloxy, alkoxy, nitro, cyano, carboxy, alkoxycarbonyl, alkylcarbonyl, hydroxy, haloalkoxy, or haloalkyl.

The term "linker group" or "linker" means an organic moiety that connects two parts of a compound. Linkers are typically comprised of an atom, such as oxygen or sulfur, a unit, such as —NH—, —$CH_2$—, —C(O)—, or —C(O)NH—, or a chain of atoms, such as an alkylene chain. The molecular mass of a linker is typically in the range of about 14 to 200, preferably in the range of 14 to 96 with a length of up to about six atoms. Examples of linkers include a saturated or unsaturated $C_1$-$C_6$ alkylene chain which is substituted or unsubstituted, and wherein one or two saturated carbons of the chain are optionally replaced by —C(O)—, —C(O)C(O)—, —CONH—, —CONHNH—, —$CO_2$—, —OC(O)—, —$NHCO_2$—, —O—, —NHCONH—, —OC(O)NH—, —NHNH—, —NHCO—, —S—, —SO—, —$SO_2$—, —NH—, —$SO_2$NH—, or —$NHSO_2$.

It will be apparent to one skilled in the art that certain compounds of this invention may exist in tautomeric forms, all such tautomeric forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structure except for the replacement of a hydrogen by a deuterium or tritium, or the replacement of a carbon by a $^{13}$C- or $^{14}$C-enriched carbon are within the scope of this invention.

The compounds of the present invention have IC50s of less than 1 μm; less than 750 nm; preferably less than 500 nm; more preferably less than 250 nm; even more preferably less than 100 nm, most preferably less than 50 nm; and the most preferable less than 10 nm, e.g., less than 5 nm.

As used herein "mammalian CCR9" refers to naturally occurring or endogenous mammalian CCR9 proteins and to proteins having an amino acid sequence which is the same as that of a naturally occurring or endogenous corresponding mammalian CCR9 protein (e.g., recombinant proteins, synthetic proteins (i.e., produced using the methods of synthetic organic chemistry)). Accordingly, as defined herein, the term includes mature receptor protein, polymorphic or allelic variants, and other isoforms of a mammalian CCR9 (e.g., produced by alternative splicing or other cellular processes), and modified or unmodified forms of the foregoing (e.g., lipidated, glycosylated, unglycosylated). Naturally occurring or endogenous mammalian CCR9 proteins (see e.g., GenBank Accession Numbers NM_031200 and U45982 and Yu et al. (2000) *J. Immunol.* 164:1293-1305 which describe various forms of naturally occurring mammalian CCR9) include wild type proteins such as mature CCR9, polymorphic or allelic variants and other isoforms which occur naturally in mammals (e.g., humans, non-human primates). Such proteins can be recovered or isolated from a source which naturally produces mammalian CCR9, for example. Polymorphic, allelic, splice and other naturally occurring variants of mammalian CCR9 can be expressed in particular organs, tissues or cells and have altered properties (e.g., altered affinity for ligand (e.g. TECK)) and specialized biological function (e.g., T cell development, T cell recruitment). Naturally occurring or endogenous mammalian CCR9 proteins and proteins having the same amino acid sequence as a naturally occurring or endogenous corresponding mammalian CCR9, are referred to by the name of the corresponding mammal. For example, where the corresponding mammal is a human, the protein is designated as a human CCR9 protein (e.g., a recombinant human CCR9 produced in a suitable host cell).

As used herein "mammalian TECK" refers to naturally occurring or endogenous mammalian TECK proteins and to proteins having an amino acid sequence which is the same as that of a naturally occurring or endogenous corresponding mammalian TECK protein (e.g., recombinant proteins, synthetic proteins (i.e., produced using the methods of synthetic organic chemistry)). Accordingly, as defined herein, the term includes mature receptor protein, polymorphic or allelic variants, and other isoforms of a mammalian TECK (e.g., produced by alternative splicing or other cellular processes), and modified or unmodified forms of the foregoing (e.g., lipidated, glycosylated, unglycosylated). Naturally occurring or endogenous mammalian TECK proteins (see e.g., GenBank Accession Number U86358 and Vicari et al. (1997) *Immunity* 7:291-301 which describe naturally occurring mammalian TECK) include wild type proteins such as mature TECK, polymorphic or allelic variants and other isoforms which occur naturally in mammals (e.g., humans, non-human primates). Such proteins can be recovered or isolated from a source which naturally produces mammalian TECK, for example.

The term "pharmaceutically acceptable" means that the carrier, diluent, excipients and salt must be compatible with the other ingredients of the formulation, and not deleterious to the recipient thereof. Pharmaceutical formulations of the present invention are prepared by procedures known in the art using well known and readily available ingredients.

"Preventing" refers to reducing the likelihood that the recipient will incur or develop any of the pathological conditions described herein, for example inhibiting the onset of these symptoms.

"Treating" refers to eliminating or reducing the severity of a pathological condition described herein and/or eliminating, alleviating and/or reducing the symptoms of a pathological condition described herein.

Compounds of the invention can be used to treat a subject having an inflammatory disease. In one embodiment, the method is a method of inhibiting a CCR9 function in a subject. In particular embodiments, the method is a method of treating a subject having an inflammatory disease associated with mucosal tissue, such as Crohn's disease, colitis, or Celiac disease. In another embodiment, the method is a method of inhibiting CCR9-mediated homing of leukocytes in a subject. See Papadakis, et al., *Gastroenterology* (2001), 121:246-254 for a discussion of the relationship of CCR9 receptors to the above diseases or conditions.

In one embodiment, the compounds of the invention are represented by any one of Structural Formulas IX-XXIV:

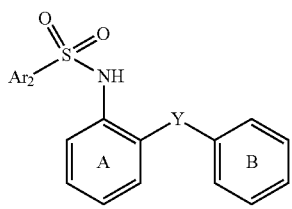 IX.
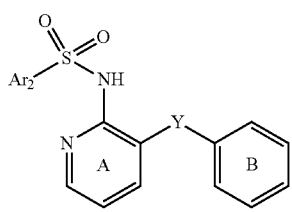 X.
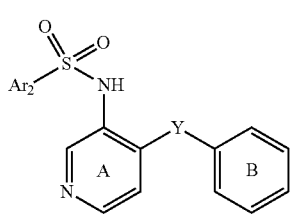 XI.
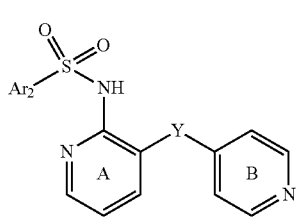 XII.
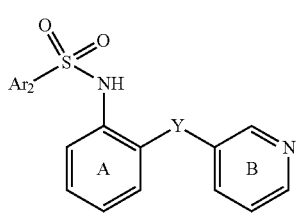 XIII.
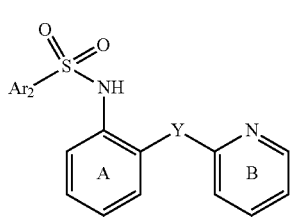 XIV.
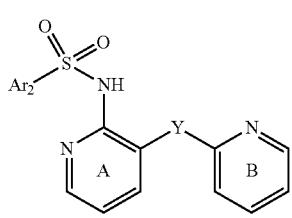 XV.
-continued
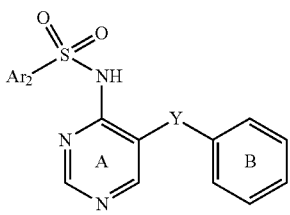 XVI.
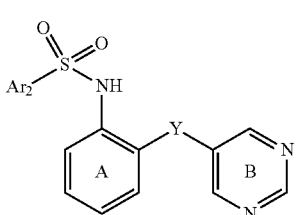 XVII.
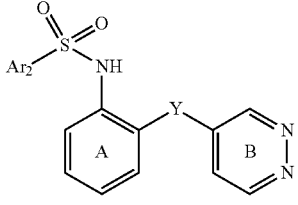 XVIII.
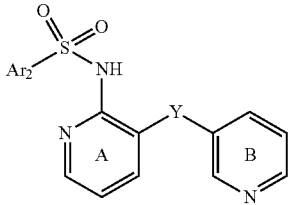 XIX.
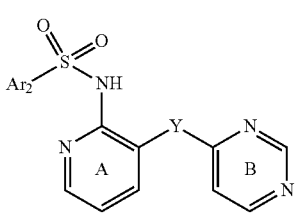 XX.
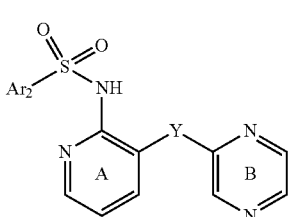 XXI.
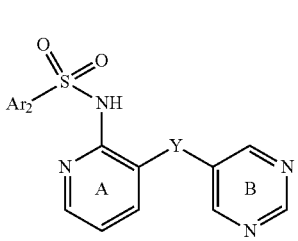 XXII.

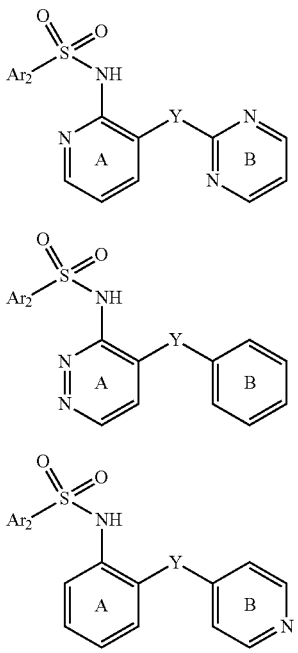

In Structural Formulas IX-XXV, $Ar_2$ and Y are defined as in Structural Formula I; and rings A and B are substituted or unsubstituted.

In another embodiment of the invention, compounds used in the method of the invention and in pharmaceutical compositions of the invention are represented by Structural Formula XXVI or XXVII:

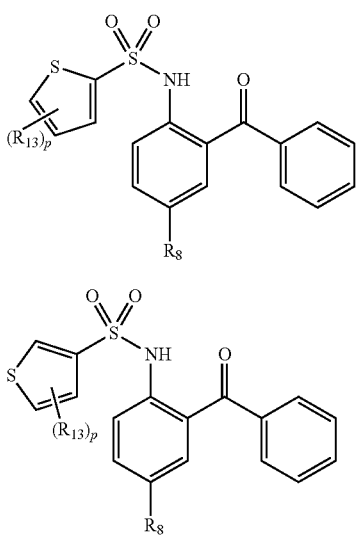

In Structural Formulas XXVI and XXVII, $R_8$ is defined as in Structural Formula V, and $R_{13}$ and p are defined as in Structural Formula VII.

In a first preferred embodiment of the invention, Y in Structural Formula I, or IX-XXIV is C=O.

In a second preferred embodiment, ring C in Structural Formula II or III or $Ar_2$ in Structural Formula I, IV, V or in any one of Structural Formulas IX-XXV is unsubstituted or substituted with one or more substituents selected from aliphatic group (including substituted aliphatic groups such as haloalkyl) aryl, arylalkyl, alkoxy (including cycloalkoxy and substituted alkoxy groups such as haloalkoxy), aryloxy, arylalkoxy, alkylthio, halo, nitro, cyano, S(O)-(aliphatic), $S(O)_2$-(aliphatic), $NR_{11}S(O)_2$-(aliphatic), $C(O)N(R_{11})_2$, $C(O)R_{12}$, $N(R_{11})_2$, $NR_{11}C(O)_2R_{12}$ and $NR_{11}C(O)R_{12}$, wherein $R_{11}$ for each occurrence is, independently, H or an aliphatic group, and $R_{12}$ is an aliphatic group. More preferred substitutents for ring C or $R_7$ are selected from an aliphatic group, an alkoxy, and a haloalkoxy.

In a third preferred embodiment, ring A in Structural Formula I or IV, or one or both rings A and B in Structural Formula II or III or in any one of Structural Formulas IX-XXV are, independently, substituted with a substituent selected from halo, aliphatic group, alkoxy, and haloalkyl.

In a fourth preferred embodiment, ring A in Structural Formula I, II, III, IV, V, VI, VII, VIII, or in any one of Structural Formulas IX-XXV is substituted with an electron withdrawing substituent para to the sulfonamide group.

In a fifth preferred embodiment of the invention, $X_3$ in Structural Formula V is $CR_{21}$, wherein $R_{21}$ is an electron withdrawing group. More preferably, $R_{21}$ is halo, nitro, aliphatic carbonyl, or trihalomethyl. Most preferably, $R_{21}$ is Cl, Br, or nitro.

In a sixth preferred embodiment of the invention, $Ar_2$ in Structural Formula I, IV, V, VIII or in any one of Structural Formulas IX-XXV is a substituted or unsubstituted phenyl, a substituted or unsubstituted naphthyl, a substituted or unsubstituted thienyl, or a substituted or unsubstituted thianaphthenyl. More preferably, $Ar_2$ is a substituted or unsubstituted phenyl or a substituted or unsubstituted thienyl.

In a seventh preferred embodiment of the invention, $R_9$ for each occurrence in Structural Formula VI is, independently, an aliphatic group, an alkoxy, or a haloalkoxy.

In an eighth preferred embodiment of the invention, $R_8$ in Structural Formula I, VI, VII, VIII, XXV and XXVI is a halo, nitro, alkylcarbonyl or trihaloalkyl. More preferably, $R_8$ is Cl, Br or $NO_2$.

In an ninth preferred embodiment of the invention, Y and $Ar_2$ in Structural Formula I and VIII or in any one of Structural Formulas IX-XXV are defined as in the first and the sixth preferred embodiments, respectively.

In a tenth preferred embodiment of the invention, $Ar_2$ Structural Formula V is defined as in the sixth preferred embodiments, and $X_3$ is defined as in the fifth preferred embodiment.

In an eleventh preferred embodiment, $X_4$ in Structural Formulas V or VI is an nitrogen oxide ($N^+$—$O^-$).

In a twelfth preferred embodiment, n is one in Structural Formula VI and $R_9$ is para to the sulfonamide substituent. More preferably, $R_9$ is as defined in seventh preferred embodiment.

In a thirteen preferred embodiment, m is one in Structural Formula VI and $R_{10}$ is meta to the carbonyl substituent.

In a fourteenth preferred embodiment, $R_6$ in Structural Formula I, IV, or VIII is H.

Specific examples of compounds used in the method of the invention and in pharmaceutical compositions of the invention include but are not limited to the compounds listed in Table 1. Pharmaceutically acceptable salts, solvates and hydrates of the compounds listed in Table 1 are also useful in the method of the invention and in pharmaceutical compositions of the invention.

TABLE 1

Specific compounds of the invention

| Example | Compound Name |
|---|---|
| 7 | N-[4-Chloro-2-(2-chloro-benzoyl)-phenyl]-4-nitro-benzenesulfonamide |
| 8 | Thiophene-2-sulfonic acid (2-benzoyl-4-chloro-phenyl)-amide |
| 9 | N-(2-Benzoyl-4-chloro-phenyl)-4-iodo-benzenesulfonamide |
| 10 | N-(2-Benzoyl-4-chloro-phenyl)-4-chloro-benzenesulfonamide |
| 11 | N-(2-Benzoyl-4-chloro-phenyl)-4-tert-butyl-benzenesulfonamide |
| 12 | N-(2-Benzoyl-4-chloro-phenyl)-4-propyl-benzenesulfonamide |
| 13 | N-(2-Benzoyl-4-chloro-phenyl)-4-ethyl-benzenesulfonamide |
| 14 | N-(2-Benzoyl-4-nitro-phenyl)-4-ethyl-benzenesulfonamide |
| 15 | N-(2-Benzoyl-4-chloro-phenyl)-4-isopropyl-benzenesulfonamide |
| 16 | N-(2-Benzoyl-4-bromo-phenyl)-4-ethyl-benzenesulfonamide |
| 17 | N-(2-Benzoyl-4-bromo-phenyl)-4-methoxy-benzenesulfonamide |
| 18 | N-(2-Benzoyl-4-bromo-phenyl)-4-isopropyl-benzenesulfonamide |
| 19 | 4-Ethyl-N-[4-nitro-2-(3-trifluoromethyl-benzoyl)-phenyl]-benzenesulfonamide |
| 20 | N-[4-Chloro-2-(3-methyl-benzoyl)-phenyl]-4-ethyl-benzenesulfonamide |
| 21 | N-(2-Benzoyl-4-bromo-phenyl)-4-chloro-benzenesulfonamide |
| 22 | N-(2-Benzoyl-4-chloro-phenyl)-4-ethoxy-benzenesulfonamide |
| 23 | N-(2-Benzoyl-4-chloro-phenyl)-4-propoxy-benzenesulfonamide |
| 24 | N-(2-Benzoyl-4-chloro-phenyl)-4-isopropoxy-benzenesulfonamide |
| 25 | N-(2-Benzoyl-4-chloro-phenyl)-4-butoxy-benzenesulfonamide |
| 26 | N-(2-Benzoyl-4-chloro-phenyl)-4-benzyloxy-benzenesulfonamide |
| 27 | N-(2-Benzoyl-4-chloro-phenyl)-4-phenoxy-benzenesulfonamide |
| 31 | N-(3-Benzoyl-5-chloro-pyridin-2-yl)-4-isopropoxy-benzenesulfonamide |
| 32 | N-[4-Chloro-2-(pyridine-4-carbonyl)-phenyl]-4-ethoxy-benzenesulfonamide |
| 33 | N-[4-Chloro-2-(pyridine-4-carbonyl)-phenyl]-4-isopropyl-benzenesulfonamide |
| 34 | N-[4-Chloro-2-(pyridine-4-carbonyl)-phenyl]-4-isobutyl-benzenesulfonamide |
| 35 | N-[5-Chloro-3-(pyridine-4-carbonyl)-pyridin-2-yl]-4-ethoxy-benzenesulfonamide |
| 36 | N-[5-Chloro-3-(pyridine-4-carbonyl)-pyridin-2-yl]-4-isopropoxy-benzenesulfonamide |
| 45 | N-(3-Benzoyl-5-trifluoromethyl-pyridin-2-yl)-4-isopropoxy-benzenesulfonamide |
| 46 | N-(2-Benzoyl-4-nitro-phenyl)-4-chloro-benzenesulfonamide |
| 47 | 5-Benzoyl-6-(4-isopropoxy-benzenesulfonylamino)-nicotinic acid |
| 48 | N-(2-Benzoyl-4-chloro-phenyl)-2-nitro-benzenesulfonamide |
| 49 | N-(3-Benzoyl-5-nitro-pyridin-2-yl)-4-isopropoxy-benzenesulfonamide |
| 50 | N-(5-Benzoyl-pyrimidin-4-yl)-4-isopropoxy-benzenesulfonamide |
| 51 | N-(3-Benzoyl-5-trifluoromethoxy-pyridin-2-yl)-4-isopropoxy-benzenesulfonamide |
| 52 | N-(5-Benzoyl-2-trifluoromethyl-pyrimidin-4-yl)-4-isopropoxy-benzenesulfonamide |
| 53 | N-(3-Benzoyl-5-chloro-pyridin-2-yl)-4-cyclopropoxy-benzenesulfonamide |
| 54 | N-(3-Benzoyl-5-chloro-pyridin-2-yl)-4-cyclobutyl-benzenesulfonamide |
| 55 | N-(3-Benzoyl-5-chloro-pyridin-2-yl)-4-tert-butoxy-benzenesulfonamide |
| 56 | N-(3-Benzoyl-5-chloro-pyridin-2-yl)-4-cyclopentyl-benzenesulfonamide |
| 57 | N-(3-Benzoyl-5-chloro-pyridin-2-yl)-4-isopropylsulfanyl-benzenesulfonamide |
| 58 | N-(3-Benzoyl-5-chloro-pyridin-2-yl)-4-isopropylamino-benzenesulfonamide |
| 59 | N-(3-Benzoyl-5-chloro-pyridin-2-yl)-4-cyclopropyl-benzenesulfonamide |
| 60 | N-(3-Benzoyl-5-chloro-pyridin-2-yl)-4-cyclohexyl-benzenesulfonamide |
| 61 | N-(3-Benzenesulfinyl-5-chloro-pyridin-2-yl)-4-isopropoxy-benzenesulfonamide |
| 62 | N-(3-Benzenesulfonyl-5-chloro-pyridin-2-yl)-4-isopropoxy-benzenesulfonamide |
| 63 | N-[4-Chloro-2-(pyrimidine-5-carbonyl)-phenyl]-4-isopropoxy-benzenesulfonamide |
| 64 | N-[4-Chloro-2-(pyridazine-4-carbonyl)-phenyl]-4-isopropoxy-benzenesulfonamide |
| 65 | N-[4-Chloro-2-(2-trifluoromethyl-pyrimidine-5-carbonyl)-phenyl]-4-isopropoxy-benzenesulfonamide |
| 66 | N-[4-Chloro-2-(6-trifluoromethyl-pyridazine-4-carbonyl)-phenyl]-4-isopropoxy-benzenesulfonamide |
| 67 | N-[4-Chloro-2-(2-trifluoromethyl-pyrimidine-5-carbonyl)-phenyl]-4-isopropoxy-benzenesulfonamide |
| 68 | N-[4-Chloro-2-(6-trifluoromethyl-pyridazine-4-carbonyl)-phenyl]-4-isopropoxy-benzenesulfonamide |
| 69 | N-(2-Benzoyl-4-nitro-phenyl)-4-isopropyl-benzenesulfonamide |
| 70 | N-(2-Benzoyl-4-nitro-phenyl)-4-isopropoxy-benzenesulfonamide |
| 71 | N-(2-Benzoyl-4-nitro-phenyl)-4-methoxy-benzenesulfonamide |
| 72 | N-(2-Benzoyl-4-chloro-phenyl)-4-trifluoromethoxy-benzenesulfonamide |
| 73 | 5-Oxazol-5-yl-thiophene-2-sulfonic acid (2-benzoyl-4-chloro-phenyl)-amide |
| 74 | N-[4-Chloro-2-(3-chloro-benzoyl)-phenyl]-4-methoxy-benzenesulfonamide |
| 75 | N-(2-Benzoyl-4-chloro-phenyl)-4-methoxy-benzenesulfonamide |
| 76 | N-[4-Chloro-2-(3-chloro-benzoyl)-phenyl]-4-ethyl-benzenesulfonamide |
| 77 | N-(2-Benzoyl-4-chloro-phenyl)-4-ethylamino-benzenesulfonamide |

TABLE 1-continued

Specific compounds of the invention

| Example | Compound Name |
|---|---|
| 78 | 5-(1-Methyl-5-trifluoromethyl-1H-pyrazol-3-yl)-thiophene-2-sulfonic acid (2-benzoyl-4-chloro-phenyl)-amide |
| 79 | N-(2-Benzoyl-4-iodo-phenyl)-4-isopropoxy-benzenesulfonamide |
| 80 | N-[4-Chloro-2-(3-fluoro-benzoyl)-phenyl]-4-methyl-benzenesulfonamide |
| 81 | N-[4-Chloro-2-(3-chloro-benzoyl)-phenyl]-4-isopropyl-benzenesulfonamide |
| 82 | N-(2-Benzoyl-4-chloro-phenyl)-4-nitro-benzenesulfonamide |
| 83 | N-(2-Benzoyl-4-chloro-phenyl)-4-diethylamino-benzenesulfonamide |
| 84 | N-(2-Benzoyl-4-fluoro-phenyl)-4-methoxy-benzenesulfonamide |
| 85 | 4-Chloro-N-[4-chloro-2-(pyridine-3-carbonyl)-phenyl]-benzenesulfonamide |
| 86 | N-(2-Benzoyl-4-bromo-phenyl)-4-methyl-benzenesulfonamide |
| 87 | N-(2-Benzoyl-4-chloro-phenyl)-4-bromo-benzenesulfonamide |
| 88 | N-[4-Chloro-2-(pyridine-3-carbonyl)-phenyl]-4-methoxy-benzenesulfonamide |
| 89 | N-(2-Benzoyl-4-chloro-phenyl)-4-dimethylamino-benzenesulfonamide |
| 90 | N-(2-Benzoyl-4-chloro-phenyl)-4-fluoro-benzenesulfonamide |
| 91 | 4-Chloro-N-[4-chloro-2-(2-fluoro-benzoyl)-phenyl]-benzenesulfonamide |
| 92 | N-[4-Chloro-2-(2-fluoro-benzoyl)-phenyl]-4-methoxy-benzenesulfonamide |
| 93 | Thiophene-3-sulfonic acid (2-benzoyl-4-chloro-phenyl)-amide |
| 94 | 5-Bromo-thiophene-2-sulfonic acid(2-benzoyl-4-chloro-phenyl)-amide |
| 95 | 5-Chloro-thiophene-2-sulfonic acid (2-benzoyl-4-chloro-phenyl)-amide |
| 96 | N-[4-Chloro-2-(2-fluoro-benzoyl)-phenyl]-4-nitro-benzenesulfonamide |
| 97 | N-[4-Chloro-2-(2-fluoro-benzoyl)-phenyl]-4-methyl-benzenesulfonamide |
| 98 | 4-Chloro-N-[4-chloro-2-(pyridine-2-carbonyl)-phenyl]-benzenesulfonamide |
| 99 | N-(2-Benzoyl-4-chloro-phenyl)-benzenesulfonamide |
| 100 | N-[4-(2-Benzoyl-4-chloro-phenylsulfamoyl)-phenyl]-acetamide |
| 101 | N-[4-Chloro-2-(pyridine-2-carbonyl)-phenyl]-4-methoxy-benzenesulfonamide |
| 102 | N-[4-Chloro-2-(pyridine-2-carbonyl)-phenyl]-4-methyl-benzenesulfonamide |
| 103 | N-(2-Benzoyl-4-chloro-phenyl)-4-cyano-benzenesulfonamide |
| 104 | 4,5-Dibromo-thiophene-2-sulfonic acid (2-benzoyl-4-chloro-phenyl)-amide |
| 105 | N-[4-Chloro-2-(pyridine-3-sulfonyl)-phenyl]-4-nitro-benzenesulfonamide |
| 106 | Naphthalene-2-sulfonic acid [4-chloro-2-(pyridine-3-carbonyl)-phenyl]-amide |
| 107 | N-(2-Benzoyl-4-chloro-phenyl)-3-bromo-benzenesulfonamide |
| 108 | N-(2-Benzoyl-4-chloro-phenyl)-4-methyl-3-nitro-benzenesulfonamide |
| 109 | N-[4-Chloro-2-(2-methoxy-benzoyl)-phenyl]-4-nitro-benzenesulfonamide |
| 110 | N-(2-Benzoyl-4-chloro-phenyl)-2-trifluoromethyl-benzenesulfonamide |
| 111 | 5-Chloro-3-methyl-benzo[b]thiophene-2-sulfonic acid (2-benzoyl-4-chloro-phenyl)-amide |
| 112 | N-(2-Benzoyl-phenyl)-4-nitro-benzenesulfonamide |
| 113 | 5-Isoxazol-3-yl-thiophene-2-sulfonic acid (2-benzoyl-4-chloro-phenyl)-amide |
| 114 | N-(2-Benzoyl-phenyl)-4-methyl-benzenesulfonamide |
| 115 | Benzo[b]thiophene-3-sulfonic acid (2-benzoyl-4-chloro-phenyl)-amide |
| 116 | N-(4-Chloro-2-phenylsulfanyl-phenyl)-4-isopropoxy-benzenesulfonamide |
| 117 | N-(2-Benzenesulfonyl-4-chloro-phenyl)-4-isopropoxy-benzenesulfonamide |
| 118 | N-[4-Chloro-2-(pyridine-4-carbonyl)-phenyl]-4-isopropoxy-benzenesulfonamide |
| 119 | N-[4-Chloro-2-(1-oxy-pyridine-4-carbonyl)-phenyl]-4-isopropoxy-benzenesulfonamide |
| 120 | 4-Isopropoxy-N-[2-(pyridine-4-carbonyl)-4-trifluoromethyl-phenyl]-benzenesulfonamide |
| 121 | 4-Ethoxy-N-[2-(pyridine-4-carbonyl)-4-trifluoromethyl-phenyl]-benzenesulfonamide |
| 122 | N-[5-Chloro-3-(3-fluoro-benzoyl)-pyridin-2-yl]-4-isopropyl-benzenesulfonamide |
| 123 | N-[5-Chloro-3-(3-fluoro-benzoyl)-pyridin-2-yl]-4-isopropoxy-benzenesulfonamide |
| 124 | N-[5-Chloro-3-(thiophene-2-carbonyl)-pyridin-2-yl]-4-isopropoxy-benzenesulfonamide |
| 125 | 5-Oxazol-5-yl-thiophene-2-sulfonic acid [5-chloro-3-(3-fluoro-benzoyl)-pyridin-2-yl]-amide |
| 126 | N-[3-(Benzofuran-2-carbonyl)-5-chloro-pyridin-2-yl]-4-isopropoxy-benzenesulfonamide |
| 127 | N-(2-Benzoyl-4-trifluoromethyl-phenyl)-4-isopropoxy-benzenesulfonamide |
| 128 | N-(3-Benzoyl-pyridin-4-yl)-4-isopropoxy-benzenesulfonamide |
| 129 | N-(3-Benzoyl-5-chloro-pyridin-2-yl)-4-isopropyl-benzenesulfonamide |
| 130 | N-(3-Benzoyl-5-nitro-pyridin-2-yl)-4-isopropoxy-benzenesulfonamide |
| 131 | 5-Oxazol-5-yl-thiophene-2-sulfonic acid (3-benzoyl-5-chloro-pyridin-2-yl)-amide |
| 132 | N-(2-Benzoyl-4-chloro-phenyl)-4-isopropylamino-benzenesulfonamide |
| 133 | N-(4-Benzoyl-pyridin-3-yl)-4-isopropyl-benzenesulfonamide |
| 134 | N-(4-Benzoyl-pyridin-3-yl)-4-isopropoxy-benzenesulfonamide |
| 135 | N-[4-Chloro-2-(pyridin-3-yloxy)-phenyl]-4-isopropyl-benzenesulfonamide |
| 136 | N-(2-Benzoyl-pyridin-3-yl)-4-isopropoxy-benzenesulfonarnide |
| 137 | N-[3-(3-Fluoro-benzoyl)-pyridin-2-yl]-4-isopropoxy-benzenesulfonamide |
| 138 | N-[4-Chloro-2-(pyridin-3-yloxy)-phenyl]-4-isopropoxy-benzenesulfonamide |
| 139 | 4-Isopropoxy-N-[3-(pyridine-4-carbonyl)-pyridin-4-yl]-benzenesulfonamide |
| 140 | 6-Isopropoxy-pyridine-3-sulfonic acid (3-benzoyl-5-chloro-pyridin-2-yl)-amide |
| 141 | 6-Isopropoxy-pyridine-3-sulfonic acid (2-benzoyl-4-chloro-phenyl)-amide |

TABLE 1-continued

Specific compounds of the invention

| Example | Compound Name |
|---|---|
| 142 | N-[4-Chloro-2-(pyridin-2-ylsulfanyl)-phenyl]-4-isopropyl-benzenesulfonamide |
| 143 | N-(2-Benzoyl-phenyl)-4-isopropoxy-benzenesulfonamide |

The structural formulas of Examples 7-27, 31-36, and 116-119 of Table 1 are shown in the Examples section. Examples 45-143 (Examples 116-119 are also included below) of Table 1 have the following structural formulas:

45.
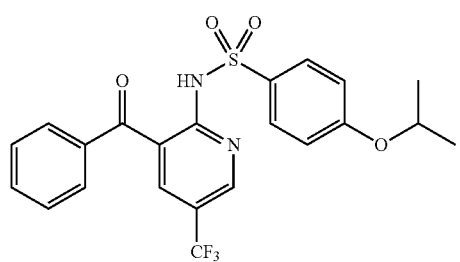

46.
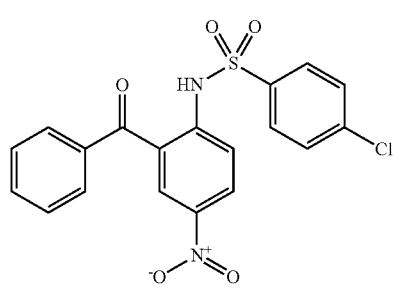

47.
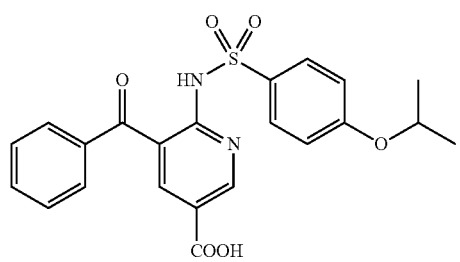

48.
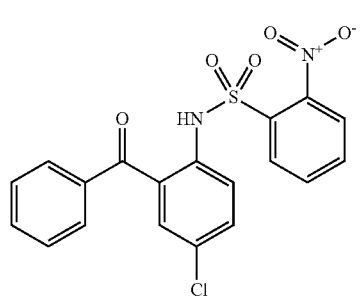

-continued

49.
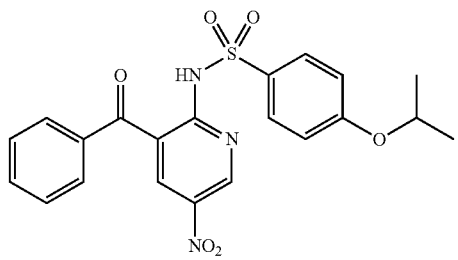

50.
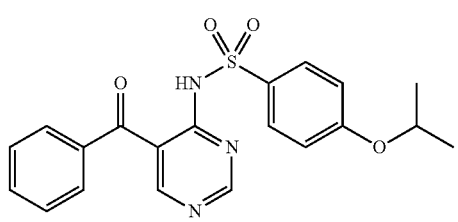

51.
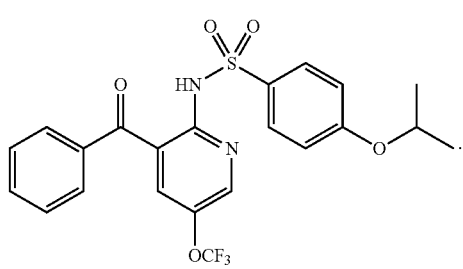

52.
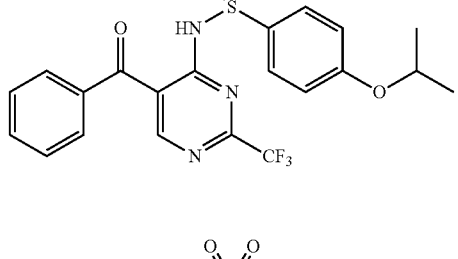

53.
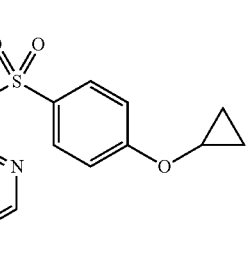

54.
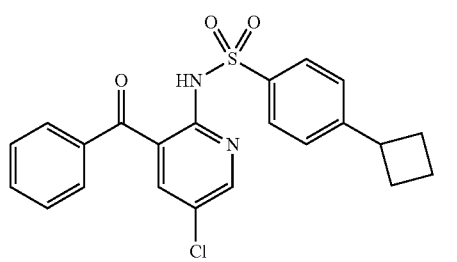
55.
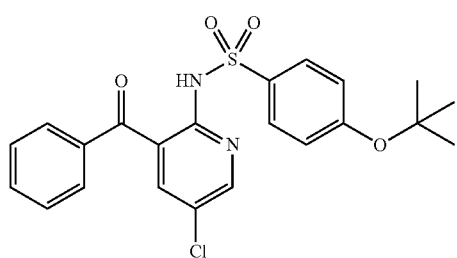
56.
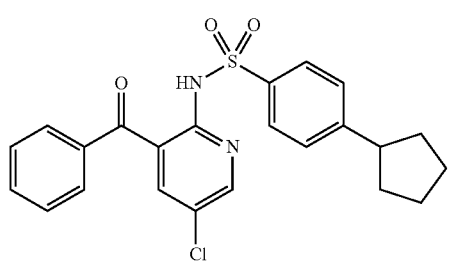
57.
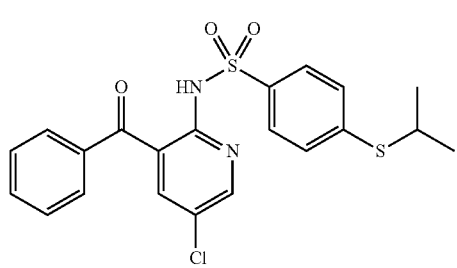
58.
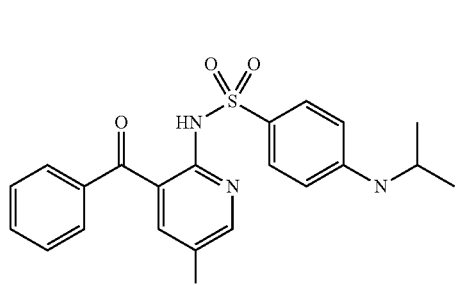
59.
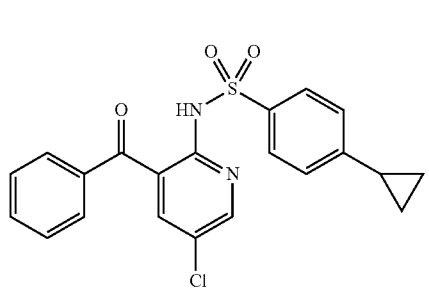
60.
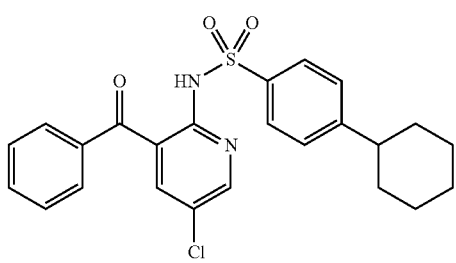
61.
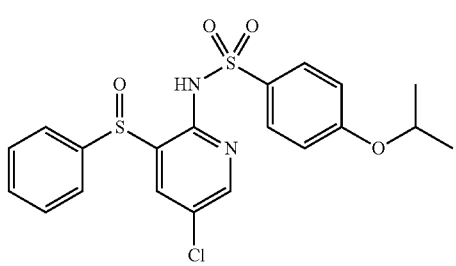
62.
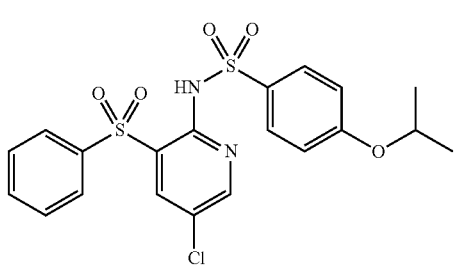
63.
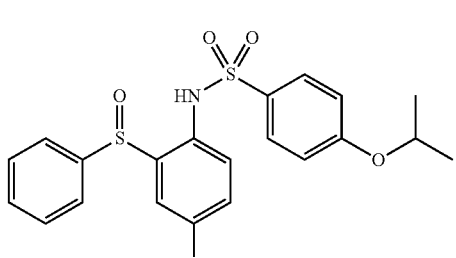
64.
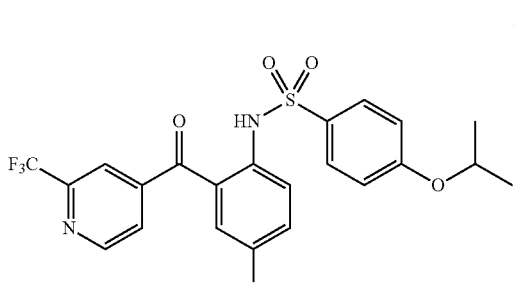
65.
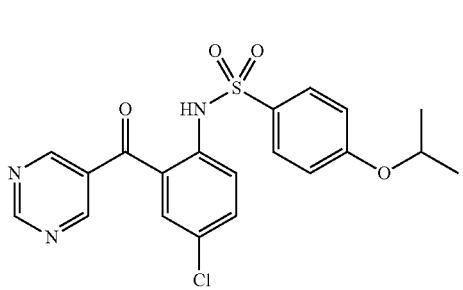

66. 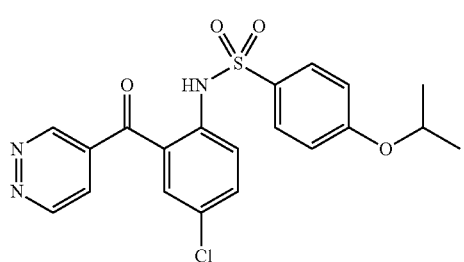
67. 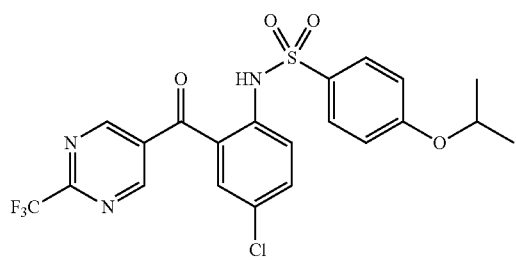
68. 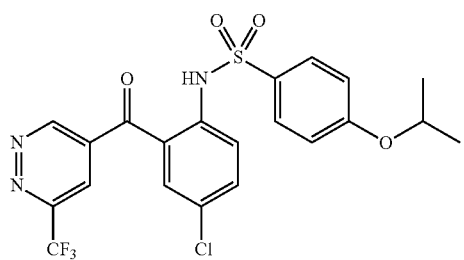
69. 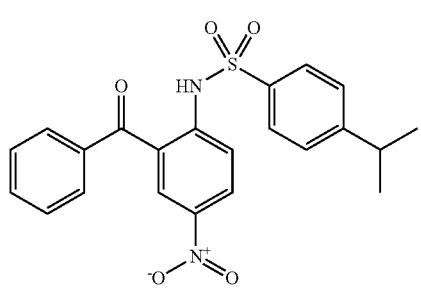
70. 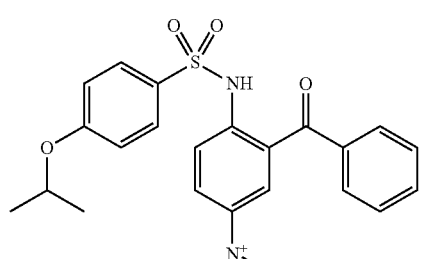
71. 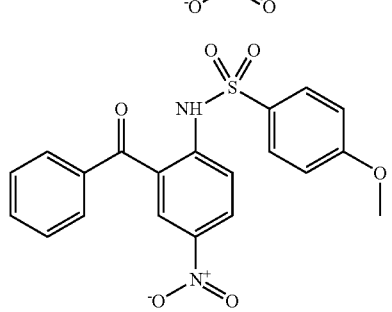
72. 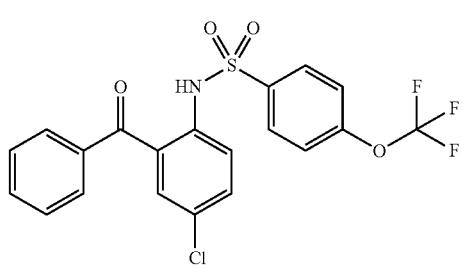
73. 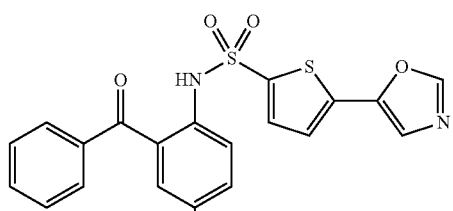
74. 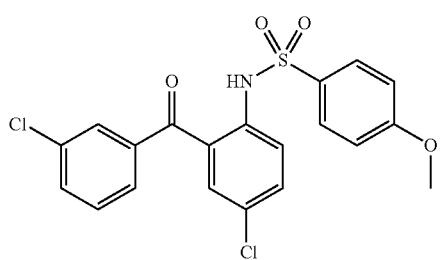
75. 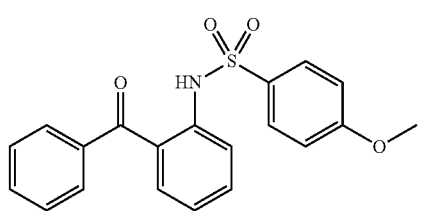
76. 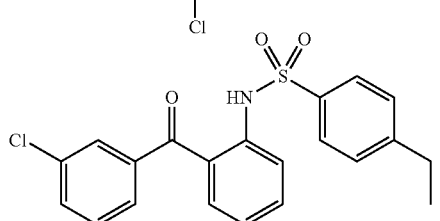
77. 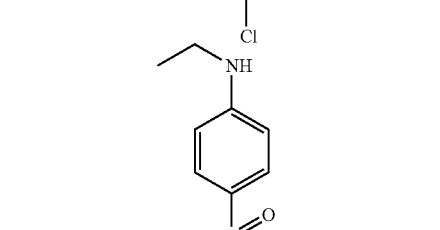
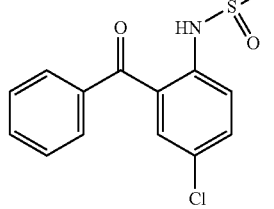

78. 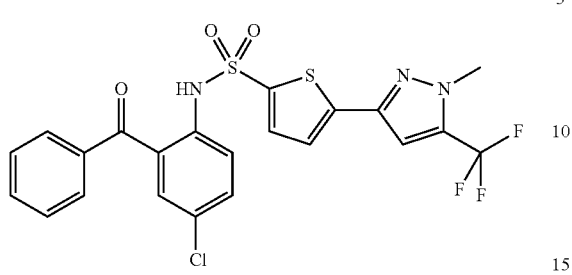
79. 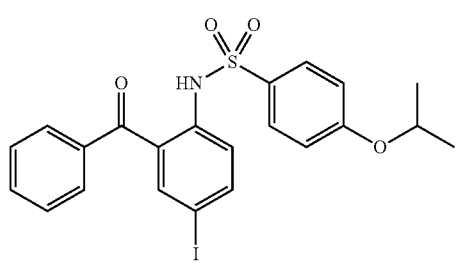
80. 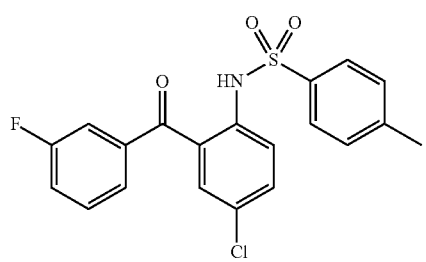
81. 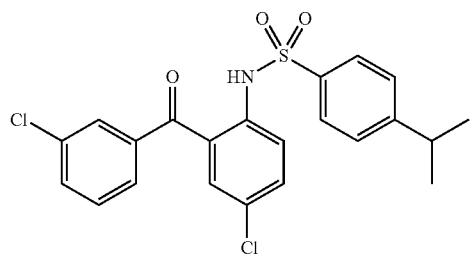
82. 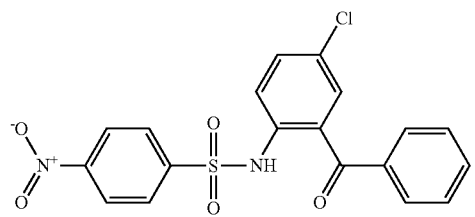
83. 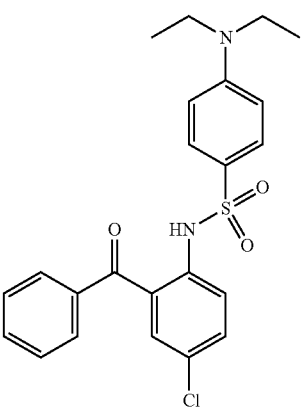
84. 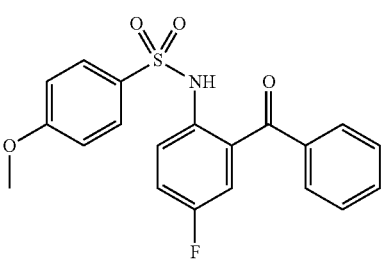
85. 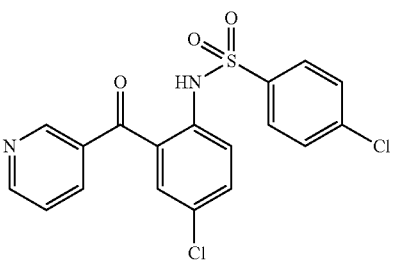
86. 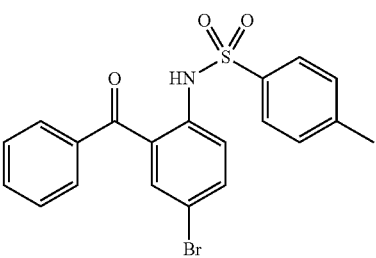
87. 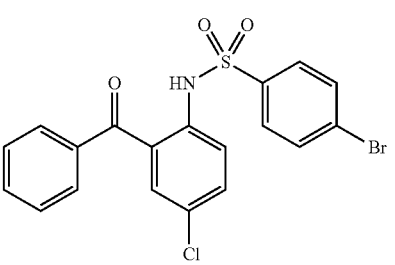

88.
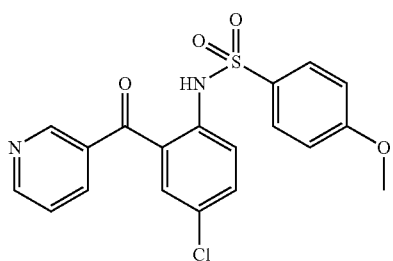
89.
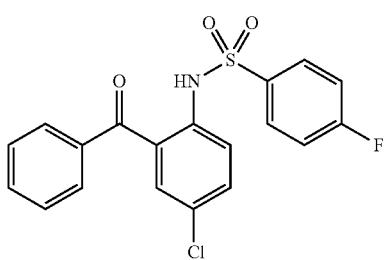
90.
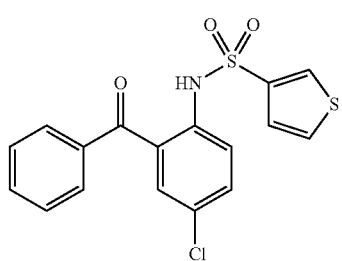
91.
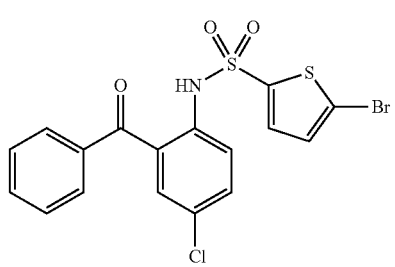
92.
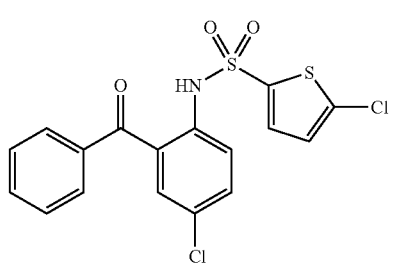
93.
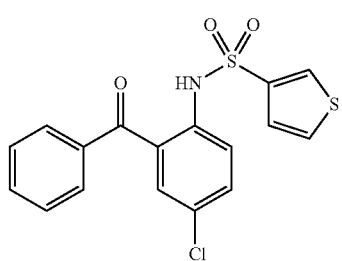
94.
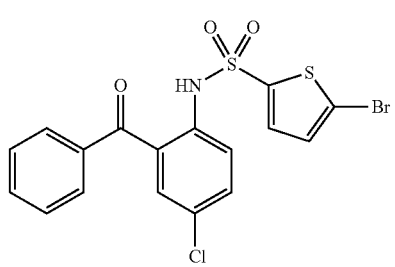
95.
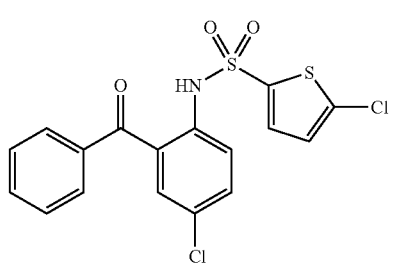
96.
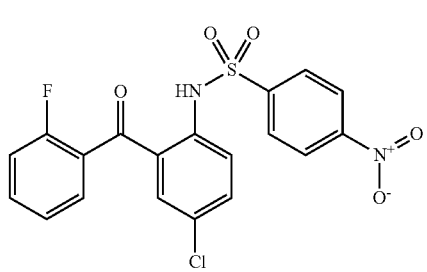
97.
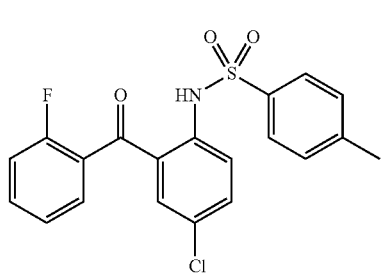
98.
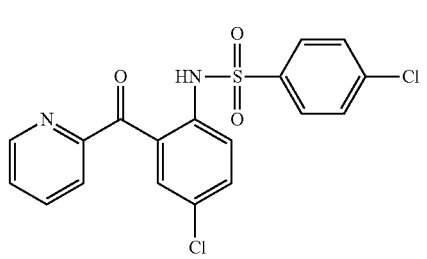

99. 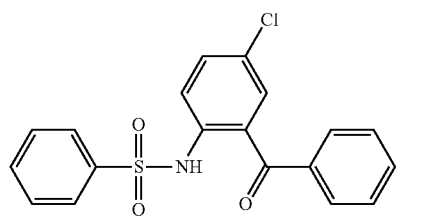
100. 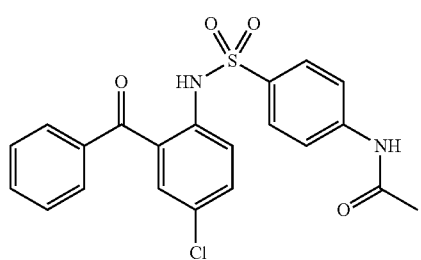
101. 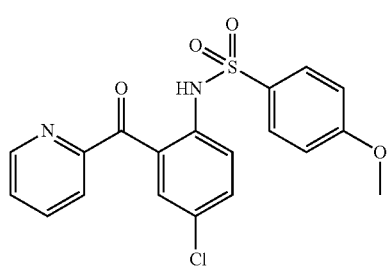
102. 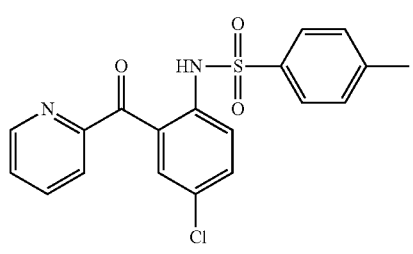
103. 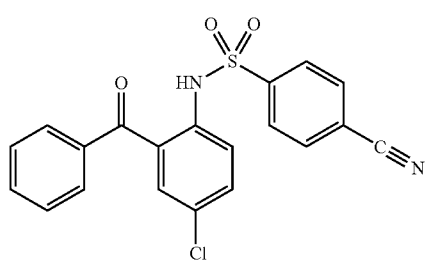
104. 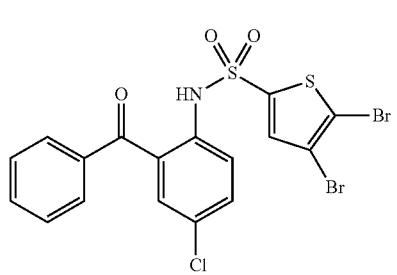
105. 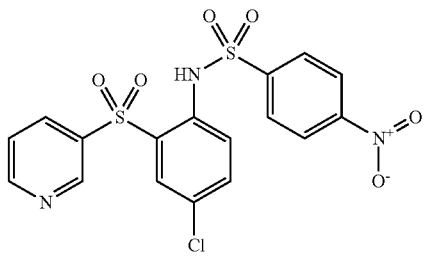
106. 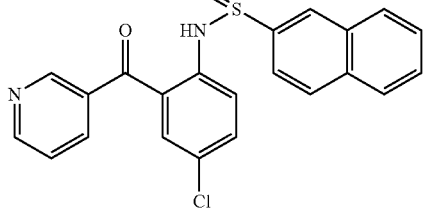
107. 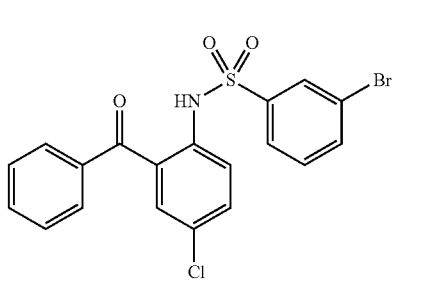
108. 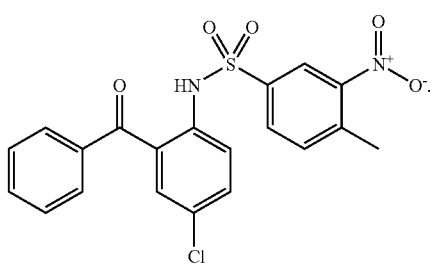
109. 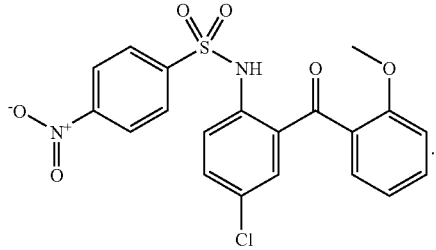
110. 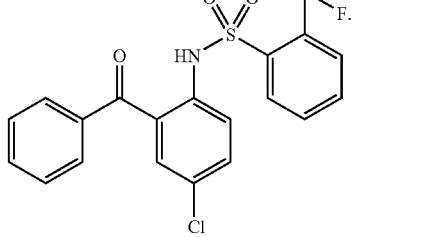

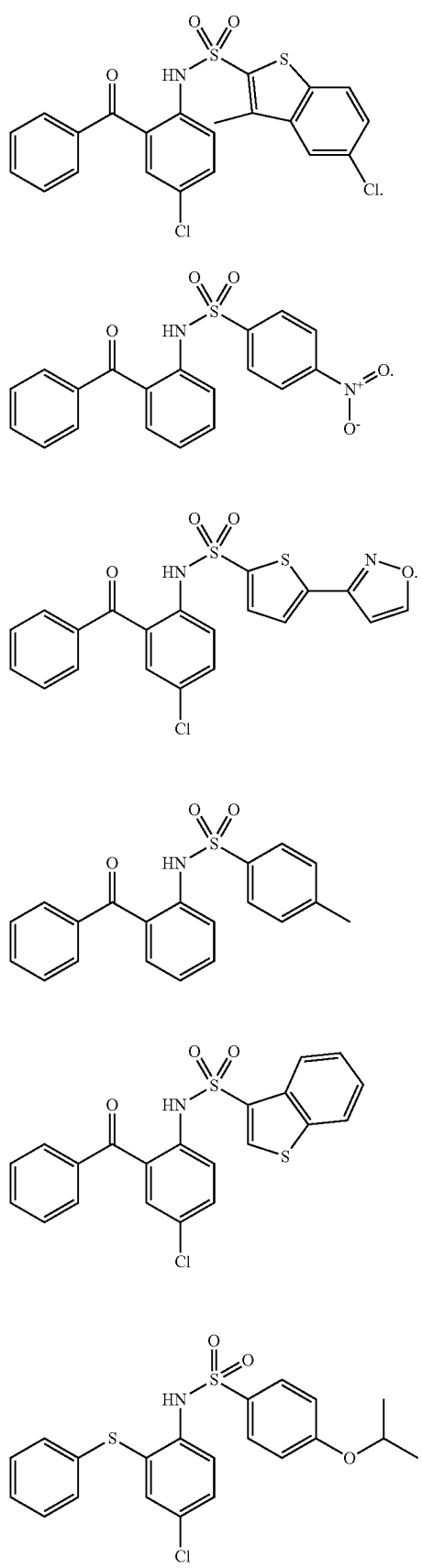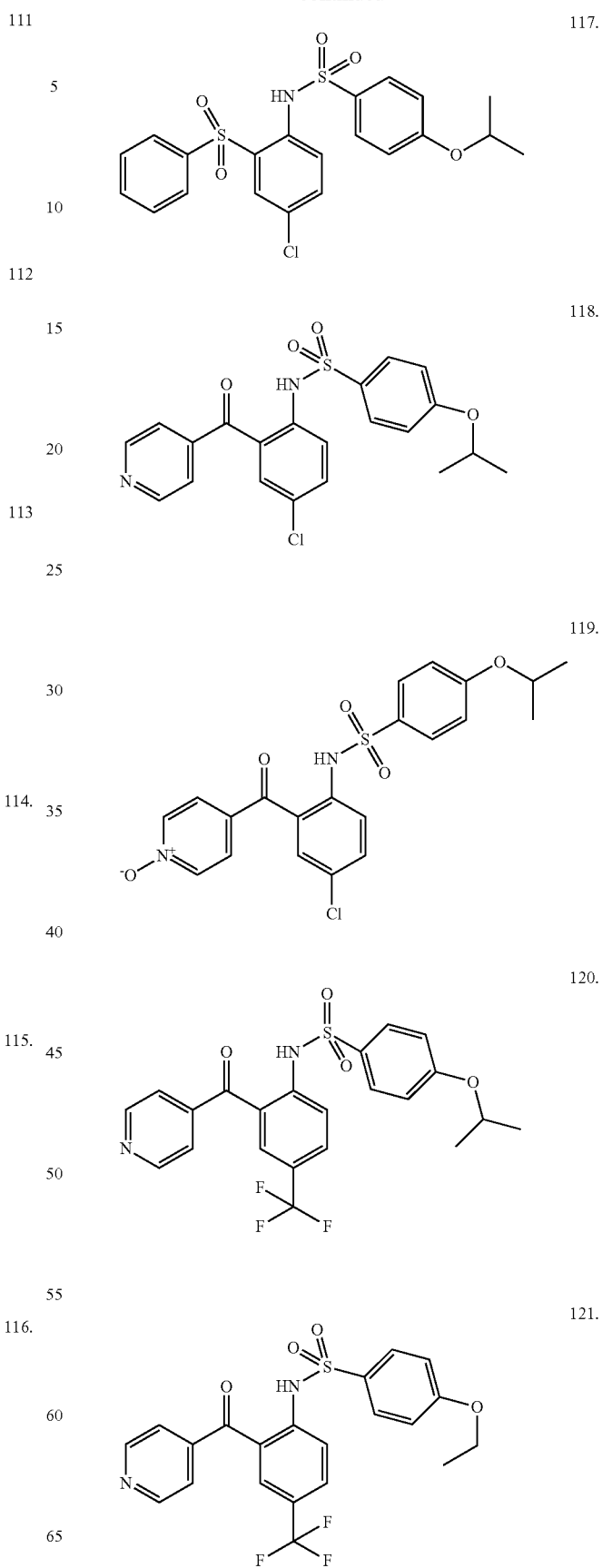

122.
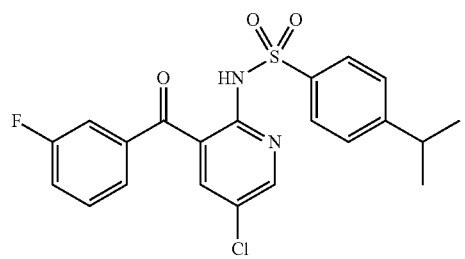
123.
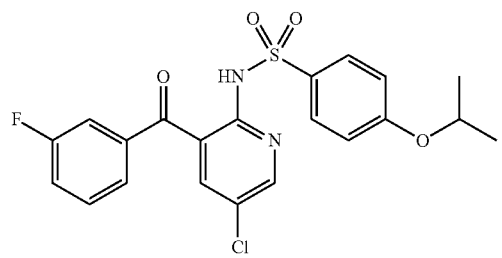
124.
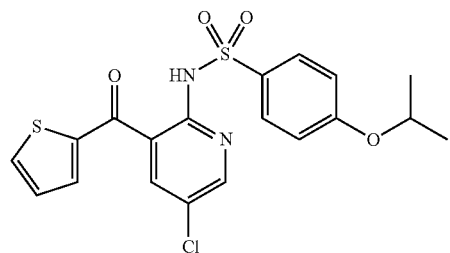
125.
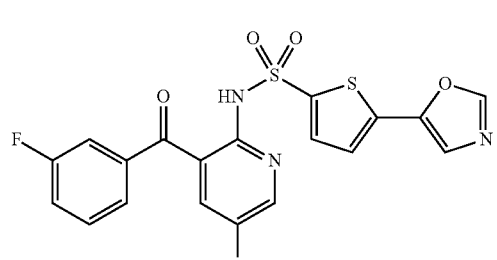
126.
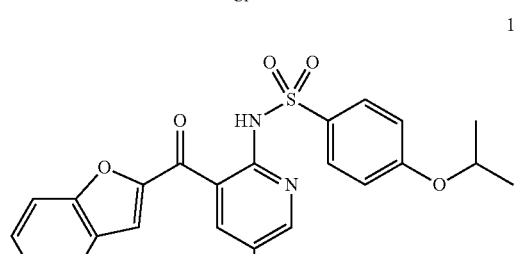
127.
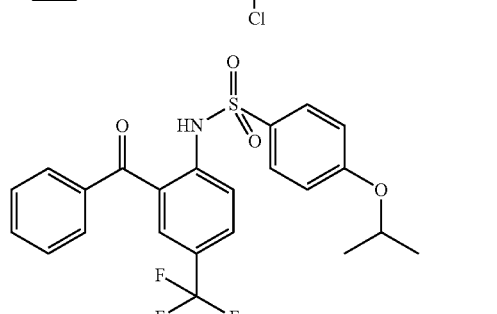
128.
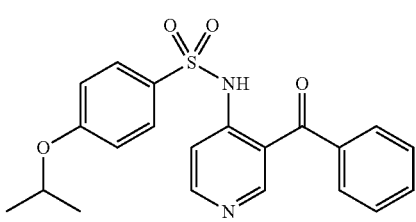
129.
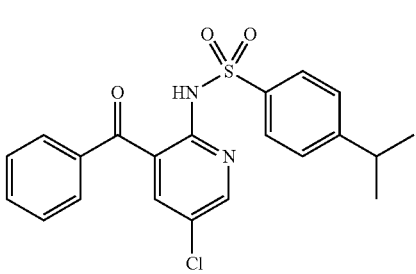
130.
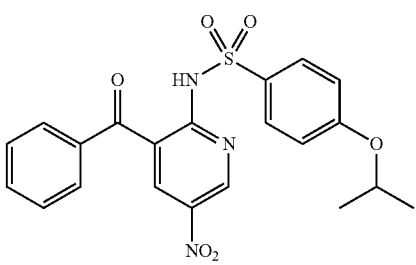
131.
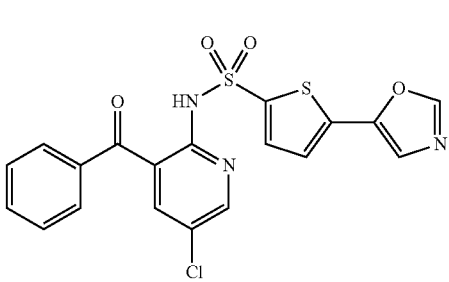
132.
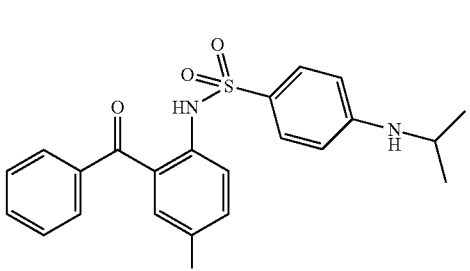
133.
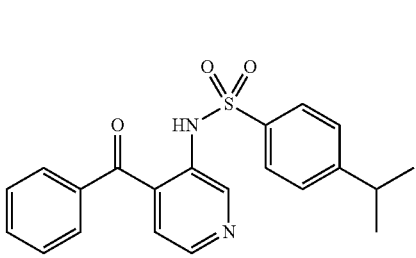

134.
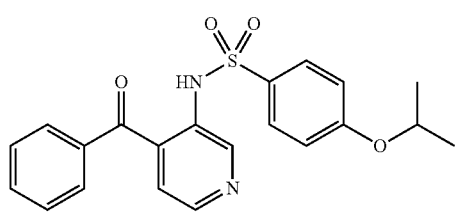

135.
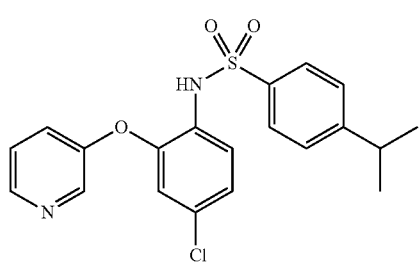

136.
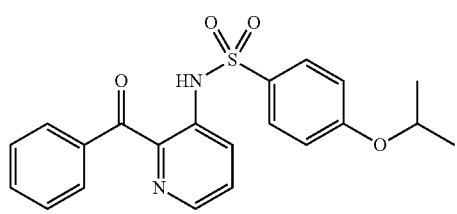

137.
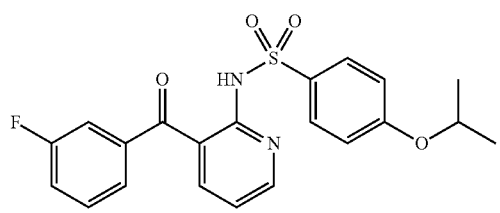

138.
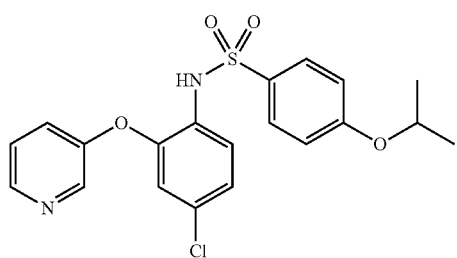

139.
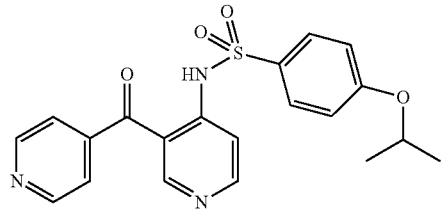

140.
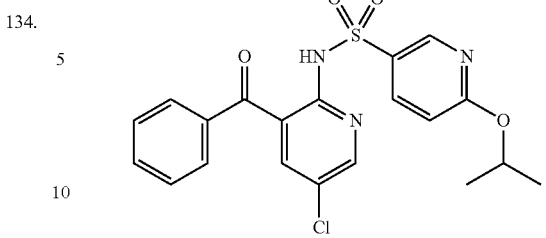

141.
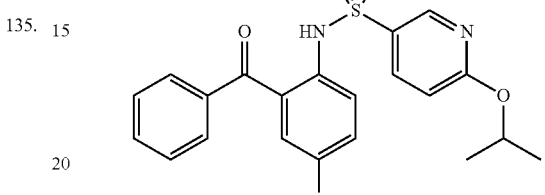

142.
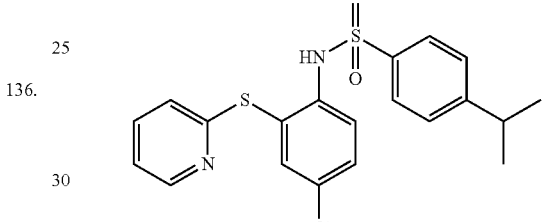

143.
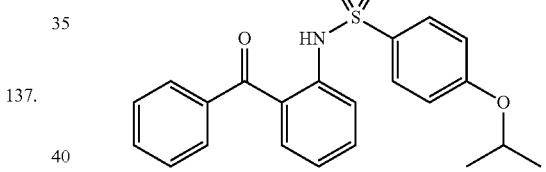

The following compounds are preferred compounds for use in the method of the invention:

N-(2-Benzoyl-4-chlorophenyl)-4-ethyl-benzenesulfonamide;
N-(2-Benzoyl-4-nitrophenyl)-4-ethyl-benzenesulfonamide;
N-(2-Benzoyl-4-bromophenyl)-4-isopropyl-benzenesulfonamide;
N-(2-Benzoyl-4-chlorophenyl)-4-ethoxy-benzenesulfonamide;
N-(2-Benzoyl-4-chlorophenyl)-4-isopropoxy-benzenesulfonamide;
N-(3-Benzoyl-5-chloro-pyridin-2-yl)-4-isopropoxy-benzenesulfonamide;
N-[4-Chloro-2-(pyridine-4-carbonyl)-phenyl]-4-ethoxy-benzenesulfonamide;
N-[4-Chloro-2-(pyridine-4-carbonyl)-phenyl]-4-isopropyl-benzenesulfonamide;
N-[4-Chloro-2-(pyridine-4-carbonyl)-phenyl]-4-isobutyl-benzenesulfonamide;
N-(3-Benzoyl-5-nitro-pyridin-2-yl)-4-isopropoxy-benzenesulfonamide;
N-[4-Chloro-2-(pyrimidine-5-carbonyl)-phenyl]-4-isopropoxy-benzenesulfonamide;
N-(2-Benzoyl-4-nitrophenyl)-4-isopropyl-benzenesulfonamide;

N-(2-Benzoyl-4-nitrophenyl)-4-isopropoxy-benzene-sulfonamide;
N-(4-Chloro-2-phenylsulfanyl-phenyl)-4-isopropoxy-benzenesulfonamide;
N-(2-Benzenesulfonyl-4-chloro-phenyl)-4-isopropoxy-benzenesulfonamide;
N-[4-Chloro-2-(pyridine-4-carbonyl)-phenyl]-4-isopropoxy-benzenesulfonamide;
N-[4-Chloro-2-(1-oxy-pyridine-4-carbonyl)-phenyl]-4-isopropoxy-benzenesulfonamide;
4-Ethoxy-N-[2-(pyridine-4-carbonyl)-4-trifluoromethyl-phenyl]-benzenesulfonamide;
N-[5-Chloro-3-(3-fluoro-benzoyl)-pyridin-2-yl]-4-isopropoxy-benzenesulfonamide;
N-(2-Benzoyl-4-trifluoromethyl-phenyl)-4-isopropoxy-benzenesulfonamide;
N-(3-Benzoyl-pyridin-4-yl)-4-isopropoxy-benzenesulfonamide;
N-(3-Benzoyl-5-chloro-pyridin-2-yl)-4-isopropyl-benzenesulfonamide;
5-Oxazol-5-yl-thiophene-2-sulfonic acid (3-benzoyl-5-chloro-pyridin-2-yl)-amide;
6-Isopropoxy-pyridine-3-sulfonic acid (3-benzoyl-5-chloro-pyridin-2-yl)-amide;
6-Isopropoxy-pyridine-3-sulfonic acid (2-benzoyl-4-chloro-phenyl)-amide;
N-[4-Chloro-2-(pyridin-2-ylsulfanyl)-phenyl]-4-isopropyl-benzenesulfonamide; and pharmaceutically acceptable salts, solvates, or hydrates thereof.

Models of Inflammation

In vivo models of inflammation are available which can be used to assess the efficacy of compounds of the invention. For example, leukocyte infiltration upon intradermal injection of a chemokine and compound of the invention into a suitable animal, such as rabbit, mouse, rat, guinea pig or primate (e.g., rhesus macaque) can be monitored (see e.g., Van Damme, J. et al., *J. Exp. Med.*, 176: 59-65 (1992); Zachariae, C. O. C. et al., *J. Exp. Med.* 171: 2177-2182 (1990); Jose, P. J. et al., *J. Exp. Med.* 179: 881-887 (1994)). In one embodiment, skin biopsies are assessed histologically for infiltration of leukocytes (e.g., CCR9$^+$ T cells). In another embodiment, labeled cells (e.g., stably transfected cells expressing a mammalian CCR9, labeled with $^{111}$In for example) capable of chemotaxis and extravasation are administered to the animal. For example, compound of the invention to be assessed which binds a mammalian CCR9 can be administered, either before, simultaneously with or after a CCR9 ligand or agonist (e.g., TECK) is administered to the test animal. A decrease of the extent of infiltration in the presence of the compound of the invention as compared with the extent of infiltration in the absence of said compound is indicative of inhibition.

As described herein, CCR9 is selectively expressed on memory lymphocytes which home to mucosal sites (e.g., CLA$^{-ve}$ α4β7$^{hi}$ CD4$^+$ lymphocytes). Thus, animal models of inflammatory diseases of the mucosa (e.g., respiratory tract, urogenital tract, alimentary canal and associated organs and tissues (e.g., pancreas, liver, gall bladder)) can be used to assess the therapeutic efficacy of CCR9 inhibiting compounds. For example, the therapeutic efficacy of a compound of the invention can be studied in the cotton-top tamarin model of inflammatory bowel disease (Podolsky, D. K., et al., *J. Clin. Invest.* 92:372-380 (1993)). The CD45RB$^{Hi}$/SCID model provides a mouse model with similarity to both Crohn's disease and ulcerative colitis (Powrie, F. et al., *Immunity*, 1: 553-562 (1994)). Therapeutic efficacy in this model can be assessed, for example, by using parameters such as inhibition of recruitment of $^{111}$In-labeled cells to the colon and reduction in the number of CD4$^+$ T lymphocytes in the lamina propria of the large intestine after administration (e.g., intravenous (i.v.), intraperitoneally (i.p.) and per oral (p.o.)) of a compound.

Methods of Therapy

Inhibition of at least one function characteristic of a mammalian CCR9 protein according to the present invention provides an effective and selective way of inhibiting receptor-mediated functions. Once lymphocytes are recruited to a site, other leukocyte types, such as monocytes, may be recruited by secondary signals. Thus, compounds which can inhibit CCR9 function (e.g., compounds of the invention) can be used to inhibit leukocyte function (e.g., leukocyte infiltration including recruitment and/or accumulation).

In one aspect, the present invention provides a method of inhibiting an inflammatory response in a subject, comprising administering an effective amount of a compound of the invention which inhibits mammalian CCR9 function to a subject in need of such therapy. In one embodiment, an effective amount of a compound which inhibits one or more functions of a mammalian CCR9 protein (e.g., a human CCR9) is administered to a subject to inhibit (i.e., reduce or prevent) inflammation. Preferred compounds of the invention, inhibit an inflammatory response in a subject by inhibiting (i.e., reduce or prevent) binding of ligand (e.g. TECK) to CCR9. As a result, one or more inflammatory processes, such as leukocyte emigration, chemotaxis, exocytosis (e.g., of enzymes) or inflammatory mediator release, is inhibited. For example, leukocytic infiltration of inflammatory sites (e.g., in a inflamed mucus membrane (e.g., colon, small intestine)) can be inhibited according to the present method. In another embodiment, an effective amount of a compound of the invention which inhibits one or more functions of a mammalian CCR9 protein (e.g., a human CCR9) is administered to a subject to inhibit (i.e., reduce or prevent) CCR9-mediated homing of leukocytes. In particular embodiments, an effective amount of a compound which binds to human CCR9 and/or an effective amount of a compound which binds to human TECK is administered to a subject in need thereof.

Thus, the invention relates to a method of treating a subject having an inflammatory disease, comprising administering an effective amount of a compound of the invention that antagonizes CCR9 function. In a particular embodiment, the subject has an inflammatory bowel disease, such as Crohn's disease or colitis. Treatment includes therapeutic or prophylactic treatment. Treatment, in accordance with the method, can prevent disease or reduce the severity of disease in whole or in part.

The invention also relates to a method of inhibiting CCR9-mediated homing of leukocytes in a subject, comprising administering an effective amount of a compound of the invention that antagonizes CCR9 function, for example, the horning of leukocytes to mucosal sites can be inhibited. Immigration of circulating leukocytes into organs or tissue (e.g., intestine) and/or local recruitment of lymphocytes within an organ or tissue (e.g., IEL, LPL) can be inhibited in accordance with the method.

The term "subject" is defined herein to include animals such as mammals, including, but not limited to, primates (e.g., humans), cows, sheep, goats, horses, dogs, cats, rabbits, guinea pigs, rats, mice or other bovine, ovine, equine, canine, feline, rodent or murine species. A "subject in need of treatment to inhibit CCR9 function" is a subject in whom a beneficial therapeutic or prophylactic effect can be achieved by inhibiting CCR9 function. Examples include subjects with one of the diseases or conditions described herein.

Diseases and conditions associated with inflammation and/or infection can be treated using the methods described herein. In a preferred embodiment, the disease or condition is one in which the actions of lymphocytes, particularly lymphocytes which home to mucosal tissues, are to be inhibited or promoted for therapeutic (including prophylactic) purposes. In a particularly preferred embodiment, the inflammatory disease or condition is a T cell-mediated disease or condition.

Examples of inflammatory diseases associated with mucosal tissues which can be treated according to the present method include mastitis (mammary gland), vaginitis, cholecystitis, cholangitis or pericholangitis (bile duct and surrounding tissue of the liver), chronic bronchitis, chronic sinusitis, asthma, and graft versus host disease (e.g., in the gastrointestinal tract). As seen in Crohn's disease, inflammation often extends beyond the mucosal surface, accordingly chronic inflammatory diseases of the lung which result in interstitial fibrosis, such as interstitial lung diseases (ILD) (e.g., idiopathic pulmonary fibrosis, or ILD associated with rheumatoid arthritis, or other autoimmune conditions), hypersensitivity pneumonitis, collagen diseases, sarcoidosis, and other idiopathic conditions can be amenable to treatment. Pancreatitis and insulin-dependent diabetes mellitus are other diseases which can be treated using the present method.

In a particularly preferred embodiment, diseases which can be treated accordingly include inflammatory bowel disease (IBD), such as ulcerative colitis, Crohn's disease, ileitis, Celiac disease, nontropical Sprue, enteritis, enteropathy associated with seronegative arthropathies, microscopic or collagenous colitis, eosinophilic gastroenteritis, or pouchitis resulting after proctocolectomy, and ileoanal anastomosis.

Additional diseases or conditions, including chronic diseases, of humans or other species which can be treated with compounds of the invention that inhibit of CCR9 function, include, but are not limited to:

inflammatory or allergic diseases and conditions, including systemic anaphylaxis or hypersensitivity responses, drug allergies (e.g., to penicillin, cephalosporins), insect sting allergies; psoriasis and inflammatory dermatoses such as dermatitis, eczema, atopic dermatitis, allergic contact dermatitis, urticaria; vasculitis (e.g., necrotizing, cutaneous, and hypersensitivity vasculitis); spondyloarthropathies; scleroderma; respiratory allergic diseases such as asthma, allergic rhinitis;

autoimmune diseases, such as arthritis (e.g., rheumatoid arthritis, psoriatic arthritis), multiple sclerosis, systemic lupus erythematosus, myasthenia gravis, juvenile onset diabetes, glomerulonephritis and other nephritides, autoimmune thyroiditis, Behcet's disease;

graft rejection (e.g., in transplantation), including allograft rejection or graft-versus-host disease;

other diseases or conditions in which undesirable inflammatory responses are to be inhibited can be treated, including, but not limited to, atherosclerosis, restenosis, myositis (including polymyositis, dermatomyositis).

Modes of Administration

The compound can be administered as a neutral compound or as a salt. Salts of compounds containing an amine or other basic group can be obtained, for example, by contacting the compound with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid.

Salts of compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-β-phenethylamine, dehydroabietylamine, N,N'-bisdehydroabietylamine, glucamine, N-methylglucamine, collidine, quinine, quinoline, and basic amino acid such as lysine and arginine. These salts may be prepared by methods known to those skilled in the art.

Salts of acidic functional groups contain a countercation such as sodium, potassium and the like.

Certain compounds described herein and their salts may also exist in the form of solvates, for example hydrates, and the present invention includes each solvate and mixtures thereof.

Certain compounds described herein may exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

Certain compounds described herein may exist in zwitterionic form. The present invention includes each zwitterionic form of these compounds and mixtures thereof.

Certain compounds described herein and their salts may exist in more than one crystal form. Polymorphs of these compounds form part of this invention and may be prepared by crystallization of the compound under different conditions, for example, by using different solvents or different solvent mixtures for recrystallization; by crystallization at different temperatures; or by various modes of cooling, ranging from very fast to very slow cooling during crystallization. Polymorphs may also be obtained by heating or melting the compound followed by gradual or fast cooling. The presence of polymorphs may be determined by solid probe nmr spectroscopy, it spectroscopy, differential scanning calorimetry, powder X-ray diffraction or such other techniques.

The language an "effective amount" or "pharmaceutically effective amount" is intended to include an amount which is sufficient to ameliorate a disease or condition and prevent its further progression or ameliorate the symptoms associated with the disease or condition. Such an amount can be administered prophylactically to a patient thought to be susceptible to development of a disease or condition. Such amount when administered prophylactically to a patient can also be effective to prevent or lessen the severity of the mediated condition. Such an amount is intended to include an amount which is sufficient to modulate a CCR9 receptor-mediated disease or condition. Conditions mediated by CCR9 receptors include all of the diseases or conditions described herein. Although the amount to be administered to a subject will, of course, be determined by a physician, in the light of all the relevant circumstances, an "effective amount" typically ranges between about 0.01 mg/kg/day to about 100 mg/kg/day, preferably between about 0.5 mg/kg/day to about 50 mg/kg/day.

The compounds described herein, and the pharmaceutically acceptable salts, solvates and hydrates thereof, have valuable pharmacological properties and can be used in pharmaceutical preparations containing the compound or pharmaceutically acceptable salts thereof, in combination with a pharmaceutically acceptable carrier or diluent. They are useful as therapeutic substances in preventing or treating diseases mediated by CCR9 receptors, such as inflammatory diseases, in human or non-human animals. Suitable pharmaceutically acceptable carriers include inert solid fillers or diluents and sterile aqueous or organic solutions. The active compound will be present in such pharmaceutical compositions in amounts sufficient to provide the desired dosage amount in the range described herein. Techniques for formulation and administration of the compounds of the instant invention can be found in *Remington: the Science and Practice of Pharmacy*, 19$^{th}$ edition, Mack Publishing Co., Easton, Pa. (1995).

For oral administration, the compound or salts thereof can be combined with a suitable solid or liquid carrier or diluent to form capsules, tablets, pills, powders, syrups, solutions, suspensions and the like.

The tablets, pills, capsules, and the like may also contain a binder such as gum tragacanth, acacias, corn starch or gelatin; excipients such as dicalcium phosphate; a disintegrating agent such as corn starch, potato starch, alginic acid, a lubricant such as magnesium stearate; and a sweetening agent such as sucrose lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

The active compounds can also be administered intranasally as, for example, liquid drops or spray. For oral or nasal inhalation, the compounds for use according to the present invention are conveniently delivered in the form of a dry powder inhaler, or an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

For parental administration the compounds of the present invention, or salts thereof can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable salts of the compounds. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that each syringability exists. It must be stable under the conditions of manufacture and storage and must be preserved against any contamination. The carrier can be solvent or dispersion medium containing, for example, water, ethanol, polyol (e.g. glycerol, propylene glycol and liquid polyethylene glycol), propylene glycol and liquid polyethylene glycol), suitable mixtures thereof, and vegetable oils. The injectable solutions prepared in this manner can then be administered intravenously, intraperitoneally, subcutaneously, or intramuscularly, with intramuscular administration being preferred in humans.

The compounds may also be formulated in rectal compositions such as suppositories or retention enemas, e.g., containing conventional suppository bases such as cocoa butter or other glycerides.

In addition, to the formulations described previously, the compounds may also be formulated as a depot preparation. Such long acting formulations may be administered by implantation, for example, subcutaneously or intramuscularly or by intramuscular injection. Thus, for example, as an emulsion in an acceptable oil, or ion exchange resins, or as sparingly soluble derivatives, for example, as sparingly soluble salts.

The effective dosage of active ingredient employed may vary depending on the particular compound employed, the mode of administration, the condition being treated and the severity of the condition being treated.

The compositions are formulated and administered in the same general manner as detailed herein. The compounds of the instant invention may be used effectively alone or in combination with one or more additional active agents depending on the desired target therapy. Combination therapy includes administration of a single pharmaceutical dosage formulation which contains a compound described herein and one or more additional active agents, as well as administration of the compound and each active agent in its own separate pharmaceutical dosage formulation. For example, a compound described herein or salt thereof can be administered to the patient together in a single oral dosage composition such as a tablet or capsule, or each agent administered in separate oral dosage formulations. Where separate dosage formulations are used, a compound of the invention and one or more additional active agents can be administered at essentially the same time, i.e., concurrently, or at separately staggered times, i.e., sequentially; combination therapy is understood to include all these regimens.

An effective amount of the compounds described herein can be used for the preparation of a medicament useful for treating a disease mediated by CCR9 receptors, such as an inflammatory disease, and for treating, preventing or reducing the risk of developing a disease mediated by CCR9 receptors, such as an inflammatory disease, in mammals, particularly in humans.

Preferably compounds of the invention or pharmaceutical formulations containing these compounds are in unit dosage form for administration to a mammal. The unit dosage form can be any unit dosage form known in the art including, for example, a capsule, an IV bag, a tablet, or a vial. The quantity of active ingredient (viz., a compound of Structural Formula I or salts thereof) in a unit dose of composition is an effective amount and may be varied according to the particular treatment involved. It may be appreciated that it may be necessary to make routine variations to the dosage depending on the age and condition of the patient. The dosage will also depend on the route of administration which may be by a variety of routes including oral, aerosol, rectal, transdermal, subcutaneous, intravenous, intramuscular, intraperitoneal and intranasal.

Pharmaceutical formulations of the invention are prepared by combining (e.g., mixing) an effective amount of a compound of the invention together with a pharmaceutically acceptable carrier or diluent. The present pharmaceutical formulations are prepared by known procedures using well known and readily available ingredients.

In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, lyophilized solid or paste, semi-solid, or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid.

Advantageously, compositions containing the compounds of the invention or the salts thereof may be provided in dosage unit form, each dosage unit containing from about 5% to about 95%, preferably about 20% to about 80%, of a compound of the invention, although it will, of course, readily be understood that the amount of the compound or compounds actually to be administered will be determined by a physician, in the light of all the relevant circumstances.

Powders and tablets preferably contain from about 1 to about 99 weight percent of the active ingredient which is the novel compound of this invention. Suitable solid carriers are magnesium carbonate, magnesium stearate, talc, sugar, lactose, pectin, dextrin, starch, gelatin, tragacanth, methyl cellulose, sodium carboxymethyl cellulose, low melting waxes, and cocoa butter.

The following pharmaceutical formulations 1 through 8 are illustrative only and are not intended to limit the scope of the invention in any way. "Active Ingredient", refers to a compound according to Structural Formula I or salts thereof.

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

|  | Weight |
| --- | --- |
| Active Ingredient | 0.25 |
| Ethanol | 25.75 |
| Propellant 22 (Chlorodifluoromethane) | 74.00 |
| Total | 100.00 |

The Active Ingredient is mixed with ethanol and the mixture added to a portion of the propellant 22, cooled to 30° C. and transferred to a filling device. The required amount is then fed to a stainless steel container and diluted with the remainder of the propellant. The valve units are then fitted to the container.

Formulation 4

Tablets, each containing 60 mg of Active ingredient, are made as follows:

| Active Ingredient | 60 mg |
| --- | --- |
| Starch | 45 mg |
| Microcrystalline cellulose | 35 mg |
| Polyvinylpyrrolidone | 4 mg |
| (as 10% solution in water) |  |
| Sodium carboxymethyl starch | 4.5 mg |
| Magnesium stearate | 0.5 mg |
| Talc | 1 mg |
| Total | 150 mg |

The Active Ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of Active Ingredient, are made as follows:

| Active Ingredient | 80 mg |
|---|---|
| Starch | 59 mg |
| Microcrystalline cellulose | 59 mg |
| Magnesium stearate | 2 mg |
| Total | 200 mg |

The Active Ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of Active Ingredient, are made as follows:

| Active Ingredient | 225 mg |
|---|---|
| Saturated fatty acid glycerides | 2,000 mg |
| Total | 2,225 mg |

The Active Ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of Active Ingredient per 5 mL dose, are made as follows:

| Active Ingredient | 50 mg |
|---|---|
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The Active Ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active Ingredient | 100 mg |
|---|---|
| Isotonic saline | 1,000 mL |

The solution of the above materials generally is administered intravenously to a subject at a rate of 1 mL per minute.

EXAMPLES

I. General Synthesis

Scheme I: General synthesis of diaryl methanones.

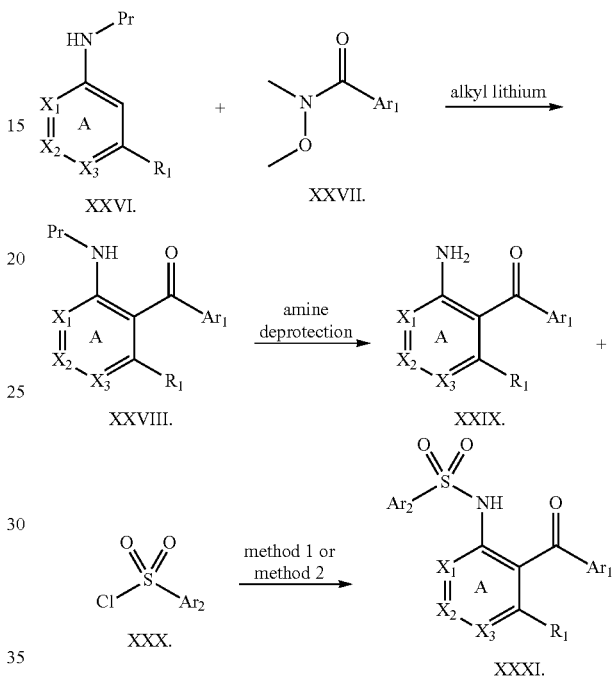

The sulfonamides of the invention can be synthesized by treating a protected aromatic amine (XXVI) or a protected heteroaromatic amine (XXVI), such as an aminobenzene, an aminopyridine, an aminopyrimidine, an aminopyridazine, an aminopyrazine, an aminotriazine or an aminotetrazine, with an alkyl lithium. Typically, the amino group of the aromatic amine or heteroaromatic amine is protected with protecting group which is stable under basic condition, such as a tert-butoxycarbonyl (BOC) group. The aromatic amine or heteroaromatic amine is dissolved in an aprotic solvent, preferably an ether. The solution is then cooled to about −50° C. to about −100° C. and about 1 equ. to about 2.5 equ. of alkyl lithium (e.g., n-butyl lithium, s-butyl lithium or t-butyl lithium) is added slowly to the reaction mixture. The temperature of the reaction mixture is allowed to increase to about −25° C. to about 25° C. After about 5 min. to about 45 min., about 1 equ. to about 1.5 equ. of a Weinreb amide (XXVII), such as a N-methoxy-N-methyl-benzamide or a N-methoxy-N-methyl-isonicotinamide, dissolved in an aprotic solvent is added to the reaction mixture. The reaction is allowed to continue stirring until the protected aromatic amine (XXVI) or protected heteroaromatic amine (XXVI) is consumed (typically, for about 0.5 hr to about 3 hr at about 15° C. to about 35° C.). The reaction is monitored by thin layer chromatography (tlc) to determine when the aromatic amine (XXVI) or heteroaromatic amine (XXVI) has been consumed. When the reaction is complete, it is quenched with an acidic aqueous solution to yield compound XXVIII.

After the amino group of compound XXVIII has been deprotected to yield compound XXIX, compound XXIX is converted to a sulfonamide by using one of two alternative methods. In method 1, compound XXIX is dissolved in an aprotic solvent and the solution is cooled to about −25° C. to about 10° C. and about 1 equ. to about 1.5 equ. of NaH is added to the mixture. After about 1 min. to about 15 min., about 1 equ. to about 1.5 equ. of sulfonyl chloride (XXX) dissolved in an aprotic solvent is added to the reaction mixture. An additional, amount of up to about 0.5 equ. NaH may be added to the reaction mixture. The reaction is stirred at about 15° C. to about 30° C. until the reaction is complete as indicated by tlc (typically, about 1 hr to about 3 hr). The reaction is quench by addition of water to yield sulfonamide (XXXI).

In the second method of forming sulfonamide (XXXI), compound XXIX is dissolved in an aprotic solvent and the mixture is cooled to about −10° C. to about 10° C. An excess amount of sodium bis(trimethylsilyl)amide (typically, about 1.5 equ. to about 3 equ.) in an aprotic solvent is added to the solution, and the reaction is allowed to stir for about 10 min. to about 45 min. A solution of about 1 equ. to about 2 equ. of sulfonyl chloride (XXX) in an aprotic solvent is added to the reaction mixture and the reaction is allowed to warm up to about 15° C. to about 30° C. and is stirred for about 6 hr to about 24 hr. The reaction is quenched with an acidic water solution to yield sulfamide (XXXI).

II. General Synthesis of N-(2-Benzoyl-Phenyl)-Arylsulfonamides and N-(2-Benzoyl-Phenyl)-Heteroarylsulfonamides Scheme II: Synthesis of N-(2-Benzoyl-Phenyl)-Benzenesulfonamides and N-(2-Benzoyl-Phenyl)-Heteroarylsulfonamides.

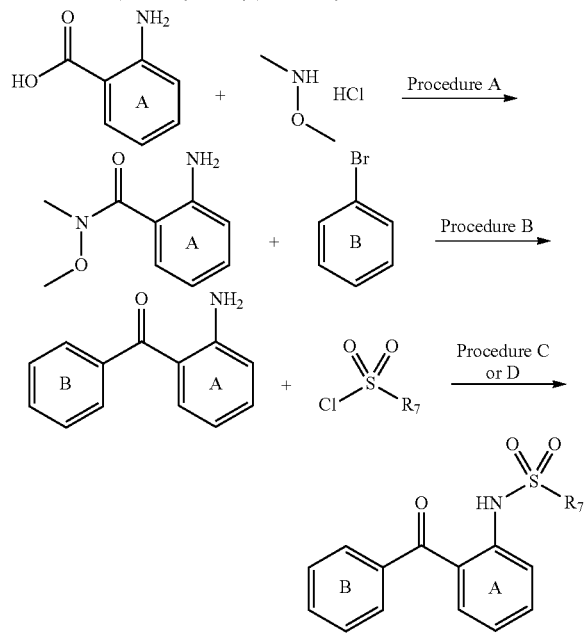

Procedure A

Synthesis of Weinreb Amides

A substituted anthranilic acid (24 mmol) was dissolved in acetonitrile (200 mL). 1.05 equivalents of N,O dimethylhydroxylamine hydrochloride, 1.05 equivalents of EDC, 0.05 equivalents of dimethylaminopyridine, and 1.0 equivalent of triethylamine were added and the reaction was stirred at room temperature overnight. The acetonitrile was removed by rotary evaporation and the residue was partitioned between ethyl acetate and water. The organic layer was washed with brine then concentrated to a residue. The residue was chromatographed on silica gel (ethyl acetate as eluent) to give the product. Typical yields are 70-90%.

The following compounds were prepared using Procedure A:

Example 1

2-Amino-5-bromo-N-methoxy-N-methyl-benzamide

LC-MS showed the product to be >95% pure and to have the expected M.W. of 259 (M+H$^+$). $^1$H NMR (Bruker 300 MHz, CDCl$_3$, shifts relative to the solvent peak at 7.24 ppm) δ 7.5 (s, 1H) δ 7.23 (d, 1H) S 6.58 (d, 1H) δ 4.68 (br s, 2H) δ 3.55 (s, 3H) δ 3.41 (s, 3H).

Example 2

2-Amino-N-methoxy-N-methyl-5-nitro-benzamide

LC-MS showed the product to be >95% pure and to have the expected M.W. of 226 (M+H$^+$). $^1$H NMR (CDCl$_3$, shifts relative to the solvent peak at 7.24 ppm) δ8.5 (s, 1H), δ8.1 (d, 1H) δ6.7 (d, 1H) δ3.6 (s, 3H) δ3.4 (s, 3H).

Example 3

2-Amino-5-chloro-N-methoxy-N-methyl-benzamide

LC-MS showed the product to be >95% pure and to have the expected M.W. of 215. (M+H$^+$). $^1$H NMR (Bruker 300 MHz, CDCl$_3$, shifts relative to the solvent peak at 7.24 ppm) δ7.4 (s, 1H) δ7.15 (m, 1H) δ6.65 (d, 1H) δ3.6 (s, 3H) δ3.28 (s, 3H).

Procedure B

General Synthesis of Substituted 2-aminobenzophenones

A substituted Weinreb amide (10 mmol) and a substituted bromobenzene (10 mmol) were dissolved in THF under nitrogen. The reaction mixture was cooled to −100° C. using a liquid nitrogen/diethyl ether bath. n-BuLi (21 mmol, 1.6 M in cyclohexanes) was introduced via syringe over a period of twenty minutes. The reaction mixture was allowed to warm to −70° C. and then quenched by adding of 21 mL of 1 N HCl. The reaction mixture was partitioned between ethyl acetate and saturated sodium bicarbonate. The organic layer was washed with saturated sodium chloride, then concentrated to a residue. The residue was chromatographed on silica gel using 1:1 ethyl acetate:hexanes to give the product. Typical yields are 30-60%.

The following compounds were prepared using Procedure B:

Example 4

(2-Amino-5-bromo-phenyl)-phenyl-methanone

LC-MS showed the product to be >95% pure and to have the expected M.W. of 276 (M+H$^+$). $^1$H NMR (Bruker 300

MHz, CDCl$_3$, shifts relative to the solvent peak at 7.24 ppm) δ 7.2-7.8 (m, 6H) δ 6.85 (d, 2H) δ 6.2 (br s, 2H).

Example 5

(2-Amino-5-nitro-phenyl)-(3-trifluoromethyl-phenyl)-methanone

LC-MS showed the product to be >95% pure and to have the expected M.W. of 311 (M+H$^+$). $^1$H NMR (Bruker 300 MHz, CDCl$_3$, shifts relative to the solvent peak at 7.24 ppm) δ7.6-8.4 (m, 5 H) δ6.75 (d, 2 H) δ7.0 (br s, 2H).

Example 6

(2-Amino-5-chloro-phenyl)-m-tolyl-methanone

LC-MS showed the product to be >95% pure and to have the expected M.W. of 246. (M+H$^+$). $^1$H NMR (Bruker 300 MHz, CDCl$_3$, shifts relative to the solvent peak at 7.24 ppm) δ7.25-7.5 (m, 5H) δ6.8 (d, 2H) δ2.4 (s, 3H).

Procedure C

General synthesis of
N-(2-benzoyl-phenyl)-benzenesulfonamides

A substituted 2-aminobenzophenone (1 mmol) was dissolved in 5 mL of pyridine. A substituted sulfonyl chloride (1.3 mmol) and dimethlaminopyridine (10 mg) were added to the 2-aminobenzophenone solution. The reaction mixture was heated to 110° C. for 2 hours. The solvent was evaporated under a stream of nitrogen and the product was isolated by reverse phase HPLC using the method given below. Typical yields are 60-80%.

General Method for HPLC Purification of
N-(2-benzoyl-phenyl)-benzenesulfonamides A crude N-(2-benzoyl-phenyl)-benzenesulfonamides was dissolved in 1 mL of MeOH (or MeOH/DCM) and filtered through a 0.45 micron filter. The solution was then injected (50-75 mg/injection) to a HPLC/MS system equipped with Waters 2700 Sample Manager auto-injector, Waters 600 Controller and Pumps, Waters 996 Diode Array detector, Micro Mass Platform LCZ mass spectrometer and Gilson FC-204 fraction collector. Solvents A and B were used for gradient elution of the purified compound using Phenomenex Luna 15 micron, C18(2) 100 A, 100×21.2 mm column at 20 mL/min flow rate.
Solvent A: 99% Water/1% CH$_3$CN/0.1% Formic Acid
Solvent B: 95% CH$_3$CN/5% Water/0.1% Formic Acid
The gradients were programmed according to their analytical scale HPLC retention time (t$_{ana}$) which was obtained by running a linear gradient of 0% B to 100% B in A in 3.5 min on a Phenomenex Luna 5 micron C18(2) 50×4.6 mm column at 3.5 mL/min.

Linear mixing of 0% of B to X % of B in A was used according to the following formula with some adjustments for some compounds.

$$X = t_{ana} \times 95/3.5 + 15$$

About 15 mL to 25 mL size fractions were collected based on mass triggered collection. They were combined according to their purities based on mass spectral pattern of the fractions.

The following examples were prepared using Procedure C:

Example 7

N-[4-Chloro-2-(2-chloro-benzoyl)-phenyl]-4-nitro-benzenesulfonamide

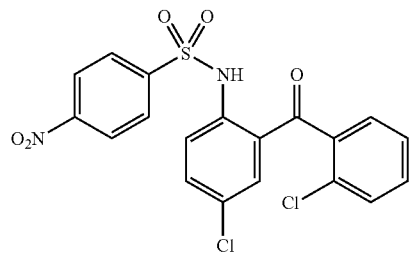

LC-MS showed the product to be >95% pure and to have the expected M.W. of 451 (M+H$^+$). $^1$H NMR (Bruker 300 MHz, CDCl$_3$, shifts relative to the solvent peak at 7.24 ppm) δ 10.0 (s, 1H) δ 8.0-8.4 (dd, 4H) δ 7.8 (d, 1 H) δ 7.38-7.58 (m, 6H).

Example 8

Thiophene-2-sulfonic acid
(2-benzoyl-4-chloro-phenyl)-amide

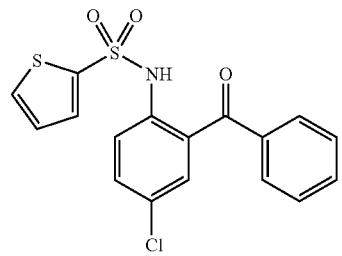

LC-MS showed the product to be >95% pure and to have the expected M.W. of 378 (M+H$^+$). $^1$H NMR (Bruker 300 MHz, CDCl$_3$, shifts relative to the solvent peak at 7.24 ppm) δ 10.0 (s, 1H) δ 7.85 (d, 1H) δ 7.4-7.7 (m, 9 H) δ 6.85 (d, 1H).

Example 9

N-(2-Benzoyl-4-chloro-phenyl)-4-iodo-benzene-sulfonamide

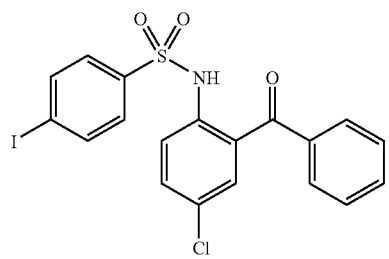

LC-MS showed the product to be >95% pure and to have the expected M.W. of 498 (M+H$^+$). $^1$H NMR (Bruker 300 MHz, CDCl$_3$, shifts relative to the solvent peak at 7.24 ppm) δ 9.7 (s, 1H) δ 7.3-7.8 (m, 12H).

Example 10

N-(2-Benzoyl-4-chloro-phenyl)-4-chloro-benzenesulfonamide

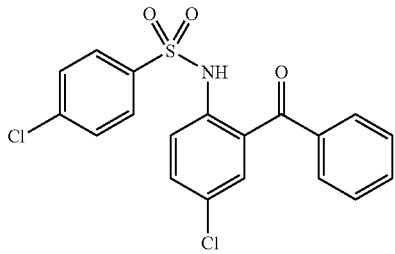

LC-MS showed the product to be >95% pure and to have the expected M.W. of 406 (M+H$^+$). $^1$H NMR (Bruker 300 MHz, CDCl$_3$, shifts relative to the solvent peak at 7.24 ppm) δ 9.65 (s, 1H) δ 7.2-7.8 (m, 12H).

Example 11

N-(2-Benzoyl-4-chloro-phenyl)-4-tert-butyl-benzenesulfonamide

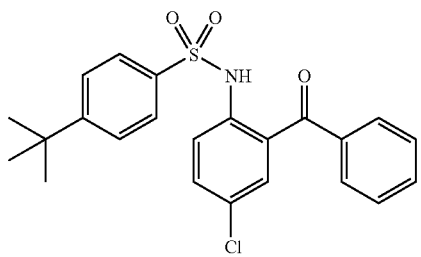

LC-MS showed the product to be >95% pure and to have the expected M.W. of 428 (M+H$^+$). $^1$H NMR (CDCl$_3$, shifts relative to the solvent peak at 7.24 ppm) δ 9.9 (s, 1H) 7.2-7.8 (m, 12H), δ 1.18 (s, 9H).

Example 12

N-(2-Benzoyl-4-chloro-phenyl)-4-propyl-benzenesulfonamide

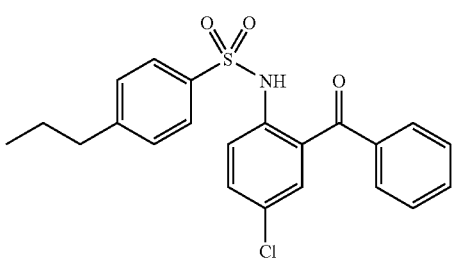

LC-MS showed the product to be >95% pure and to have the expected M.W. of 414 (M+H$^+$). $^1$H NMR (Bruker 300 MHz, CDCl$_3$, shifts relative to the solvent peak at 7.24 ppm) δ 9.9 (s, 1H) δ 7.0-7.8 (m, 12H), δ 2.42 (m, 2H) δ 1.5 (m, 2H) δ 0.92 (m, 3H).

Example 13

N-(2-Benzoyl-4-chloro-phenyl)-4-ethyl-benzenesulfonamide

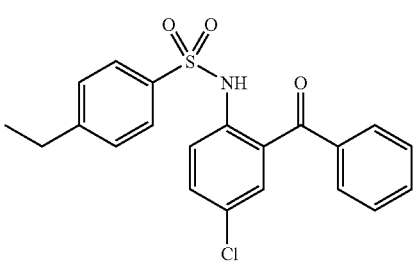

LC-MS showed the product to be >95% pure and to have the expected M.W. of 400 (M+H$^+$). $^1$H NMR (Bruker 300 MHz, CDCl$_3$, shifts relative to the solvent peak at 7.24 ppm) δ 9.9 (s, 1H) δ 7.0-7.8 (m, 12H), δ 2.42 (t, 2H) δ 0.92 (d, 3H).

Example 14

N-(2-Benzoyl-4-nitro-phenyl)-4-ethyl-benzenesulfonamide

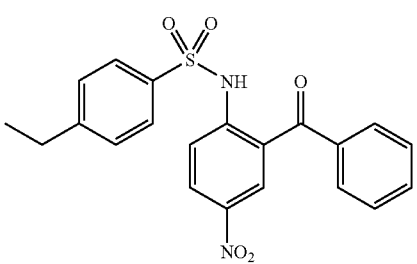

LC-MS showed the product to be >95% pure and to have the expected M.W. of 411 (M+H$^+$). $^1$H NMR (Bruker 300 MHz, CDCl$_3$, shifts relative to the solvent peak at 7.24 ppm) δ 10.6 (s, 1H) δ 8.2-8.45 (m, 2H) δ 7.2-7.9 (m, 10H), δ 2.6 (q, 2H) δ 1.05 (t, 3H).

Example 15

N-(2-Benzoyl-4-chloro-phenyl)-4-isopropyl-benzenesulfonamide

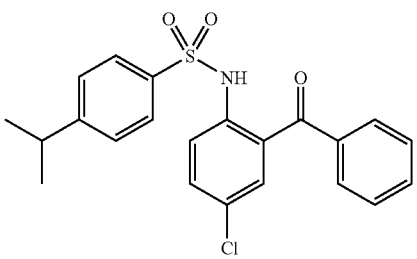

LC-MS showed the product to be >95% pure and to have the expected M.W. of 414 (M+H⁺). ¹H NMR (Bruker 300 MHz, CDCl₃, shifts relative to the solvent peak at 7.24 ppm) δ 9.85 (s, 1H) δ 7.0-7.8 (m, 12H), δ 2.8 (m, 1H) δ 1.03 (d, 6H).

Example 16

N-(2-Benzoyl-4-bromo-phenyl)-4-ethyl-benzene-sulfonamide

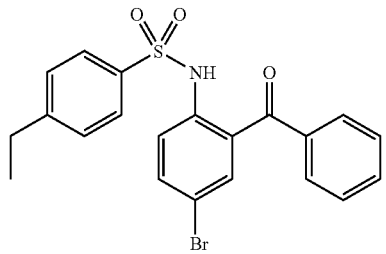

LC-MS showed the product to be >95% pure and to have the expected M.W. of 444 (M+H⁺). ¹H NMR (Bruker 300 MHz, CDCl₃, shifts relative to the solvent peak at 7.24 ppm) δ9.8 (s, 1H), δ7.38-7.8 (m, 10H) δ7.08 (d, 2H) δ2.47 (q, 2H) δ1.1 (t, 3H).

Example 17

N-(2-Benzoyl-4-bromo-phenyl)-4-methoxy-benzene-sulfonamide

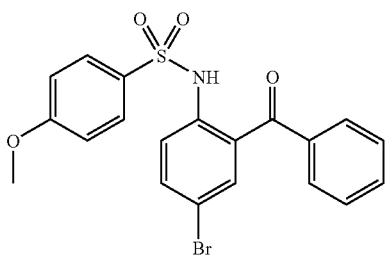

LC-MS showed the product to be >95% pure and to have the expected M.W. of 446 (M+H⁺). ¹H NMR Bruker 300 MHz, (CDCl₃, shifts relative to the solvent peak at 7.24 ppm) δ9.61 (s, 1H) δ7.2-7.8 (m, 10 H), δ5 6.64 (d, 2H) δ3.78 (s, 3H).

Example 18

N-(2-Benzoyl-4-bromo-phenyl)-4-isopropyl-benzenesulfonamide

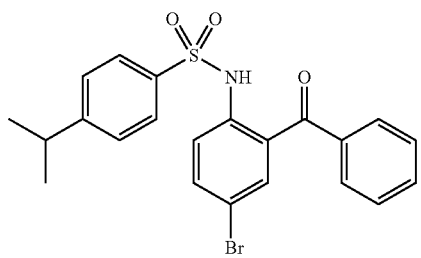

LC-MS showed the product to be >95% pure and to have the expected M.W. of 459 (M+H⁺). ¹H NMR (Bruker 300 MHz, CDCl₃, shifts relative to the solvent peak at 7.24 ppm) δ9.9 (s, 1H), δ7.28-7.8 (m, 10H) δ7.16 (d, 2H), δ2.8 (m, 1H) δ1.08 (d, 1H).

Example 19

4-Ethyl-N-[4-nitro-2-(3-trifluoromethyl-benzoyl)-phenyl]-benzenesulfonamide

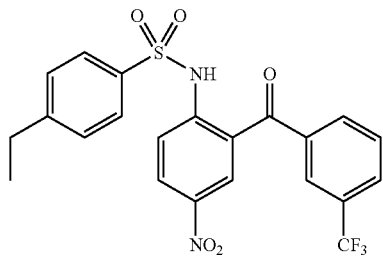

LC-Ms showed the product to be >95% pure and to have the expected M.W. of 479 (M+H⁺). ¹H NMR (Bruker 300 MHz, CDCl₃, shifts relative to the solvent peak at 7.24 ppm) δ10.9 (s, 1H), b 8.4 (m, 2H) δ7.6-8.0 (m, 6 H) δ7.28 (m, 2 H) δ2.62 (q, 2H) δ1.09 (t, 3H).

Example 20

N-[4-Chloro-2-(3-methyl-benzoyl)-phenyl]-4-ethyl-benzenesulfonamide

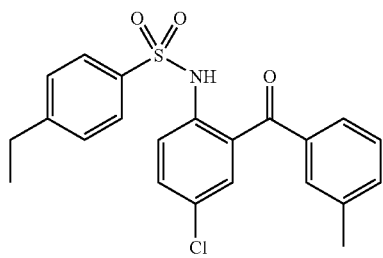

LC-MS showed the product to be >95% pure and to have the expected M.W. of 414 (M+H⁺). ¹H NMR (Bruker 300 MHz, CDCl₃, shifts relative to the solvent peak at 7.24 ppm) δ9.8 (s, 1H) δ7.0-7.9 (m, 11H) δ2.48 (q, 2H) δ2.39 (s, 3H) δ1.13 (t, 3H).

Example 21

N-(2-Benzoyl-4-bromo-phenyl)-4-chloro-benzene-sulfonamide

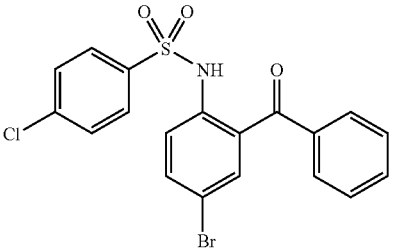

LC-MS showed the product to be >95% pure and to have the expected M.W. of 450 (M+H⁺). ¹H NMR (Bruker 300

MHz, CDCl₃, shifts relative to the solvent peak at 7.24 ppm) δ9.7 (s, 1H), δ7.2-8.0 (m, 12H).

Procedure D

Alternate Synthesis of
N-(2-benzoyl-phenyl)-benzenesulfonamides

A solution of substituted 2-aminobenzophenone (0.5 mmol), sulfonyl chloride (0.7 mmol), and N-methylmorpholine (0.9 mmol) in dichloromethane (5 mL) was stirred at 40° C. for 20 hours. The mixture was cooled to room temperature, washed with water (2×5 mL), brine (5 mL) dried over Na₂SO₄, filtered, and purified by silica gel chromatography using dichloromethane:hexanes (1:1) to afford the desired N-(2-benzoyl-phenyl)-benzenesulfonamides.

The following examples were prepared using Procedure D:

Example 22

N-(2-Benzoyl-4-chloro-phenyl)-4-ethoxy-benzenesulfonamide

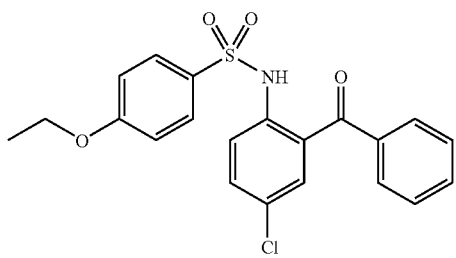

LC-MS showed the product to be >95% pure and to have the expected M.W. of 416 (M+H⁺). ¹H-NMR (Bruker 300 MHz, CDCl₃, shifts relative to the solvent peak at 7.24 ppm): δ 1.30-1.40 (t, 3H), δ 3.85-3.95 (m, 2H), δ 6.68-6.70 (d, 2H), δ 7.30-7.65 (m, 9H), δ 7.75-7.77 (d, H), δ 9.65 (s, H).

Example 23

N-(2-Benzoyl-4-chloro-phenyl)-4-propoxy-benzenesulfonamide

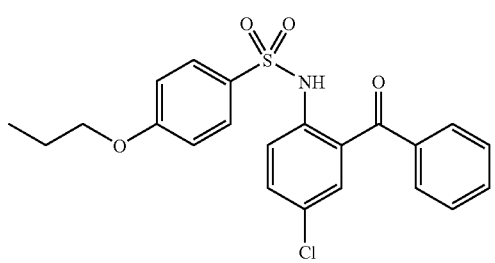

LC-MS showed the product to be >95% pure and to have the expected M.W. of 430 (M+H⁺). ¹H-NMR (Bruker 300 MHz, CDCl₃, shifts relative to the solvent peak at 7.24 ppm): δ 0.99-1.10 (t, 3H), δ 1.70-1.80 (m, 2H), δ 3.70-3.75 (t, 2H), δ 6.68-6.70 (d, 2H), δ 7.30-7.65 (m, 9H), δ 7.75-7.77 (d, H), δ 9.65 (s, H).

Example 24

N-(2-Benzoyl-4-chloro-phenyl)-4-isopropoxy-benzenesulfonamide

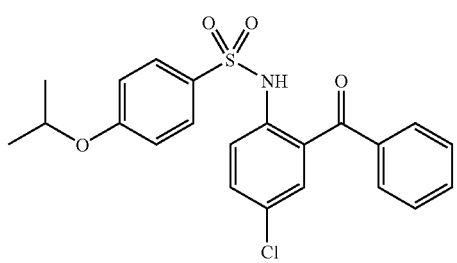

LC-MS showed the product to be >95% pure and to have the expected M.W. of 430 (M+H⁺). ¹H-NMR (CDCl₃, Bruker 300 MHz): δ 1.25-1.26 (d, 6H), δ 4.30-4.48 (m, H), δ 6.68-6.70 (d, 2H), δ 7.30-7.65 (m, 9H), δ 7.75-7.77 (d, H), δ 9.70 (s, H).

Example 25

N-(2-Benzoyl-4-chloro-phenyl)-4-butoxy-benzenesulfonamide

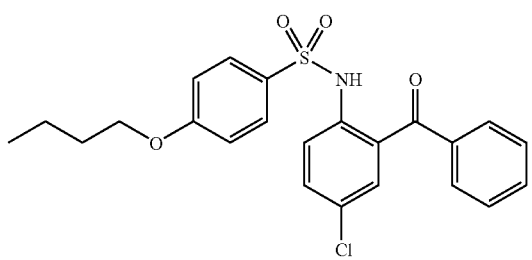

LC-MS showed the product to be >95% pure and to have the expected M.W. of 444 (M+H⁺). ¹H-NMR (Bruker 300 MHz, CDCl₃, shifts relative to the solvent peak at 7.24 ppm): δ 0.95-1.00 (t, 3H), δ 1.40-1.60 (m, 2H), δ1.70-1.80 (m, 2H), δ 3.75-3.80 (t, 2H), δ 6.68-6.70 (d, 2H), δ 7.30-7.65 (m, 9H), δ 7.75-7.77 (d, H), δ 9.70 (s, H).

Example 26

N-(2-Benzoyl-4-chloro-phenyl)-4-benzyloxy-benzenesulfonamide

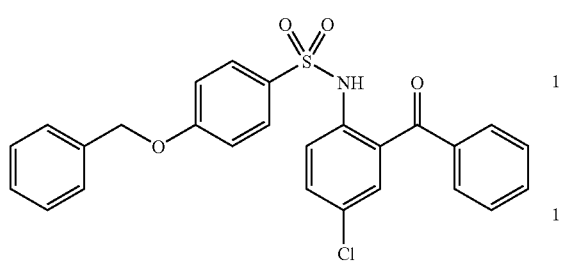

LC-MS showed the product to be >95% pure and to have the expected M.W. of 478 (M+H+). $^1$H-NMR (Bruker 300 MHz, CDCl$_3$, shifts relative to the solvent peak at 7.24 ppm): δ 4.93 (s, 2H), δ6.75-6.80 (d, 2H), δ 7.335-7.55 (m, 11H), δ 7.60-7.70 (m, 3H), δ 7.78-7.80 (d, H), δ 9.70 (s, H).

Example 27

N-(2-Benzoyl-4-chloro-phenyl)-4-phenoxy-benzenesulfonamide

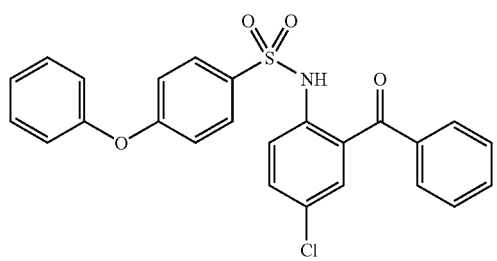

LC-MS showed the product to be >95% pure and to have the expected M.W. of 464 (M+H+). $^1$H-NMR (Bruker 300 MHz, CDCl$_3$, shifts relative to the solvent peak at 7.24 ppm): δ (ppm)=6.78-6.80 (d, 2H), 6.90-6.93 (d, 2H), 7.20-7.24 (t, H), 7.33-7.45 (m, 3H), 7.45-7.53 (m, 5H), 7.60-7.70 (m, 3H), 7.75-7.77 (d, H), 9.78 (s, H).

III. General Synthesis of 2-Amino-Pyridophenone-Sulfonamides

Scheme III: General Synthesis of 2-Amino-Pyridophenone-Sulfonamides.

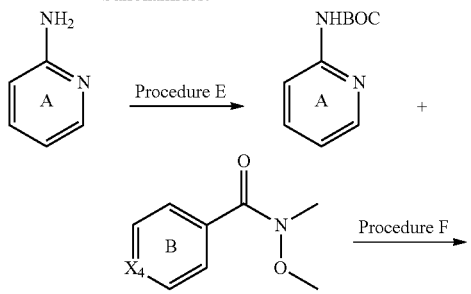

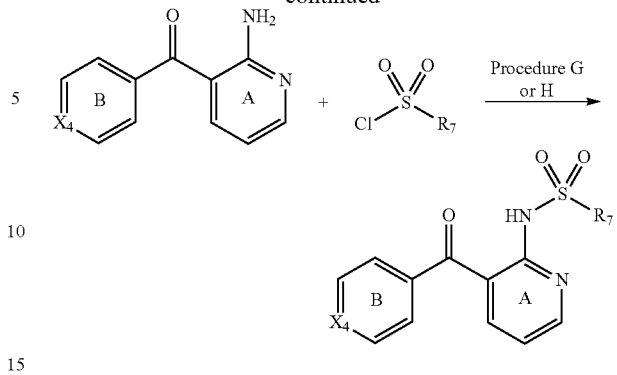

Procedure E

BOC Protection of Substituted 2-aminopyridines

To a mixture of 2-amino-5-substituted-pyridine (0.10 mol), 4-dimethylaminopyridine (DMAP, 1.22 g, 0.01 mol), and triethylamine (TEA, 20 mL, 0.15 mol) in dichloromethane (80 mL) and DMF (4 mL) at 0° C. was added a solution of di-t-butyl dicarbonate (28.4 g, 0.13 mol) in dichloromethane (20 mL). The mixture was stirred at room temperature overnight. The mixture was washed with water (3×100 mL), brine (100 mL), dried with anhydrous Na$_2$SO$_4$, and filtered. The filtrate was concentrated in vacuo to afford a solid which was collected by filtration and washed with small amount of DCM to give the expected product in 40-60% yield.

The following example was prepared using Procedure E:

Example 28

(5-Chloro-pyridin-2-yl)-carbamic acid tert-butyl ester $^1$H-NMR (Bruker 300 MHz, CDCl$_3$, shifts relative to the solvent peak at 7.24 ppm) 1.54 (s, 9H), 7.59-7.64 (dd, H), 7.94-7.97 (d, H), 8.24-8.25 (dd, H), 8.39 (b, H). LC-MS showed the product to be >95% pure. The molecular ion was not observed but the fragment corresponding to loss of the t-butyl group was evident (M.W. of 173/175).

Procedure F

Synthesis 2-aminopyridin-3-yl)-phenyl-methanones or 2-aminopyridin-3-yl)-pyridin-4-yl-methanones A solution of BOC protected 5-substituted 2-aminopyridine (10 mmol) in anhydrous tetrahydrofuran (THF, 5 mL) was cooled to −78° C. under nitrogen atmosphere with stirring. A solution of n-butyl lithium in hexane (2.5 M, 8.8 mL) was added dropwise, and the mixture was stirred at 0° C. for 10 min. A Weinreb amide (12 mmol) was prepared as in Procedure A and was dissolved in anhydrous THF (5 mL) and added to the reaction mixture. The reaction mixture was warmed to room temperature and stirred for 2 hours. The reaction was added to an ice-0.18 M aqueous citric acid solution (100g-130 mL) mixture, then extracted with ethyl acetate (EtOAc, 150 mL and 50 mL). The combined organic layer was washed with water (2×100 mL), brine (100 mL), dried over anhydrous Na$_2$SO$_4$, and filtered. The crude material concentrated from the filtrate was purified by flash chromatography to give a solid product. This compound was heated in 4 N HCl/dioxane (6 mL) at 100° C. for 2 hours, then cooled to room temperature. The mixture was evaporated in vacuo and the residue was taken up into a saturated aqueous NaHCO$_3$ solution (50 mL) and extracted with EtOAc (2×50 mL). The combined organic layer was washed with water (2×50 mL), then with brine (50 mL), dried over anhydrous Na$_2$SO$_4$, and filtered. The filtrate was evaporated and dried in vacuum to afford a pale yellow solid product in yields of 40-60% for the two steps.

The following examples were prepared using Procedure F:

Example 29

(2-Amino-5-chloro-pyridin-3-yl)-pyridin-4-yl-methanone

LC-MS showed the product to be >95% pure and to have the expected M.W. of 234 (M+H$^+$). $^1$H-NMR (Bruker 300 MHz, CDCl$_3$, shifts relative to the solvent peak at 7.24 ppm) δ 6.96 (b, 2H), δ 7.40-7.44 (m, 2H), δ 7.62-7.63 (d, H), δ 8.25-8.26 (d, H), δ 8.81-8.84 (m, 2H).

Example 30

(2-Amino-5-chloro-pyridin-3-yl)-phenyl-methanone

LC-MS showed the product to be >95% pure and to have the expected M.W. of 233 (M+H$^+$). $^1$H-NMR (Bruker 300 MHz, CDCl$_3$, shifts relative to the solvent peak at 7.24 ppm): δ 6.69-6.84 (br s, 2H), 7.48-7.54 (m, 2H), 7.57-7.65 (m, 3H), 7.74-7.75 (d, H), 8.22-8.23 (d, H).

Procedure G

Alternate Synthesis of Sulfonamides Using NaH

To a solution of a 2-aminopyridophenone (0.5 mmol) in dry DMF (1 mL) at 0° C. was added NaH (60%, 20 mg, 0.5 mmol). The mixture was stirred for 5 min. The a sulfonyl chloride (0.55 mmol) in dry DMF (1 mL) was added, and the mixture stirred at 0° C. for 10 min. The second portion of NaH (0.25 mmol) was added, and the mixture stirred at room temperature for 2 hours. The mixture was quenched with ice water (20 mL) and extracted with EtOAc (3×10 mL). The combined organic layers were washed with water (2×10 mL), brine (10 mL), dried over anhydrous Na$_2$SO$_4$, filtered, and evaporated in vacuo to give crude product. The crude product was purified by chromatography using DCM:EtOAc (100:0 to 98:2) or hexane:EtOAc (9:1) as eluent to afford the purified product in 10-24% yield.

The following examples were prepared using Procedure G:

Example 31

N-(3-Benzoyl-5-chloro-pyridin-2-yl)-4-isopropoxy-benzenesulfonamide

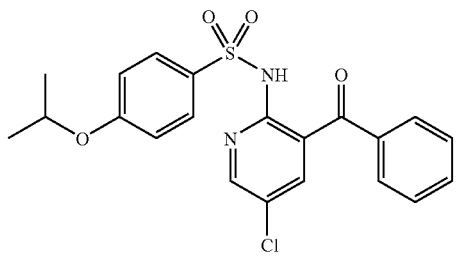

LC-MS showed the product to be >95% pure and to have the expected M.W. of 431 (M+H$^+$) $^1$H-NMR (Bruker 300 MHz, CDCl$_3$, shifts relative to the solvent peak at 7.24 ppm): δ 1.34-1.36 (d, 6H), δ 4.57-4.70 (m, H), δ 6.91-6.98 (d, 2H), δ 7.50-7.70 (m, 5H), δ 7.82-7.83 (d, H), δ 8.08-8.12 (d, 2H), δ 8.38-8.39 (d, H), δ 10.70 (s, H). Elemental analysis: C=58.26%/cal. 58.53%, H=4.65%/cal. 4.44%, N=6.26%/cal. 6.50%.

Example 32

N-[4-Chloro-2-(pyridine-4-carbonyl)-phenyl]-4-ethoxy-benzenesulfonamide

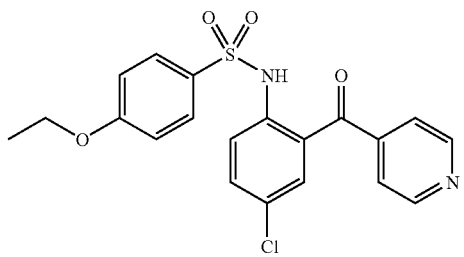

LC-MS showed the product to be >95% pure and to have the expected M.W. of 417 (M+H$^+$); $^1$H NMR (CDCl$_3$, shifts relative to the solvent peak at 7.24 ppm) δ 9.90 (1H, s), δ 8.80 (2H, s), δ 7.79 (1H, d), δ 6.76 (2H, d), δ 7.51 (1H, d), δ 7.33-7.20 (3H, m), δ 6.75 (2H, d), δ 3.90 (2H, m), δ 1.5 (3H, m).

Example 33

N-[4-Chloro-2-(pyridine-4-carbonyl)-phenyl]-4-isopropyl-benzenesulfonamide

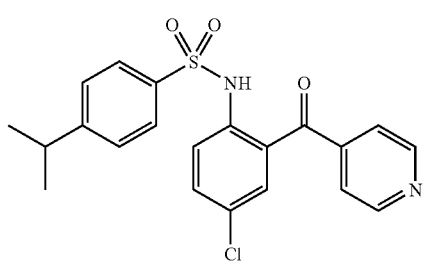

LC-MS showed the product to be >95% pure and to have the expected M.W. of 415 (M+H⁺); ¹H NMR (Bruker 300 MHz, CDCl₃, shifts relative to the solvent peak at 7.24 ppm) δ 10.06 (1H, s), δ 8.77 (1H, s), δ 7.79 (1H, d), δ 7.70-7.62 (3H, m), δ 7.56-7.51 (1H, m), δ 7.33-7.16 (5H, m), δ 1.19 (6H, m), δ 2.88 (1H, m).

Example 34

N-[4-Chloro-2-(pyridine-4-carbonyl)-phenyl]-4-isobutyl-benzenesulfonamide

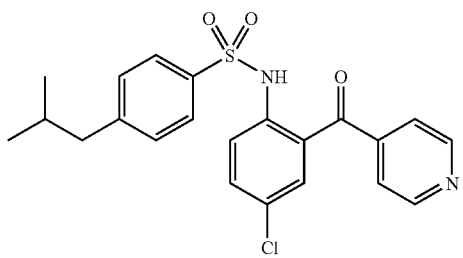

LC-MS showed the product to be >95% pure and to have the expected M.W. of 429 (M+H⁺); ¹H NMR (Bruker 300 MHz, CDCl₃, shifts relative to the solvent peak at 7.24 ppm) δ 10.06 (1H, s), δ 7.77 (1H, s), δ 7.67-7.61 (3H, m), δ 7.58-7.47 (1H, m), δ 7.33-7.24 (3H, m), δ 7.17-7.08 (3H, m), δ 2.42 (2H, m), δ 0.86 (6H, m).

Another example of a compound prepared using Procedure G is N-[4-chloro-2-(pyridine-4-carbonyl)-phenyl]-4-ethyl-benzenesulfonamide. LC-MS showed the product to be >95% pure and to have the expected M.W. of 401 (M+H⁺).

Procedure H

Alternate Synthesis of Sulfonamides Using Na(TMS)₂N

To a suspension of a 2-aminopyridophenone (1 mmol) in dry DMF (5 mL) at 0° C. was added a solution of sodium bis(trimethylsilyl)amide in THF (1M, 2.2 mL). This mixture was stirred at 0° C. for 20 min. A solution of a sulfonyl chloride (1.3 mmol) in dry DMF (2 mL) was added, and the reaction mixture was stirred at room temperature overnight. The reaction was quenched with ice water (60 mL), neutralized with 0.18 M aqueous citric acid solution (3 mL) to about pH 7.5, then extracted with EtOAc (60 mL, 2×20 mL). The combined organic layers were washed with water (2×50 mL), brine (50 mL), dried over anhydrous Na₂SO₄, filtered, and evaporated in vacuo to give a crude product. The crude product was purified by chromatography using DCM:EtOAc (6:4) as elute to afford a solid product in 20-25% yield.

The following examples were prepared using Procedure H:

Example 35

N-[5-Chloro-3-(pyridine-4-carbonyl)-pyridin-2-yl]-4-ethoxy-benzenesulfonamide

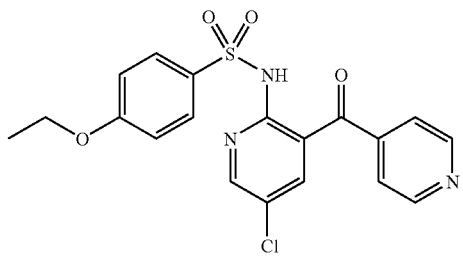

LC-MS showed the product to be >95% pure and to have the expected M.W. of 418 (M+H⁺). ¹H-NMR (Bruker 300 MHz, CDCl₃, shifts relative to the solvent peak at 7.24 ppm): δ 1.40-1.44 (t, 3H), 54.03-4.12 (m, 2H), δ 6.93-6.96 (d, 2H), δ 7.39-7.42 (d, 2H), δ 7.70-7.72 (d, H), δ 8.08-8.11 (d, 2H), δ 8.39-8.40 (d, H), δ 8.84-8.86 (d, 2H), δ 10.73 (s, H).

Example 36

N-[5-Chloro-3-(pyridine-4-carbonyl)-pyridin-2-yl]-4-isopropoxy-benzenesulfonamide

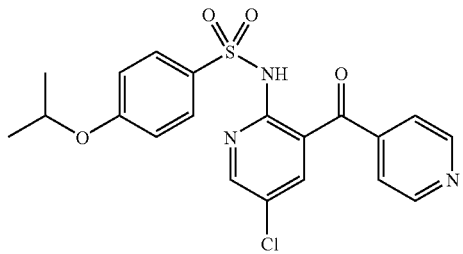

LC-MS showed the product to be >95% pure and to have the expected M.W. of 432 (M+H⁺). ¹H NMR (Bruker 300 MHz, CDCl₃, shifts relative to the solvent peak at 7.24 ppm): δ 1.35-1.36 (d, 6H), δ 4.57-4.67 (m, H), δ 6.92-6.95 (d, 2H), δ 7.42-7.44 (d, 2H), δ 7.72-7.73 (d, H), δ 8.08-8.11 (d, 2H), δ 8.41-8.42 (d, H), δ 8.84-8.87 (d, 2H), δ 10.74 (s, H).

IV. Synthesis of (2-Amino-5-Chloro-Phenyl)-Pyridin-3-yl-Methanones

Scheme IV: Synthesis of (2-amino-5-chloro-phenyl)-pyridin-3-yl-methanones.

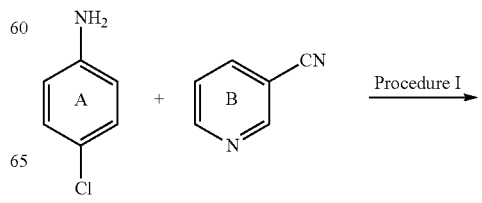

-continued

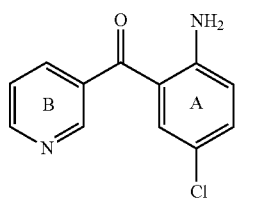

Procedure I

Alternate Synthesis of (2-amino-5-chloro-phenyl)-pyridin-3-yl-methanones using $BCl_3$ To a solution of 85 mL $BCl_3$ in 80 mL 1,1,2,2-tetrachloroethane, stirred in an ice bath, was added a solution of 4 g of p-chloroaniline in 50 mL of tetrachloroethane. After 5 min, 3 g of 3-cyanopyridine is added followed by 7 g of aluminum chloride. The mixture was stirred at room temperature for 20 min and then heated at reflux for 6 hr. After cooling, 25 mL of 3N HCl was added and refluxing continued for 1 hr. After cooling, the filtrate was concentrated, made basic with 6N NaOH, then extraction with dichloromethane. The organic solution was dried over $MgSO_4$ and concentrated. The residue was flash chromatographed on silica gel (Hexane/EtOAc=2:1) to give a 10-20% yield of product.

The following Example was prepared using Procedure I:

Example 37

(2-Amino-5-chloro-phenyl)-pyridin-3-yl-methanone

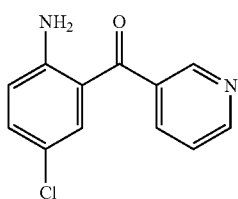

LC-MS showed the product to be >95% pure and to have the expected M.W. of 233. (M+H$^+$). $^1$H NMR (Bruker 300 MHz, CDCl$_3$, shifts relative to the solvent peak at 7.24 ppm) δ 8.95 (s, 1H), δ 8.80 (d, 1H), δ 8.18 (d, 1H), δ 7.40-7.45 (m, 1H), δ 7.20-7.30 (m, 2H) δ 7.10 (s, 1H), δ 6.30 (br s, 2H).

(2-Amino-5-chloro-phenyl)-pyridin-3-yl-methanones prepared using the method depicted in Scheme III can be converted to the corresponding aryl sulfonamide or heteroaryl sulfonamide using Procedure G or H. The following example was prepared using the method depicted in Scheme III followed by Procedure G or H:

Example 38

N-[4-Chloro-2-(pyridine-3-carbonyl)-phenyl]-4-methyl-benzenesulfonamide

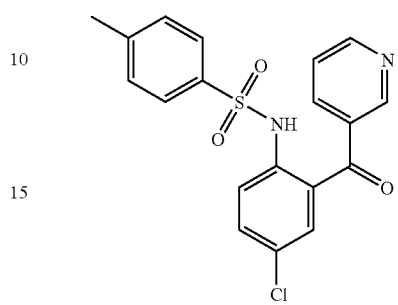

LC-MS showed the product to be >95% pure and to have the expected M.W. of 387 (M+H$^+$); $^1$H NMR (Bruker 300 MHz, CDCl$_3$, shifts relative to the solvent peak at 7.24 ppm) δ 9.66 (s, 1H), δ 7.87-7.76 (m, 3H), δ 7.56-7.50 (m, 4H), δ 7.43-7.40 (m, 1H), δ 7.28 (s, 1H), δ 7.08 (d, 2H), δ 3.50 (s, 3H).

V. Synthesis of (2-amino-5-chloro-phenyl)-pyridin-4-yl-methanones

Scheme V: Synthesis of (2-amino-5-chloro-phenyl)-pyridin-4-yl-methanones.

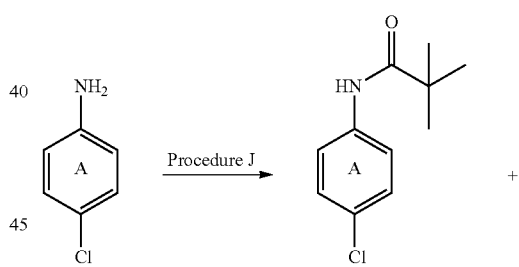

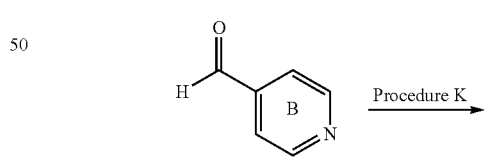

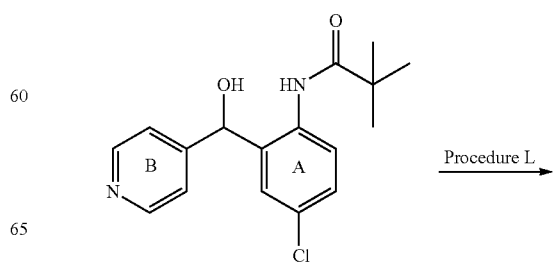

-continued

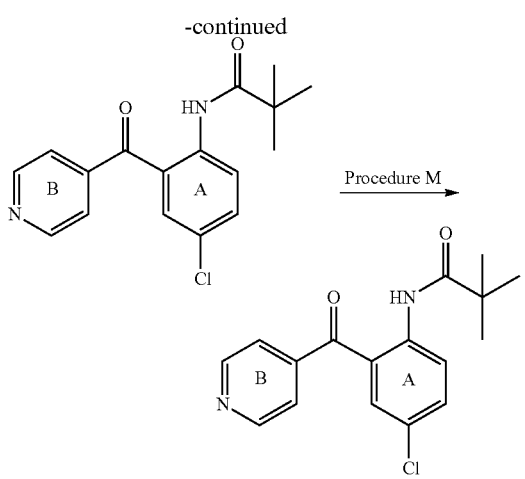

Procedure J

Pivaloyl Protection of 4-chloro Aniline

To a mixture of 2.3 g of 4-chloroaniline and 3 mL of triethylamine in 20 mL of dichloromethane was added 2.3 g of trimethylacetyl chloride. The reaction mixture was stirred overnight at room temperature, then washed with 1 N HCl. The organic layer was separated and dried over MgSO$_4$. Removal of the solvent afforded 4.5 g of pure product.
The following examples were prepared using Procedure J:

Example 39

N-(5-Chloro-pyridin-2-yl)-2,2-dimethyl-propionamide

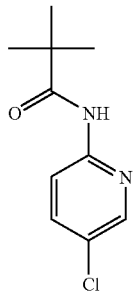

LC-MS showed the product to be >95% pure and to have the expected M.W. of 213 (M+H$^+$).

Example 40

N-(4-Chloro-phenyl)-2,2-dimethyl-propionamide

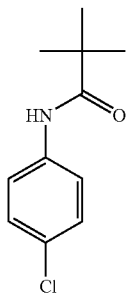

LC-MS showed the product to be >95% pure and to have the expected M.W. of 212. (M+H$^+$). $^1$H NMR (Bruker 300 MHz, CDCl$_3$, shifts relative to the solvent peak at 7.24 ppm) δ10.51 (s, 1H), δ 7.25 (d, 2H), δ7.15 (d, 2H), δ1.51 (s, 9H).

Procedure K

A solution of 2 g of pivaloyl protected 4-chloroaniline in 50 mL of THF was cooled to −78° C. under nitrogen. A solution of n-butyl lithium (14 mL of 2 N in hexane) was added dropwise. The mixture was allowed to warm 0° C. and stirring continued at 0° C. for one hour. A pyridine 4-carboxaldehyde was added to the solution and the reaction was stirred at 0° C. for one hour. The reaction mixture was poured into ethyl acetate and washed with water. The organic layer was separated and dried over MgSO$_4$. Removal of the solvent followed by chromatography on silica gel (hexane:ethyl acetate 2:1 as eluent) afforded 1 g of the desired product.
The following example was prepared using Procedure K:

Example 41

N-[4-Chloro-2-(hydroxy-pyridin-4-yl-methyl)-phenyl]-2,2-dimethyl-propionamide

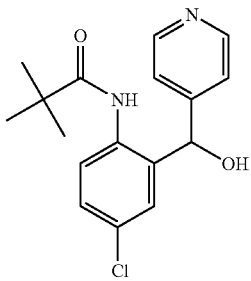

LC-MS showed the product to be >95% pure and to have the expected M.W. of 319. (M+H$^+$).

Procedure L

The alcohol from Procedure K (1 g) was dissolved in 25 mL of dichloromethane. Manganese dioxide (2 g) was added and the mixture was heated to reflux for 2 hours. After cooling and filtration, the solvent was evaporated to give 0.95 g of the desired ketone.
The following example was prepared using Procedure L:

Example 42

N-[4-Chloro-2-(pyridine-4-carbonyl)-phenyl]-2,2-dimethyl-propionamide

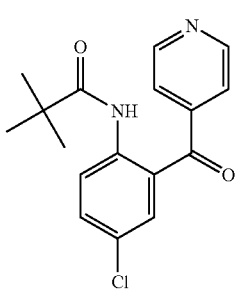

LC-MS showed the product to be >95% pure and to have the expected M.W. of 317 (M+H+). ¹H NMR (Bruker 300 MHz, CDCl₃, shifts relative to the solvent peak at 7.24 ppm) δ 10.06 (s, 1H), δ 8.87 (d, 2H), δ 8.8 (d, 1H), δ 7.61 (d, 1H), δ 7.50 (d, 2H), δ 7.47 (s, 1H), δ 1.35 (s, 9H).

Procedure M

A solution of the pivaloyl protected (2-amino-5-chloro-phenyl)-pyridin-4-yl-methanone from Procedure L (2 g) was dissolved in 25 mL of ethanol along with 8 mL of 6 N HCl. The mixture was brought to reflux for 7 hours. The ethanol was removed by rotary evaporation and the solution neutralized with 6 N NaOH. The precipitated solid was collected by filtration, washed with water, and dried to yield (2-amino-5-chloro-phenyl)-pyridin-4-yl-methanone.
The following example was prepared using Procedure M:

Example 43

(2-Amino-5-chloro-phenyl)-pyridin-4-yl-methanone

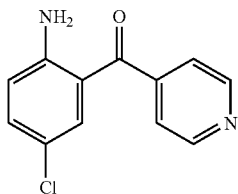

LC-MS showed the product to be >95% pure and to have the expected M.W. of 233. (M+H+). ¹H NMR (Bruker 300 MHz, CDCl₃, shifts relative to the solvent peak at 7.24 ppm) δ 8.80 (d, 2H), δ 7.45 (d, 2H), δ 7.29 (m, 2H), δ 6.70 (d, 1H), δ 6.33 (br s, 2H).

(2-Amino-5-chloro-phenyl)-pyridin-4-yl-methanones prepared using the method depicted in Scheme IV can be converted to the corresponding aryl sulfonamide or heteroaryl sulfonamide using Procedure G or H. The following example was prepared using the procedure depicted in Scheme IV followed by Procedure G or H:

Example 44

N-[4-Chloro-2-(pyridine-4-carbonyl)-phenyl]-4-ethyl-benzenesulfonamide

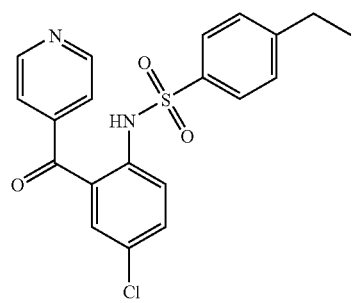

LC-MS showed the product to be >95% pure and to have the expected M.W. of 401 (M+H+); ¹H NMR (Bruker 300 MHz, CDCl₃, shifts relative to the solvent peak at 7.24 ppm) δ 10.0 (s, 1H), δ 7.78 (d, 1H), δ 7.64-7.58 (m, 3H), δ 7.52 (d, 1H) δ 7.34-7.21 (m, 3H), δ 7.17-7.21 (m, 3H), δ 2.58 (m, 2H), δ 1.15 (m, 3H).

VI. Synthesis of Sulfones and Sulfoxides

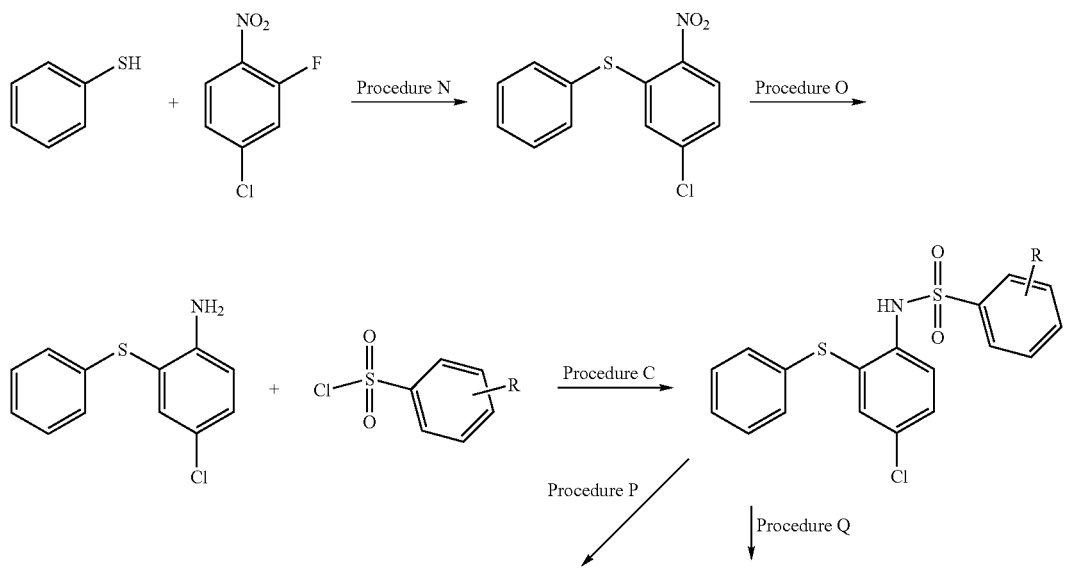

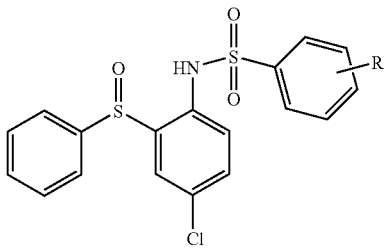

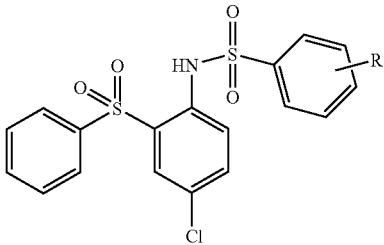

Procedure N

Production of
4-Chloro-1-nitro-2-phenylsulfanyl-benzene

To a solution of 2 g of 2-fluoro-4-chloro-nitrobenzene in 50 ml DMF and 1.25 ml of thiophenol was added 1.9 ml triethylamine at room temperature. The mixture was stirred for one hour. One hundred mL of water was added and a yellow solid crashed out of solution. The solid was collected by filtration and dried. Yield: 50-70%. LC-MS showed a single peak with the expected (M+H$^+$) of 267.

Procedure O

Production of
4-Chloro-2-phenylsulfanyl-phenylamine

To a suspension of 1.8 g of 2-benzylthio-4-chloro-nitrobenzene in 100 ml ethanol was added 2 g powdered iron and 20 mL of 0.33N NH$_4$Cl. The mixture was heated at 70° C. for 6 hr. The mixture was cooled and filtered through a pad of Celite. The filtrate was condensed and purified by flash chromatography (hexane/ethyl acetate 4:1 as eluent) to yield 1.25 g of an oil. LC-MS showed a single peak with the expected (M+H$^+$) of 236.

The following example was prepared by Procedure C:

Example 116

(4-Chloro-2-phenylsulfanyl-phenyl)-4-isopropoxy-benzenesulfonamide

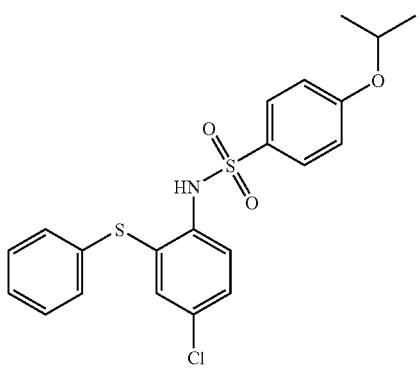

The product showed a single peak by LC-MS with the expected (M+H$^+$) of 434.

Procedure P

To a solution of the 0.5 g of the sulfide from procedure C in 20 ml DCM, was added one equivalent of m-chloro peroxybenzoic acid (mCPBA). The mixture was stirred at room temperature overnight. The mixture was concentrated and purified by flash chromatography (hexane/ethyl acetate=2:1 as eluent) to give 0.12 g of white solid as product.

The following example was prepared using Procedure P:

Example 63

N-(2-Benzenesulfinyl-4-chloro-phenyl)-4-isopropoxy-benzenesulfonamide

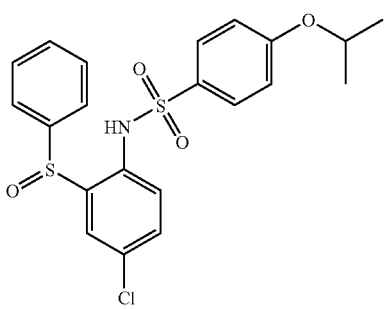

LC-MS showed a single peak with the expected (M+H$^+$) 450.

Procedure Q

To a solution of the 0.5 sulfide from procedure C in 20 ml DCM, added two equivalents of mCPBA. The mixture was stirred at room temperature overnight. The mixture is concentrated and purified by flash chromatography (hexane/ethyl acetate=2:1 as eluent) to give 0.14 g of white solid as product.

71

The following example was prepared using Procedure Q.

Example 117

N-(2-Benzenesulfonyl-4-chloro-phenyl)-4-isopropoxy-benzenesulfonamide

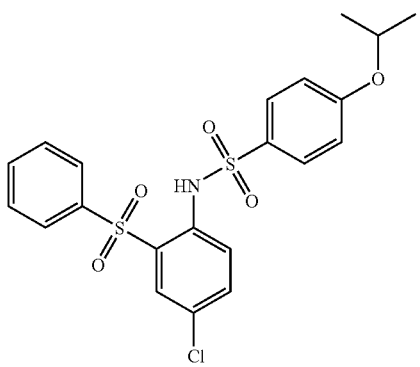

LC-MS showed a single peak with the expected (M+H⁺) 466.

The following example was prepared using Procedure G:

Example 118

N-[4-Chloro-2-(pyridine-4-carbonyl)-phenyl]-4-isopropoxy-benzenesulfonamide

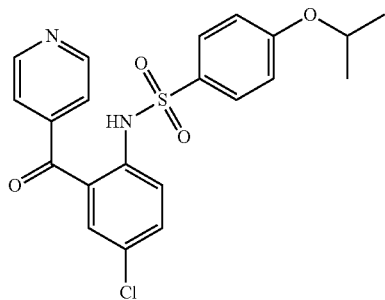

LC-MS showed a single peak with the expected (M+H⁺) of 431.

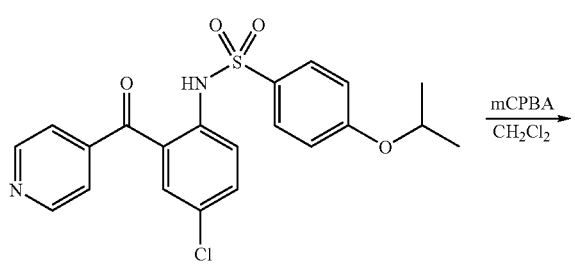

72

-continued

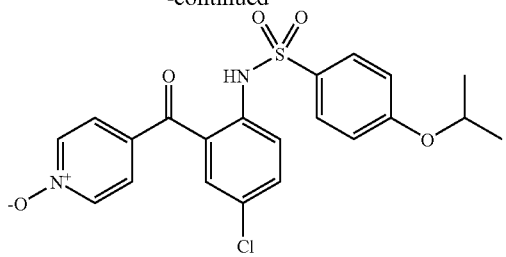

Procedure R

N-[4-Chloro-2-(pyridine-4-carbonyl)-phenyl]-4-isopropoxy-benzensulfonamide (60 mg) was dissolved in 5 mL of dichloromethane. 1.05 eq. of mCPBA was added and the mixture stirred at room temperature overnight. The solvent was removed by rotary evaporation and the residue chromatographed on silica gel (hexane /ethyl acetate=1:1 as eluent) to give the product. Yield: 95%.

The following example was prepared using Procedure R:

Example 119

N-[4-Chloro-2-(1-oxy-pyridine-4-carbonyl)-phenyl]-4-isopropoxy-benzenesulfonamide

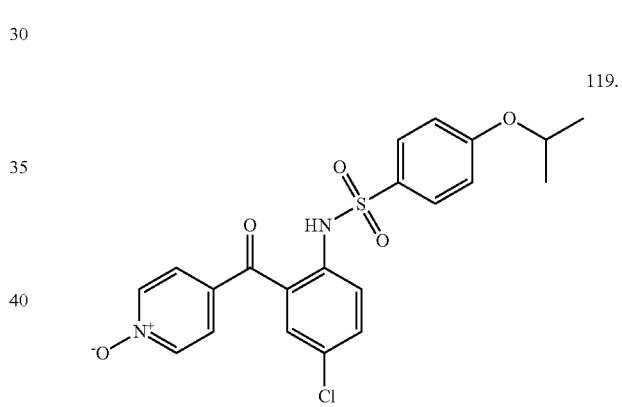

LC-MS showed a single peak with the expected (M+H⁺) of 447.

Other examples listed herein can be made by the general procedures outlined above.

Biological Data

I. FMAT Assay: FMAT Assay determine inhibitors of TECK binding to human CCR9 receptors:

A CCR9 assay buffer was prepared by adding 5 mL of 1M HEPES, 1.25 mL of 1M CaCl$_2$, 1.5 mL of 1M MgCl$_2$, 14 mL of 5M NaCl, 0.5 g fatty acid free bovine serum albumin, and 1 mL of 5% azide were added to 400 mL of distilled, deionized water (ddH$_2$O). The solution was mixed until all the fatty acid free bovine serum albumin was dissolved. After pH was adjusted to 7.4, the final volume was adjusted to 500 mL, and the solution was filtered through a 0.2 μm filter.

A 1000 nM biotinylated human TECK in assay buffer was prepared. A 14 solution of Cy5-α-Biotin working solution was prepared. Biotinylated TECK and Cy5-α-Biotin working solutions were mixed right before cells were ready to be added into wells. 13 mL of assay buffer was added to a 50 mL polyethylene tube. 5.6 μL of 1000 nM biotinylated TECK working solution and 178 μL of 14 μg/mL Cy5-α-Biotin working solution were added to the tube and mixed. The final biotinylated TECK concentration was 0.4 nM and the final Cy5-α-Biotin concentration 0.064 µg/mL.

Cells were plated right before all other reagents are added to wells. Cells were collected and centrifuged in a tabletop centrifuge at 1200 rpm for 5 minutes. The supernatant was removed by vacuum without disturbing cell pellet. The cells were resuspended in 5 mL of assay buffer. The cells were counted by adding 1 mL of a cell suspension to an eppendorf tube. Then 150 µL of this suspension was added to 150 µL, of Trypan Blue. Then 10 µL of Trypan Blue suspension was added to hemocytometer, and the cell number per mL was calculated. The cells were resuspended with CCR9 assay buffer to final $0.2 \times 10^6$ cells/mL for the assay. Approximately $2.6 \times 10^6$ cells for 1 384 well plate was needed.

20 µL of a test compound dissolved in DMSO was added to a well a polypropylene 384 well plate. Multiple compounds were tested simultaneously by adding a different test compound to each well. A control of 20 µL of DMSO in assay buffer was prepared. 20 µL of the Biotin-Teck and Cy5-α-Biotin mixed solution was added to each well of the polypropylene plate. 20 µL of cells suspension at $0.2 \times 10^6$/mL was added to each well. The assay plate was incubated on a rotator at room temperature for 1.5 hour. FMAT was read (PMT=490/518 or 537/568, threshold set at 1 standard deviation).

II. FLIPR Assay: FLIPR Assay determines inhibitors of TECK induced response in Chinese Hamster Ovary (CHO) cells that over express recombinant human CCR9 and the Ga16 protein.

The day before the assay was run, CHO cells were diluted to give appropriately 10,000 cells/well (in a volume of 50 mL). Each well of the 384 black/clear plate was then seeded with 50 mL of the diluted cell suspension. The cell plates were placed in a 37° C. tissue culture incubator at 6% $CO_2$ overnight.

A wash buffer and a dye loading solution were prepared on the day the assay was preformed. The wash buffer was prepared by mixing 880 mL of Nanopure water, 100 mL of 10×HBSS and 20 mL of 1M HEPES to give 1 L of a 1×HBSS and 20 mM HEPES solution. 1 g of BSA (bovine serum albumin) was added to the 1×HBSS/20 mM HEPES solution. A 250 mM probenecid stock solution was prepared by dissolving 710 mg of probenecid in 5 mL of 1 N NaOH and 5 mL of previously prepared 1×HBSS/20 mM HEPES/0.1% BSA buffer. 10 mL of 250 mM probenecid was added to the 1×HBSS/20 mM HEPES/0.1% BSA buffer to give a wash buffer having 1×HBSS/20 mM HEPES/2.5 mM probenecid/0.1% BSA.

For each 384 well plate, 11 mL of 2×FLUO-3 dye loading solution was required. The 2×FLUO-3 dye loading solution prepared by adding 22 mL of DMSO (100%) to each of 2×50 mg vials of FLUO-3. The vials were vortexed, then 22 mL of 20% pluronic acid was added to each 50 mg vial of FLUO-3 and vortex. 88 mL of reconstituted FLUO-3 stock solution was added to 11 mL of 1× wash buffer.

Each cell plate was washed with the wash buffer. At the end of the wash, there was 25 mL residual volume per well. 25 mL of dye loading solution was added to each well of the 384 plate. The plates were placed in an incubator for at least 1 hour. A yellow plate calibration plate was run on a FLIPR 384, and a standard deviation of less than 3.5% was obtained.

10 mM stock concentrations of compounds in 100% DMSO were prepared and stored at room temperature. Stock concentrations (100× final assay concentration) 9×1:3 serial dilutions in 100% DMSO were prepared in order to carry out 10 point concentration response curves. 3× final assay concentration were prepared by making 1 in 33.3 dilutions of the 100× stocks in wash buffer and were plated into Greiner 384 well plates. 10 point concentration response curves started at 100 mM, 10 mM or 1 mM (final assay concentration). The 1st compound was added to wells A1-A10 and other compounds were added down the plate to P1-P10. Columns 11 and 12 were control wells, with FLIPR buffer (with 3% DMSO) added to wells A11-H12. The remaining compounds were added to A13-A22 down through P13-P22. Each compound was tested in triplicate.

Ligand (rhTECK) plate at 4× ligand $EC_{50}$ (final assay concentration) in wash buffer was prepared and plated into a Greiner 384 well plate. Appropriate amount of 4× ligand was added to wells A1 through P10 and A13 through P22. In columns 11 and 12, FLIPR wash buffer was added to wells A11-D12 and 4× ligand solution was added to wells E11-H12.

The cell plates were incubated at least a 1 hour with the dye solution, then washed with wash buffer. At the end of the wash, there was 25 mL residual volume per well. The cell plate were loaded onto the stacker of FLIPR-384. Individual well activity (IWA) was measured, using the max-min function between timepoints 88-145. Data was expressed as % inhibition of rhTECK induced response, and $IC_{50}$ values were calculated for compounds displaying antagonist activity.

Inhibition of binding of human TECK to human CCR9 receptors (FMAT assay) and inhibition of human TECK induced response (FLIPR)

Of the compounds tested in the FMAT assay described above, the following provided an $IC_{50}$ value less than or equal to about 1.0 µM: 17-21, 31-34, 44, 70, 73, 74, and 115.

Of the compounds tested in the FLIPR assay described above, the following provided an $IC_{50}$ value less than or equal to about 1.0 µM: 8-13, 14-15, 17-20, 22-24, 31-36, 44, 49, 63, and 69-89, 116-143.

What is claimed is:
1. A method of treating an inflammatory bowel disease in a subject in need thereof, comprising administering to the subject an effective amount of a compound represented by the following structural formula:

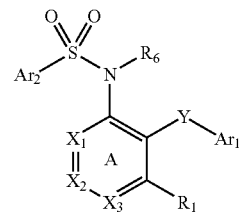

or a pharmaceutically acceptable salt thereof, wherein:
Y is C=O, S(O), or $S(O)_2$;
$X_1$, $X_2$, and $X_3$ are each independently CR;
R, for each occurrence, and $R_1$ are each independently H, an aliphatic group, haloalkyl, aryl, arylalkyl, alkoxy, cycloalkoxy, haloalkoxy, aryloxy, arylalkoxy, alkylthio, halo, nitro, cyano, hydroxy, $NR_{11}CO_2R_{12}$, $C(O)N(R_{11})_2$, $C(O)R_{12}$, $CO_2R_{12}$, $OC(O)N(R_{11})_2$, $OC(O)R_{12}$, $N(R_{11})_2$, or $NR_{11}C(O)R_{12}$;
wherein $R_{11}$, for each occurrence is, independently, H or an aliphatic group, and $R_{12}$ is an aliphatic group;
$R_6$ is H, an aliphatic carbonyl group, or an aliphatic ester;
$Ar_1$ is substituted or unsubstituted phenyl; and
$Ar_2$ is a substituted or unsubstituted aryl group or a substituted or unsubstituted heteroaryl group.

2. The method of claim 1, wherein the inflammatory bowel disease is selected from ulcerative colitis, Crohn's disease, ileitis, Celiac disease, nontropical Sprue, enteritis, enteropathy associated with seronegative arthropathies, microscopic or collagenous colitis, eosinophilic gastroenteritis, or pouchtis resulting after proctocolectomy, and ileoanal anastomosis.

3. The method of claim 1, wherein the inflammatory disease or condition is Crohn's disease or colitis.

4. The method of claim 1, wherein the inflammatory disease or condition is Celiac's disease.

5. The method of claim 1, wherein the compound has the following structural formula:

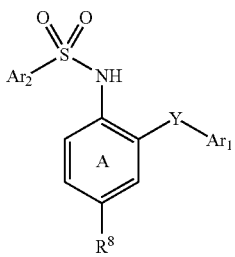

or a pharmaceutically acceptable salt thereof, wherein:
Y is C=O, S(O), or S(O)$_2$;
$R^8$ is halo, nitro, alkylcarbonyl, or trihaloalkyl;
$Ar_1$ is substituted or unsubstituted phenyl; and
$Ar_2$ is a substituted or unsubstituted aryl group or a substituted or unsubstituted heteroaryl group, and a pharmaceutically acceptable carrier.

6. The method of claim 5, wherein $Ar^1$ is optionally substituted phenyl, $Ar^2$ is optionally substituted phenyl or thienyl, Y is C=O, and $R^8$ is halo.

7. The method of claim 6, wherein $R^8$ is chloro.

8. The method of claim 1, wherein the compound is represented by the following structural formula:

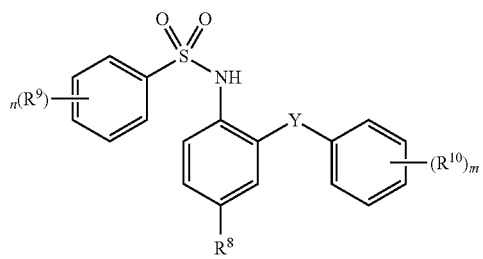

wherein:
Y is C=O;
$R_8$ is halo, nitro, alkylcarbonyl, or trihaloalkyl;
m and n are each, independently, 0 or an integer from 1 to 3;
each $R_9$ is, independently, aliphatic, haloalkyl, aryl, arylalkyl, alkoxy, cycloalkoxy, haloalkoxy, aryloxy, arylalkoxy, alkylthio, halo, nitro, cyano, hydroxy, $NR_{11}CO_2R_{12}$, $C(O)N(R_{11})_2$, $C(O)R_{12}$, $CO_2R_{12}$, $OC(O)N(R_{11})_2$, $OC(O)R_{12}$, $N(R_{11})_2$, or $NR_{11}C(O)R_{12}$; or two adjacent $R_9$ groups taken together with the atoms to which they are attached form a fused, saturated, unsaturated or partially unsaturated 5 to 7 membered ring having 0, 1, or 2 heteroatoms selected from N, O, and S;
wherein each $R_{11}$ is, independently, selected from H or an aliphatic group; and $R_{12}$ is an aliphatic group; and
each $R_{10}$ is, independently, halo, aliphatic group, alkoxy, or haloalkyl; or two adjacent $R_{10}$ groups taken together with the atoms to which they are attached form a fused, saturated, unsaturated or partially unsaturated 5 to 7 membered ring having 0, 1 or 2 heteroatoms selected from N, O, and S.

9. A pharmaceutical composition comprising a compound having the following structural formula:

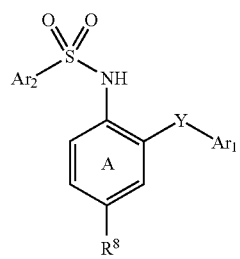

or a pharmaceutically acceptable salt thereof, wherein:
Y is C=O, S(O), or S(O)$_2$;
$R^8$ is halo, nitro, alkylcarbonyl, or trihaloalkyl;
$Ar_1$ is substituted or unsubstituted phenyl; and
$Ar_2$ is a substituted or unsubstituted aryl group or a substituted or unsubstituted heteroaryl group, and a pharmaceutically acceptable carrier.

10. The pharmaceutical composition of claim 9, wherein $Ar^1$ is optionally substituted phenyl, $Ar^2$ is optionally substituted phenyl or thienyl, Y is C=O, and $R^8$ is halo.

11. The pharmaceutical composition of claim 10, wherein $R^8$ is chloro.

12. The pharmaceutical composition of claim 9, wherein the compound is represented by the following structural formula:

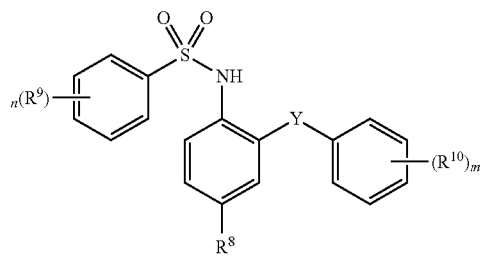

wherein:
Y is C=O;
$R_8$ is halo, nitro, alkylcarbonyl, or trihaloalkyl;
m and n are each, independently, 0 or an integer from 1 to 3;
each $R_9$ is, independently, aliphatic, haloalkyl, aryl, arylalkyl, alkoxy, cycloalkoxy, haloalkoxy, aryloxy, arylalkoxy, alkylthio, halo, nitro, cyano, hydroxy, $NR_{11}CO_2R_{12}$, $C(O)N(R_{11})_2$, $C(O)R_{12}$, $CO_2R_{12}$, $OC(O)N(R_{11})_2$, $OC(O)R_{12}$, $N(R_{11})_2$, or $NR_{11}C(O)R_{12}$; or two adjacent $R_9$ groups taken together with the atoms to which they are attached form a fused, saturated, unsaturated or partially unsaturated 5 to 7 membered ring having 0, 1, or 2 heteroatoms selected from N, O, and S;
wherein each $R_1$, is, independently, selected from H or an aliphatic group; and $R_{12}$ is an aliphatic group; and
each $R_{10}$ is, independently, halo, aliphatic group, alkoxy, or haloalkyl; or two adjacent $R_{10}$ groups taken together

77 with the atoms to which they are attached form a fused, saturated, unsaturated or partially unsaturated 5 to 7 membered ring having 0, 1 or 2 heteroatoms selected from N, O, and S.

13. A compound having the following structural formula:

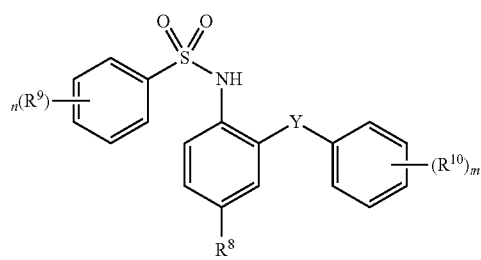

or a pharmaceutically acceptable salt thereof
wherein:
Y is C=O;
$R_8$ is halo, nitro, alkylcarbonyl, or trihaloalkyl;
m and n are each, independently, 0 or an integer from 1 to 3;
each $R_9$ is, independently, aliphatic, haloalkyl, aryl, arylalkyl, alkoxy, cycloalkoxy, haloalkoxy, aryloxy, arylalkoxy, alkylthio, halo, nitro, cyano, hydroxy, $NR_{11}CO_2R_{12}$, $C(O)N(R_1$ $C(O)R_{12}$, $CO_2R_{12}$, $OC(O)N(R_1$ $OC(O)R_{12}$, $N(R_{11})_2$, or $NR_{11}C(O)R_{12}$; or two adjacent $R_9$ groups taken together with the atoms to which they are attached form a fused, saturated, unsaturated or partially unsaturated 5 to 7 membered ring having 0, 1, or 2 heteroatoms selected from N, O, and S;
  wherein each $R_{11}$ is, independently, selected from H or an aliphatic group; and $R_{12}$ is an aliphatic group; and
each $R_{10}$ is, independently, halo, aliphatic group, alkoxy, or haloalkyl.

14. A pharmaceutically acceptable salt of a compound selected from:

63.

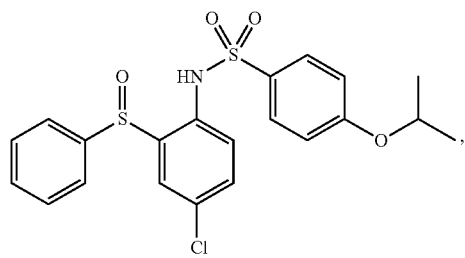

69.

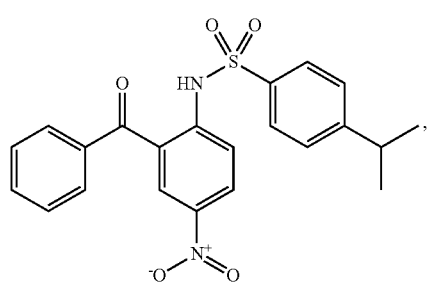

78
-continued

70.

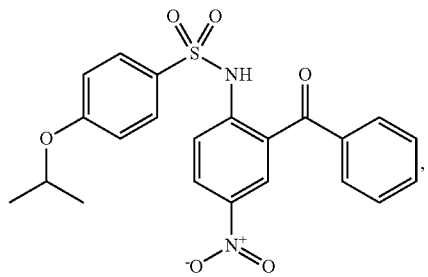

72.

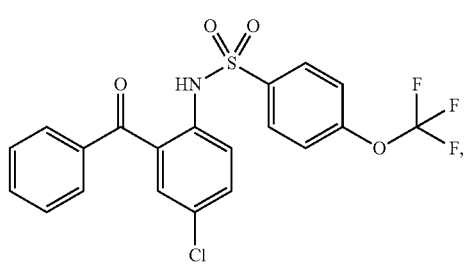

74.

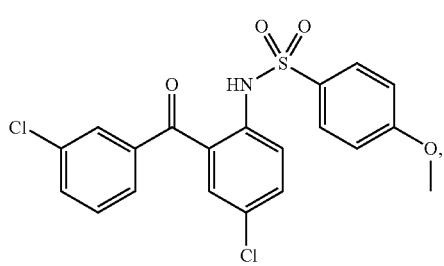

76.

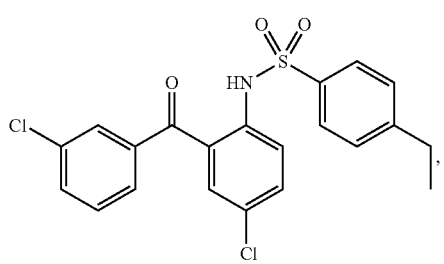

77.

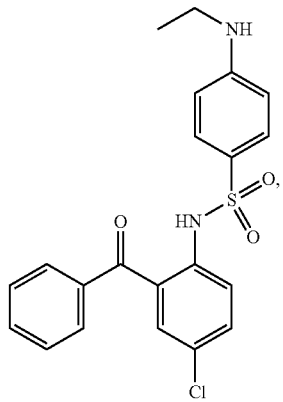

80.
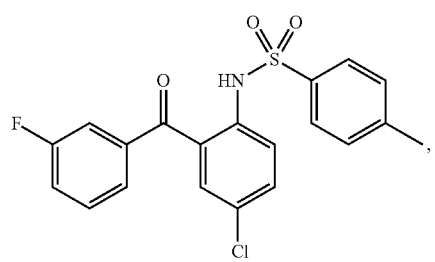
81.
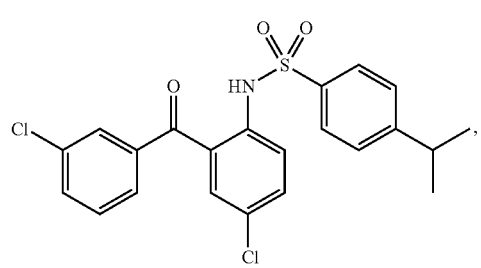
83.
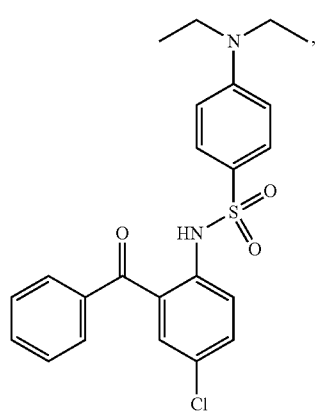
84.
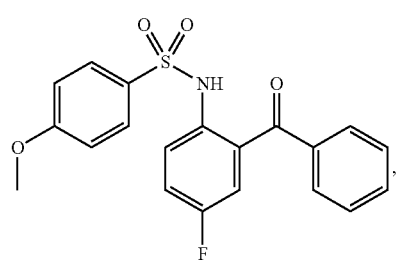
86.
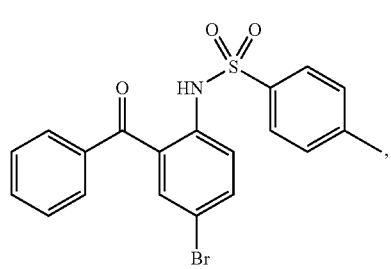
89.
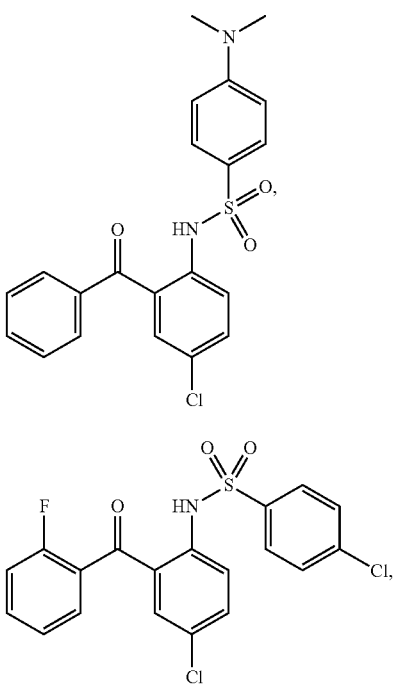
91.
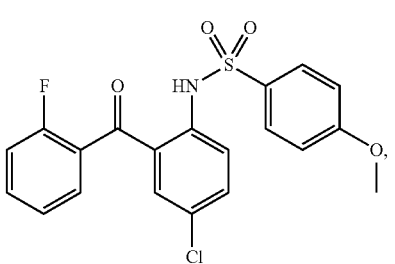
92.
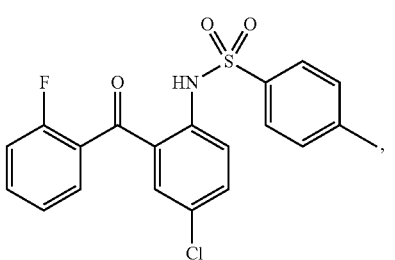
97.
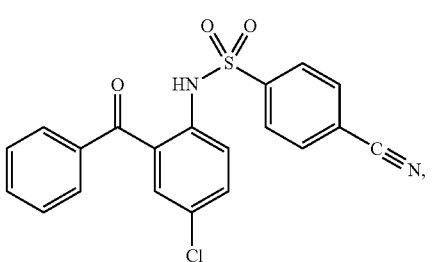
103.

107.
109.
110.
114.
116.
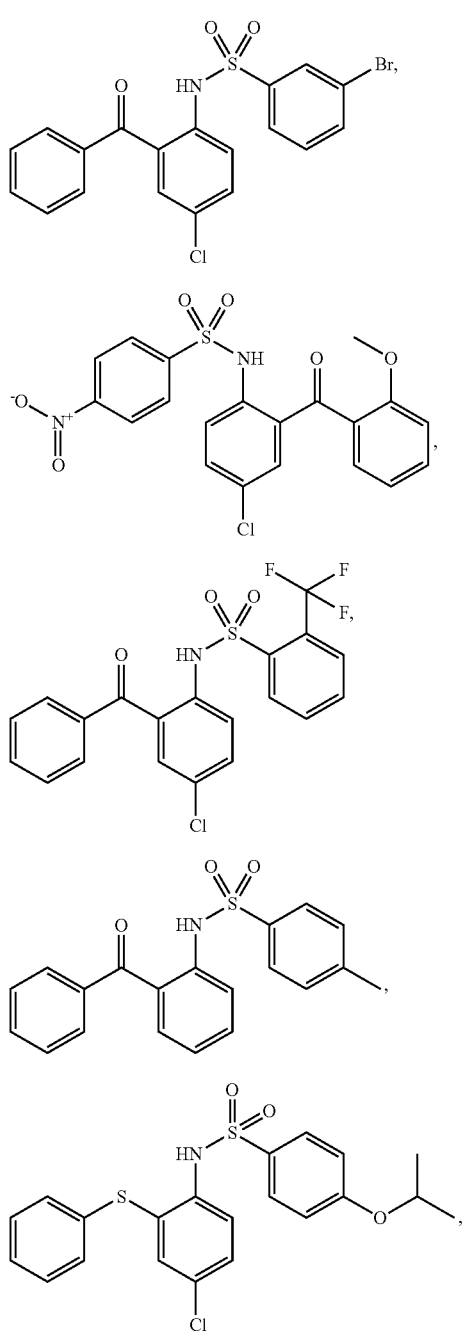
117.
127.
132. or
141.
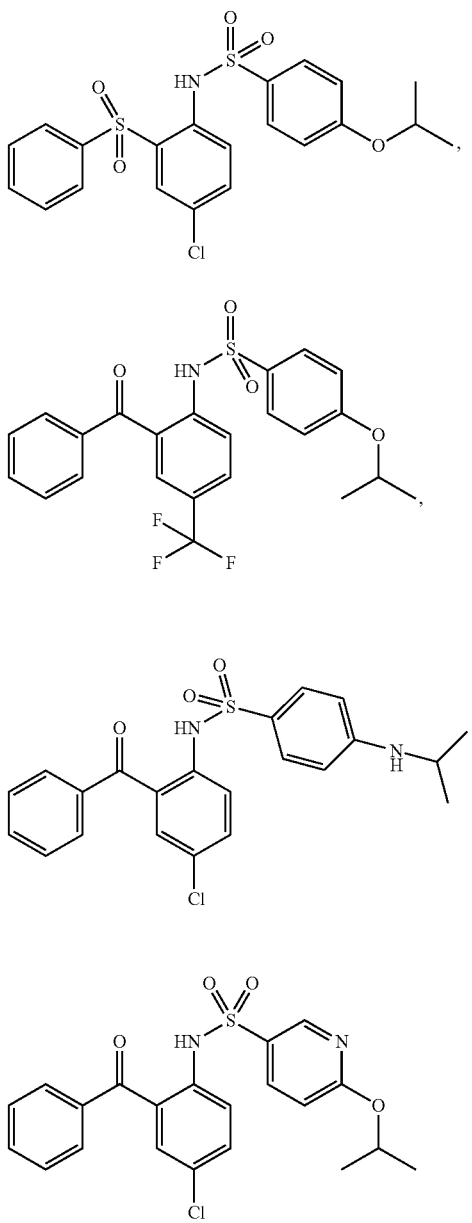
* * * * *